(12) United States Patent
Hubbell et al.

(10) Patent No.: US 9,879,062 B2
(45) Date of Patent: Jan. 30, 2018

(54) PROTEIN-BINDING PEPTIDE ISOLATED FROM PLACENTA GROWTH FACTOR

(71) Applicant: EPFL-TTO, Lausanne (CH)

(72) Inventors: Jeffrey A. Hubbell, Preverenges (CH); Mikael Martino, Nyon (CH); Priscilla S. Maithili Briquez, Chavannes-pres-Renens (CH)

(73) Assignee: Ecole Polytechnique Federale De Lausanne, Lausanne (CH)

( * ) Notice: Subject to any disclaimer, the term of this patent is extended or adjusted under 35 U.S.C. 154(b) by 3 days.

(21) Appl. No.: 13/933,444

(22) Filed: Jul. 2, 2013

(65) Prior Publication Data

US 2014/0010832 A1    Jan. 9, 2014

Related U.S. Application Data

(60) Provisional application No. 61/667,630, filed on Jul. 3, 2012.

(51) Int. Cl.
| | |
|---|---|
| *A61K 39/00* | (2006.01) |
| *A61K 39/385* | (2006.01) |
| *A61K 38/18* | (2006.01) |
| *C07K 14/475* | (2006.01) |
| *A61K 38/24* | (2006.01) |
| *C07K 14/51* | (2006.01) |
| *C07K 14/495* | (2006.01) |
| *C07K 14/52* | (2006.01) |
| *A61K 38/00* | (2006.01) |

(52) U.S. Cl.
CPC .......... *C07K 14/51* (2013.01); *A61K 39/0011* (2013.01); *C07K 14/475* (2013.01); *C07K 14/495* (2013.01); *C07K 14/52* (2013.01); *A61K 38/00* (2013.01); *A61K 2039/6031* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 5,227,165 A | 7/1993 | Domb et al. | |
| 5,994,300 A * | 11/1999 | Bayne | C07K 14/52 424/569 |
| 6,022,564 A | 2/2000 | Takechi et al. | |
| 6,090,925 A | 7/2000 | Woiszwillo et al. | |
| 6,224,794 B1 | 5/2001 | Amsden et al. | |
| 6,331,422 B1 | 12/2001 | Hubbell et al. | |
| 6,607,740 B1 | 8/2003 | Hubbell et al. | |
| 6,723,344 B2 | 4/2004 | Sakiyama-Elbert et al. | |
| 6,894,022 B1 | 5/2005 | Hubbell et al. | |
| 7,060,681 B2 | 6/2006 | Hubbell et al. | |
| 7,241,730 B2 | 7/2007 | Hubbell et al. | |
| 7,744,912 B1 | 6/2010 | Hubbell et al. | |
| 2007/0202178 A1 | 8/2007 | Schense et al. | |
| 2007/0264227 A1 | 11/2007 | Lutolf et al. | |
| 2008/0031899 A1 | 2/2008 | Reddy et al. | |
| 2010/0003338 A1 | 1/2010 | Hubbell et al. | |
| 2010/0055189 A1 | 3/2010 | Hubbell et al. | |

FOREIGN PATENT DOCUMENTS

| | | |
|---|---|---|
| WO | 2005016963 | 2/2005 |
| WO | WO 2005016963 A2 * | 2/2005 |
| WO | 2005030240 | 4/2005 |

OTHER PUBLICATIONS

Moriyama et al. Drug Delivery. May 2012; 19(4): 202-207.*
Bowie et al. Science, 247:1306-1310, 1990.*
Whisstock et al. Quarterly Reviews in Biophysics. 36(3):307-340, 2007.*
Lazar et al. Molecular Cellular Biology. 1988; 8(3):1247-1252.*
Krilleke et al. Molecular Mapping and Functional Characterization of the VEGF164 Heparin-binding Domain. Journal of Biological Chemistry, 2007; 282(38):28045-28056.*
Bowie et al. Deciphering the message in protein sequences: tolerance to amino acid substitutions. Science, 247:1306-1310, 1990.*
Whisstock et al. Prediction of protein function from protein sequence and structure. Quarterly Reviews in Biophysics. 36(3):307-340, 2007.*
Lazar et al. Transforming growth factor alpha: mutation of aspartic acid 47 and leucine 48 results in different biological activities. Molecular Cellular Biology. 1988; 8(3):1247-1252.*
Devalapally et al., "Poly(ethylene oxide)-Modified Poly(beta-amino ester) Nanoparticles as a pH-Sensitive System for Tumor-Targeted Delivery of Hydrophobic Drug: Part 3. Therapeutic Efficacy and Safety Studies in Ovarian Cancer Xenograft Model", Cancer Chemother Pharmacol, vol. 59:477-484 (Jul. 22, 2006).
Lutolf et al., "Synthesis and Phsicochemical Characterization of End-Linked Poly(ethylene glycol)-co-Peptide Hydrogels Formed by Michael-Type Addition", Biomacromolecules, vol. 4:713-722 (2003).
Martino et al, "The 12th-14th Type III Repeats of Fibronectin Function as a Highly Promiscuous Growth Factor-Binding Domain", The FASEB Journal,24:4711-4721 (Dec. 2010).
Ribatti, "The Discovery of the Placental Growth Factor and its Role in Angiogenesis: A Historical Review" Angiogenesis, 11:215-221 (2008).
Tobio et al, "Stealth PLA-PEG Nanoparticles as Protein Carriers for Nasal Administration", Pharmaceutical Research, vol. 15(2):270-275 (1998).
International Search Report and Written Opinion from corresponding PCT Application No. PCT/US2013/064016, 12 pages, dated Jul. 3, 2013.
He et al., "Placental Growth Factor and Related Research", Medical Review, vol. 17(13):1936-1939 (Jul. 31, 2011).

* cited by examiner

*Primary Examiner* — Vanessa L Ford
*Assistant Examiner* — Sandra Dillahunt
(74) *Attorney, Agent, or Firm* — Christensen, Fonder, Dardi & Herbert PLLC; Curtis Herbert

(57) ABSTRACT

Embodiments of the invention are described, including materials and methods for making molecules and materials that have a specific binding domain of a PlGF2. Embodiments include, for instance, medicaments, biomaterials, biomolecules, molecular fusions, and vaccines.

28 Claims, 10 Drawing Sheets

PROTEIN-BINDING PEPTIDE ISOLATED FROM PLACENTA GROWTH FACTOR

CROSS REFERENCE TO RELATED APPLICATIONS

Figure 1:
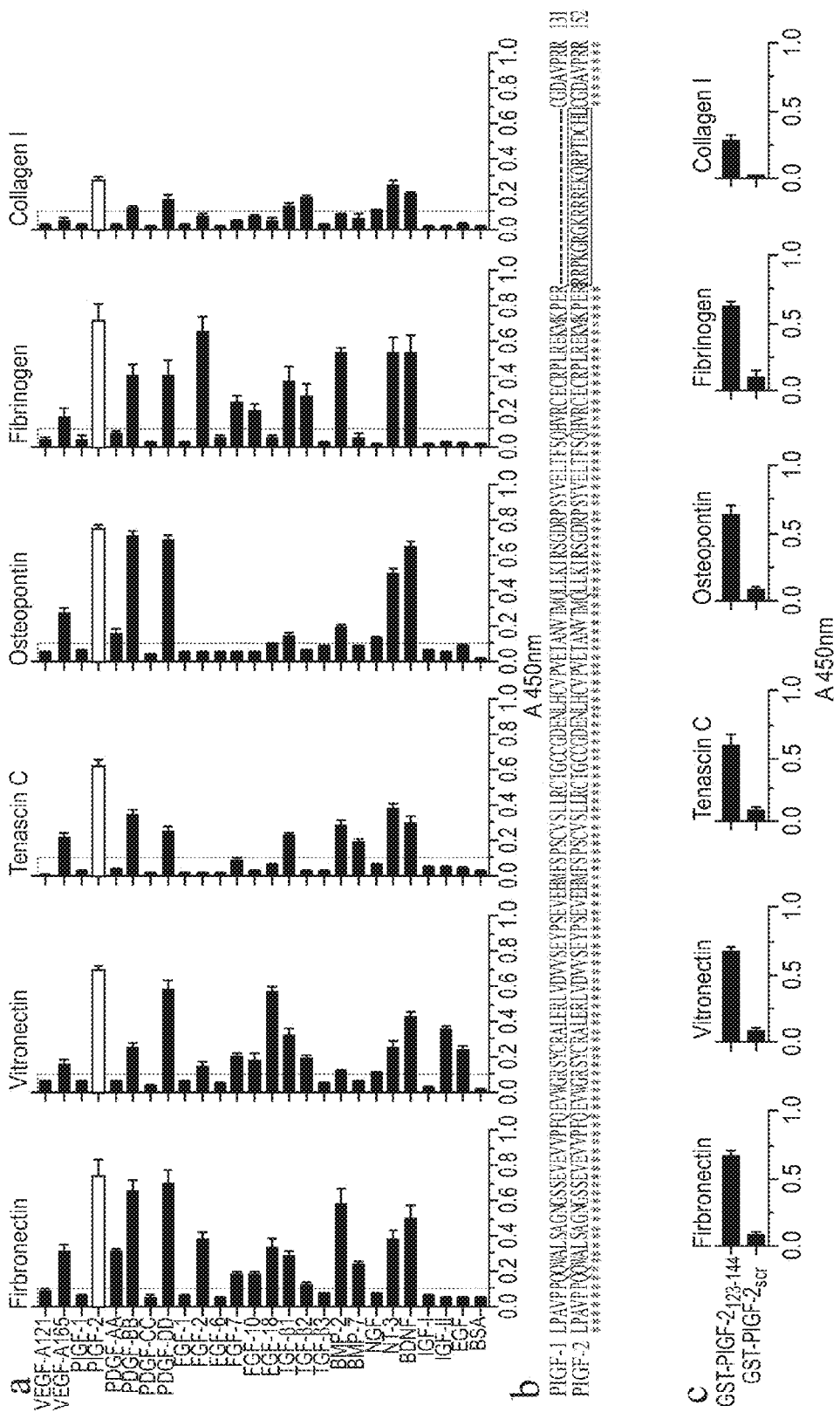

This patent application claims priority to U.S. Ser. No. 61/667,630 filed Jul. 3, 2012, which is hereby incorporated by reference herein.

TECHNICAL FIELD

The technical field, in general, relates to peptides that bind to extracellular matrices via specific binding interactions.

BACKGROUND

The extracellular matrix (ECM) provides structural support for tissue and signaling capabilities for cells. The ECM plays an important role in development and tissue repair.

SUMMARY OF THE INVENTION

As reported herein, it has been discovered that placenta growth factor (PlGF) exhibits specific binding activity towards ECM. PlGF is an angiogenic cytokine that exists in multiple splice variants. PlGF was originally identified in the placenta, where it has been proposed to control trophoblast growth and differentiation. PlGF is expressed during early embryonic development. PlGF has been shown to be expressed in the villous trophoblast, while vascular endothelial growth factor (VEGF) is expressed in cells of mesenchymal origin within the chorionic plate. PlGF is expressed in several other organs including the heart, lung, thyroid, skeletal muscle, and adipose tissue. PlGF acts as a potent stimulator of VEGF secretion by monocytes and significantly increases mRNA levels of the proinflammatory chemokines interleukin-1 beta, interleukin-8, monocyte chemoattractant protein-1, and VEGF in peripheral blood mononuclear cells of healthy subjects. PlGF induces tumor angiogenesis by recruiting circulating hematopoietic progenitor cells and macrophages to the site of the growing tumors (Ribatti D, 2008).

An embodiment is an isolated polypeptide comprising a sequence chosen from the group consisting of SEQ ID NO:4 having from 0 to 5 conservative substitutions, SEQ ID NO:5 having from 0 to 5 conservative substitutions, and subsequences thereof. Said subsequences may be chosen as exhibiting specific binding to one or more of fibrinogen, fibronectin, vitronectin, tenascin C, osteopontin, and fibrin. A dissociation constant may be specified, for example, wherein the specific binding of the polypeptide to fibrinogen has a dissociation constant ($K_D$) of less than about 100 nM, or less than about 40 nM, or less than about 25 nM.

An embodiment is a biologic delivery vehicle comprising a molecular fusion of a biological agent and a peptide comprising a sequence or subsequence of at least 6 residues of a sequence chosen from the group consisting of SEQ ID NO: 4 having from 0 to about 15% conservative substitutions and SEQ ID NO:5 having from 0 to about 15% conservative substitutions. As explained in more detail herein, the peptide exhibits specific binding to one or more of, or all, of the extracellular matrix molecules selected from the group consisting of fibrinogen, fibronectin, vitronectin, tenascin C, osteopontin, fibrin, collagen, Collagen I, and heparin sulfate. In fact, the tested peptides exhibited specific binding to all of said extracellular matrix molecules.

Examples of biologic agents are those chosen from the group consisting of a protein, a protein drug, a marker, an immunoagent, a chemokine, a cytokine, and a cell adhesion peptide. The term cytokine, as used herein, includes growth factors and morphogens.

An embodiment is a biomaterial comprising a matrix, with the matrix comprising a polypeptide comprising a sequence chosen from the group consisting of SEQ ID NO:4 having from 0 to 5 conservative substitutions, SEQ ID NO:5 having from 0 to 5 conservative substitutions, and all subsequences thereof, said peptide exhibiting specific binding to an extracellular matrix molecule. The matrix may be natural or synthetic and covalently crosslinked, crosslinked without covalent binds, or free of crosslinks.

An embodiment is a medicament comprising a peptide, vehicle, or biomaterial comprising a PlGF2, e.g, a domain of PlGF2. The medicament may be used, e.g., in a medical treatment, to make a medical composition, e.g., as a vaccine, for drug delivery, wound healing, and tissue healing, e.g., healing of a bone, fistula, or an ulcer.

BRIEF DESCRIPTION OF THE FIGURES

FIG. 1: A domain within PlGF2 ($PlGF2_{123-144}$) strongly and promiscuously binds ECM proteins. (a) GF binding to ECM proteins, measured by ELISA. A signal over 0.1 (gray box) was considered as representative of a specific binding. PlGF2 strongly binds all ECM proteins tested (gray bars). (b) Alignment of the protein sequences of the splice variants PlGF2 and PlGF-1 (which does not bind). PlGF2 contains an additional 21 amino-acid insert ($PlGF2_{123-144}$, in gray) located near the C-terminus. (c) Binding of $PlGF2_{123-144}$ to ECM proteins when fused to a non-binding model protein, GST (GST-$PlGF2_{123-144}$). A scrambled version of $PlGF2_{123-144}$ (GST-$PlGF2_{scr}$) does not bind ECM proteins. In (a) and (c), n≥3, mean±SEM. The alignment shows sequences of PlGF-1 (PlGF-1 LPAVPPQQWALSAGNGSSEVEVVPFQEVWGRSYCRALERLVDVVSEYPSEVEHMFSPSC VSLLRCTGCCGDENLHCVPVETANVTMQLLKIRSGDRPSYVELTFSQHVRCECRPLREK MKPERCGDAVPRR (SEQ ID NO:58) as compared to PlGF2 (LPAVPPQQWALSAGNGSSEVEVVPFQEVWGRSYCRALERLVDVVSEYPSEVEHMFSPS CVSLLRCTGCCGDENLHCVPVETANVTMQLLKIRSGDRPSYVELTFSQHVRCECRPLRE KMKPERRRPKRGKRRREKQRPTDCHLCGDAVPRR, SEQ ID NO:59).

FIG. 2: Binding of various GST-$PlGF2_{123-144}$ fragments to fibronectin, collagen I, heparan sulfate, and neuropilin-1. (a) Design of GST-$PlGF2_{123-144}$ fragments. (b) Binding of GST-$PlGF2_{123-144}$ fragments to fibronectin, collagen I, heparan sulfate, and neuropilin-1. The depicted alignments include fragments of GST-PlGF2: RRRPKGRGKRRREKQRPTDCHLCGDAVPRR (SEQ ID NO:60), RRRPKGRGKRRREKQRPTDCHL (SEQ ID NO:61), RRPKGRGKRRREKQRPTD (SEQ ID NO:62), RRRPKGRGKRRREKQ (SEQ ID NO:1), GKRRREKQ (SEQ ID NO:2), and RRRPKGRG (SEQ ID NO:3).

FIG. 3: The heparin-binding domain of VEGF-A165 is substituted with $PlGF2_{123-144}$ (black box) to generate VEGF-A121-$PlGF2_{123-144}$ (SEQ ID NO: 7). $PlGF2_{123-144}$ is fused to the C-terminus of PDGF-BB to generate PDGF-BB-$PlGF2_{123-144}$ (SEQ ID NO: 9) $PlGF2_{123-144}$. (gray box) containing a point mutation ($Cys_{142}$ to Ser) is inserted at the C-terminus of BMP-2 to generate BMP-2-$PlGF2_{123-144}$* (SEQ ID NO: 13).

FIG. 4: Has 2 panels. (a) Cytokines-$PlGF2_{123-144(*)}$ binding to ECM proteins (fibronectin, vitronectin, tenascin C, osteopontin, collagen I, fibrinogen) and heparan sulfate measured by ELISA. ELISA plates were coated with cytokines and further incubated with ECM proteins at increasing concentration (0.02 to 320 nM). Bound ECM proteins were detected using antibodies. The binding curve was fitted by non-linear regression to obtain the dissociation constant ($K_D$) using $A_{450\ nm}$=Bmax*[concentration]/($K_D$+[concentration]). n=3, mean±SEM. (b) Cytokines-PlGF2$_{123-144(*)}$ are retained in fibrin matrix. Fibrin matrices were made in the presence of wildtype cytokines (PlGF-1, PlGF2, VEGF-A121, VEGF-A165, PDGF-BB, and BMP-2) or modified cytokines (VEGF-A121-PlGF2$_{123-144}$, PDGF-BB-PlGF2$_{123-144}$, or BMP-2-PlGF2$_{123-144(*)}$ and further incubated in 8 volumes of physiological buffer for 7 days. The buffer was changed every day, and cumulative released of cytokines were quantified for each day. Wildtype PlGF-1, VEGF-A121, VEGF-A165, PDGF-BB, and BMP-2 were quickly released, while VEGF-A121-PlGF2$_{123-144}$, PDGF-BB-PlGF2$_{123-144}$, and BMP-2-PlGF2$_{123-144*}$ were sequestered in the matrix.

Figure 5:
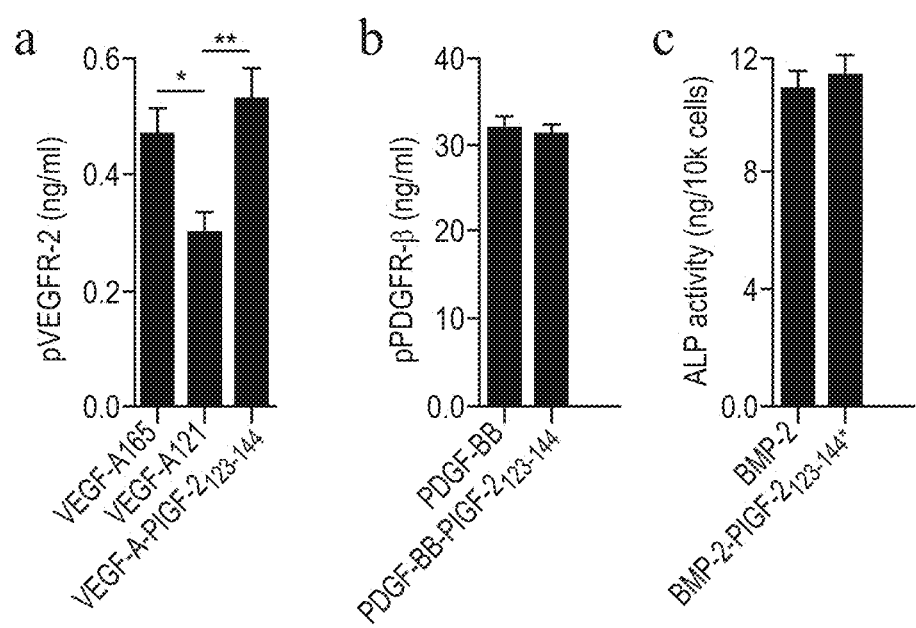

FIG. 5: In vitro, PlGF2$_{123-144}$-fused GFs shows similar bioactivity compared to wild-type GFs. (a) Human ECs were stimulated with VEGF-A121, VEGF-A165, or VEGF-A-PlGF2$_{123-144}$, and (b) human mesenchymal stem cells were stimulated with PDGF-BB or PDGF-BB-PlGF2$_{123-144}$. Phosphorylated GF receptors (VEGFR-2 and PDGFR-β) were quantified by ELISA (n=3, mean±SEM). The insertion of the PlGF2$_{123-144}$ into VEGF-A and PDGF-BB do not alter their signaling. Moreover, the insertion of PlGF2$_{123-144}$ into VEGF-A121 increases its activity to the level of VEGF-A165. As it is the case for VEGF-A165, this increased activity on receptor phosphorylation is most likely due the binding of PlGF2$_{123-144}$ to neuropilin-1, which increases VEGF-A potency in stimulating VEGFR-2 phosphorylation (Migdal M, et al., 1998; Pan Q, et al., 2007; Whitaker G B, et al., 2001). The Student t-test was used for statistical comparisons; *p<0.05, **p<0.01. (c) BMP-2-PlGF2$_{123-144*}$ was evaluated by its ability to promote ALP activity in human mesenchymal stem cells (induction of osteoblastic differentiation). Cellular ALP was quantified after 14 days of culture in presence of BMP-2 or BMP-2-PlGF2$_{123-144*}$. No differences in cell number and ALP activity were observed between cells treated with BMP-2 or BMP-2-PlGF2$_{123-144*}$. Results are expressed as ng of ALP/10 k cells (n=4, mean±SEM).

Figure 6:
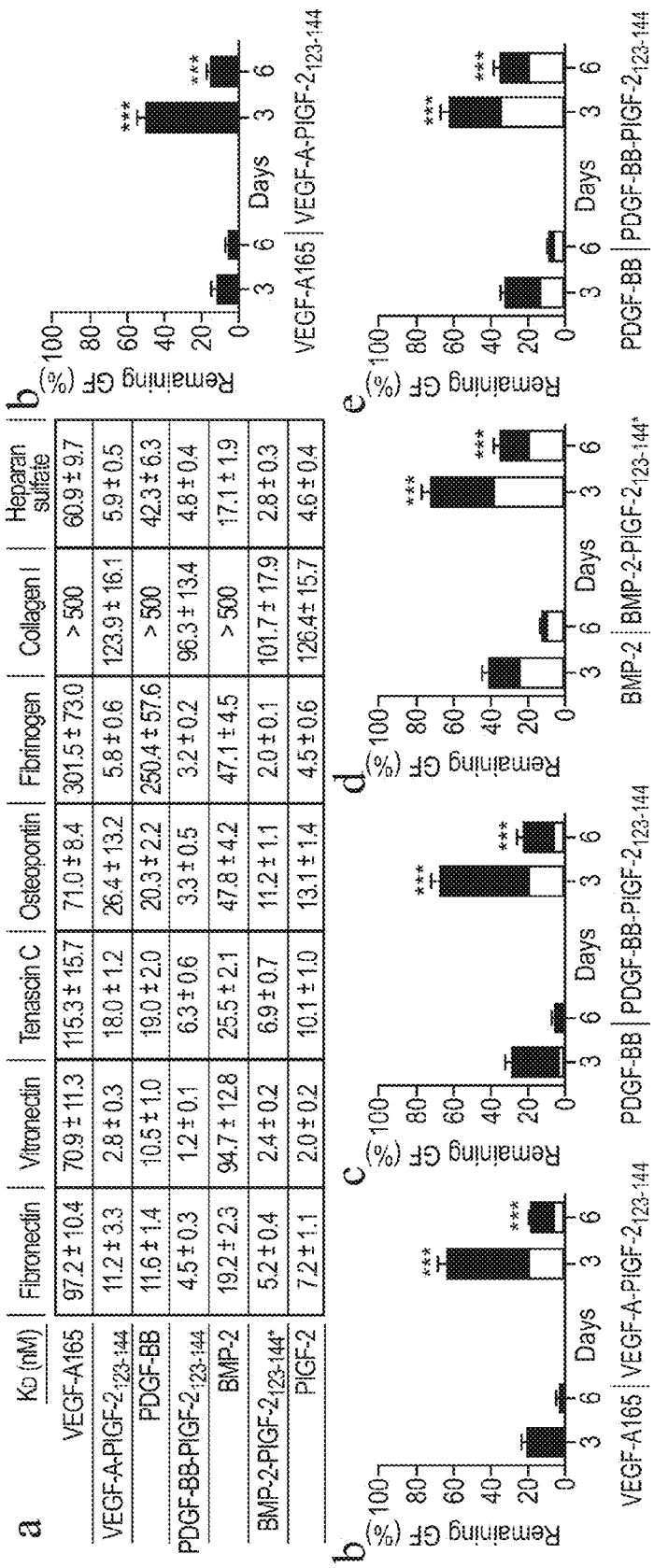

FIG. 6: PlGF2$_{123-144}$-fused GFs display enhanced affinity for ECM components. (a) Affinity (shown is $K_D$) of wild-type versus PlGF2$_{123-144}$-fused GFs for ECM proteins and heparan sulfate. n=3, mean±SEM. (b-f) PlGF2$_{123-144}$-fused GFs are retained at the site of delivery for an extended period relative to wild-type GFs. (b) VEGF-A165 and VEGF-A-PlGF2$_{123-144}$ retention when injected subcutaneously in the back skin of mice. n=6 per time point, mean±SEM. (c-f) Wildtype and PlGF2$_{123-144}$-fused GF retention when placed in 5 mm diameter defects in the mouse back skin (c,d) or mouse calvarium (e,f) filled with a fibrin matrix. Retention after 3 and 6 days in the fibrin matrix (gray bars) and the tissue surrounding the defect (black bars, 2 mm farther). n≥4 per time point, mean±SEM. For all panels, Student's t-test; p<0.01, *p<0.001.

Figure 7:
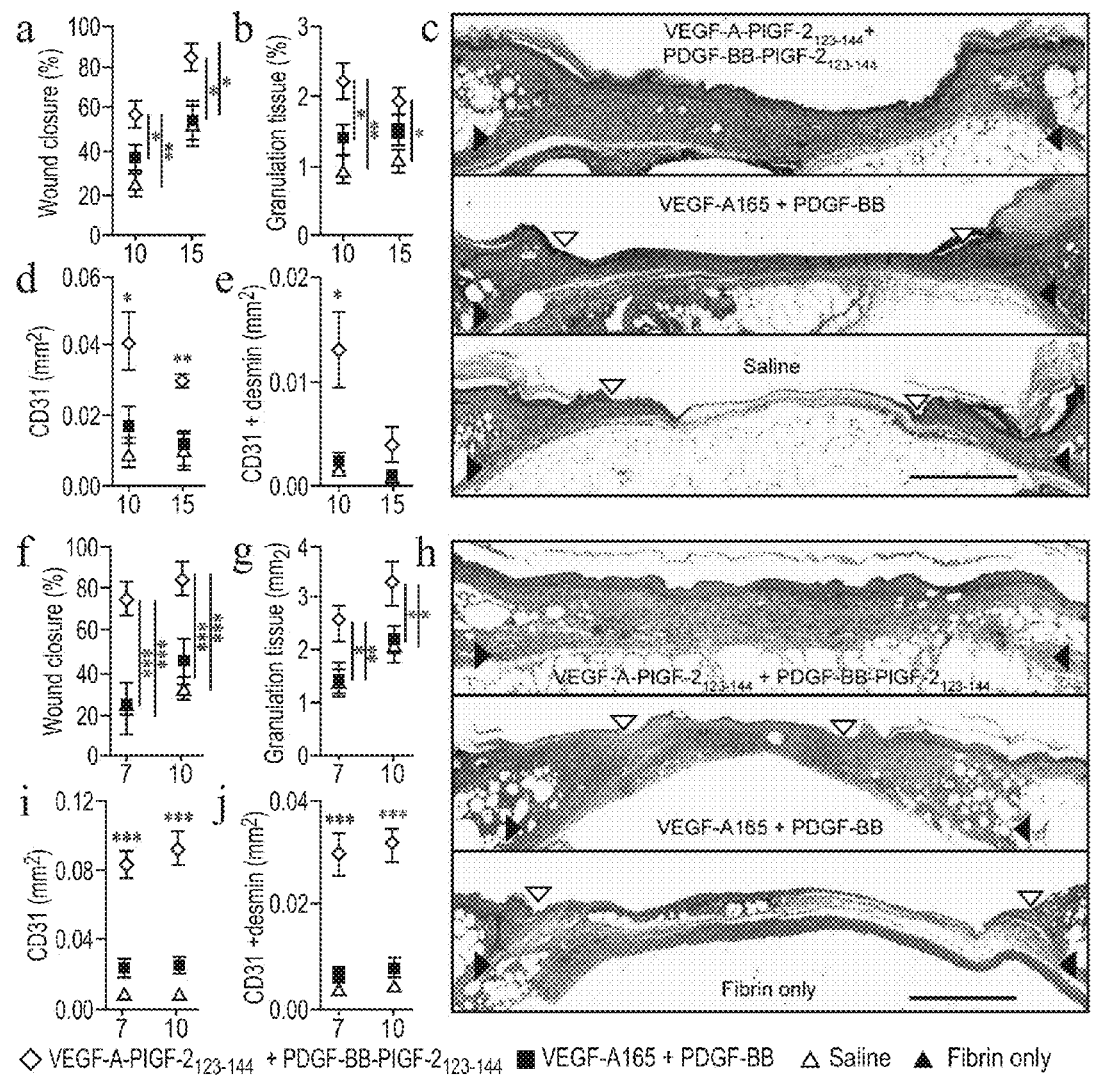

FIG. 7: VEGF-A-PlGF2$_{123-144}$ and PDGF-BB-PlGF2$_{123-144}$ induce greater skin wound healing and angiogenesis than wildtype VEGF-A and PDGF-BB. (a-j) Delivering low doses (200 ng of each, combined) of VEGF-A-PlGF2$_{123-144}$ and PDGF-BB-PlGF2$_{123-144}$ promoted skin-wound healing in diabetic mice, while the same doses of wild-type VEGF-A165 and PDGF-BB did not. Full-thickness back-skin wounds (6 mm diameter) were treated with GFs delivered topically (at day 0, 3, and 6 for wounds analyzed at day 10; at day 0, 3, 6, and 9 for wounds analyzed at day 15) or delivered once in a fibrin matrix. Six different groups were tested: topically, PBS vehicle only, VEGF-A165+PDGF-BB, and VEGF-A-PlGF2$_{123-144}$+PDGF-BB-PlGF2$_{123-144}$; in fibrin, fibrin only, fibrin containing VEGF-A165+PDGF-BB, and fibrin containing VEGF-A-PlGF2$_{123-144}$+PDGF-BB-PlGF2$_{123-144}$. After 10 and 15 days (topical groups; a-b), or 7 and 10 days (fibrin groups; f-g), wound closure and granulation tissue formation were evaluated by histology. All points are mean±SEM (n=8-10 wounds per group per time point. Student's t-test; *p<0.05, p<0.01, *p<0.001. (c,h) Representative histology at 10 days for the fibrin groups and at 15 days for the topical groups (hematoxylin and eosin staining). Black arrows indicate wound edges; red arrows indicate tips of healing epithelium tongue. The granulation tissue, stained in pink-violet. Muscle under the wounds is stained in pink-red. Scale bar=1 mm. (d,e,i,j) Quantification of the angiogenesis within the granulation tissue. After 10 and 15 days (topical groups; d,e), or 7 and 10 days (fibrin groups; I,J), wound tissues were stained for ECs (CD31$^+$ cells) and SMCs (desmin$^+$ cells); dual staining indicates stable vascular morphology (n≥4 per time point, mean±SEM). Wild-type GFs were compared to PlGF2$_{123-144}$-fused GFs using the Student's t-test; *p<0.05, p<0.01, *p<0.001.

Figure 8:
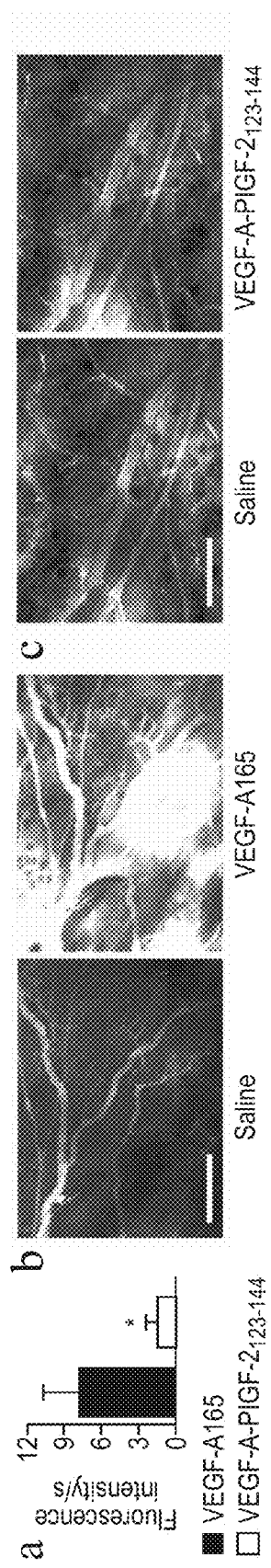

FIG. 8: VEGF-A-PlGF2$_{123-144}$ induces much less vascular permeability than the same dose of wild-type VEGF-A165 (10 µg). (a) The graphs show measurement of vascular permeability in the mouse ear skin. n≥4, mean±SEM. For statistical comparisons, VEGF-A165 was compared to VEGF-A-PlGF2$_{123-144}$ using non-parametric Mann-Whitney U test; *p<0.05. (b,c) Representative images of the mouse ear skin vasculature 20 min after VEGF-A application. Permeability induced by VEGF-A is visualized by the red-labeled dextran leaking from the vessels. Scale bar=0.2 mm.

Figure 9:
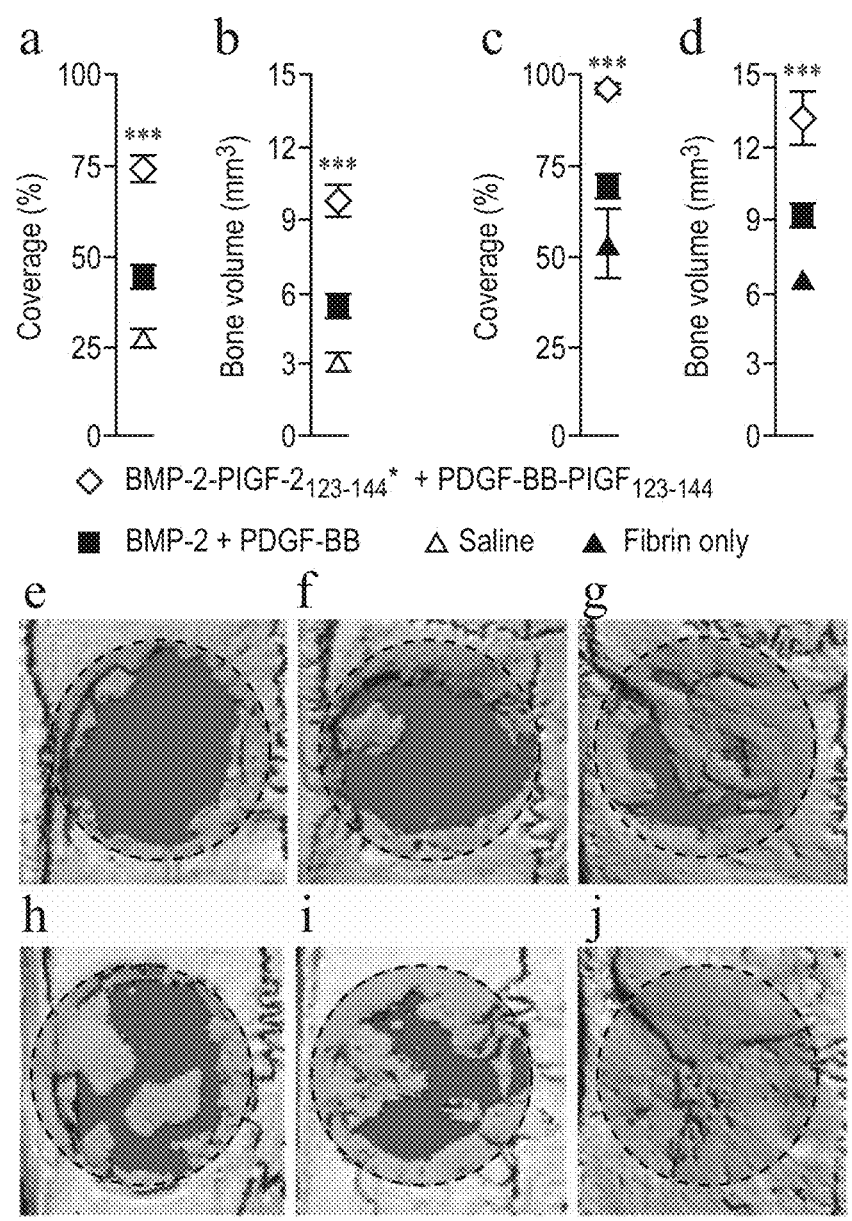

FIG. 9: Delivering PDGF-BB-PlGF2$_{123-144}$ and BMP-2-PlGF2$_{123-144*}$ induce greater bone regeneration in the rat than wild-type PDGF-BB and BMP-2. Critical-size calvarial defects (6 mm diameter) were treated with GFs delivered topically or in a fibrin matrix. Six different groups were tested: topically, saline vehicle only, BMP-2+PDGF-BB, and BMP-2-PlGF2$_{123-144}$*+PDGF-BB-PlGF2$_{123-144}$; and in fibrin, fibrin only, fibrin containing BMP-2+PDGF-BB, and fibrin containing BMP-2-PlGF2$_{123-144}$*+PDGF-BB-PlGF2$_{123-144}$. The doses were 1 µg of each GF, combined, for the groups treated topically to the dura and 200 ng of each GF, combined, for the groups with fibrin. (a-d) Four weeks after treatment, bone repair was measured by µCT as bone volume and coverage of the defect (a,b show groups topical groups; c,d show fibrin groups). (e-j) Representative calvarial reconstructions. e, saline vehicle; f, BMP-2+PDGF-BB; g, BMP-2-PlGF2$_{123-144}$*+PDGF-BB-PlGF2$_{123-144}$; h, fibrin only, i, fibrin with BMP-2+PDGF-BB; j, fibrin with BMP-2-PlGF2$_{123-144}$*+PDGF-BB-PlGF2$_{123-144}$). The defect area is shaded. Data are means±SEM (n=6 per condition). For statistical comparisons, wild-type GFs were compared to PlGF2$_{123-144}$-fused GFs using the Student's t-test; p<0.01, * p<0.001.

DETAILED DESCRIPTION

As reported herein, it has been discovered that placenta growth factor (PlGF) exhibits specific binding activity towards ECM. Aspects of the invention include PlGF polypeptides, molecular fusions of PlGF for delivery of biologics, biomaterials incorporating PlGFs, and drug delivery. The PlGF polypeptides may include or be limited to, e.g., one or more domains or fragments of PlGF.

Fibronectin

Fibronectin (FN) is widely expressed by multiple cell types and is critically important in many ECM-dependent (Krammer A, et al., 2002) processes in the vertebrate, by playing important roles in cell adhesion, migration, growth and differentiation (Mao Y and Schwarzbauer J E, 2005; Pankov R and Yamada K M, 2002). FN is a dimeric glycoprotein composed of two nearly identical 230-270 kDa subunits linked covalently near their C-termini by a pair of disulfide bonds. Each subunit consists of three types of repeating modules, type I, II and III. These modules comprise functional domains that mediate interactions with other ECM components, with cell surface receptors and with FN itself. FN contains 12 type I repeats, 2 type II repeats and 15-18 type III repeats. FN can be subdivided into two forms, soluble plasma FN (abundant soluble constituent of plasma [300 μg/mL]) and less-soluble cellular FN. Plasma FN is secreted by hepatocytes and enriched in blood whereas cellular FN is secreted by fibroblasts and many other cell types and is incorporated into a fibrillar matrix at the cell surface. Cellular FN consists of a much larger and more heterogeneous group of FN isoforms that result from cell-type specific splicing patterns producing FNs with different cell-adhesive, ligand-binding, and solubility properties that provide a mechanism for cells to precisely alter the composition of the ECM in a developmental and tissue-specific manner.

FN is a ligand for several members of the integrin receptor family. The most well studied recognition sequence, the tripeptide RGD, is located in the $10^{th}$ type III repeat (FN III10). The recognition of this simple tripeptide sequence is complex and depends on flanking residues, its three dimensional presentation and individual features of the integrin-binding pockets. For example, a second site in the $9^{th}$ type III repeat (FN III9), the "synergy site" comprising the pentapeptide PHSRN (SEQ ID NO:50) (Mardon H J and Grant K E, 1994), promotes specific α5β1 integrin binding to FN and in FN III9-10, via interactions with the α5 subunit (Mould A P, et al., 1997) whereas αvβ3 integrin binding to RGD is independent of the synergy site (Danen E H, et al., 1995). Integrin α5β1 is the initial receptor mediating assembly of FN in fibrillar matrix formation (Mao Y and Schwarzbauer J E, 2005; Pankov R and Yamada K M, 2002).

In addition to integrin binding, FN also binds cytokines. The second heparin binding domain of FN (FN III12-14) binds most growth factors (cytokines capable of stimulating cellular growth) from the platelet-derived growth factor and fibroblast growth factor families, and some growth factors from the transforming growth factor beta and neurotrophin families (Martino M M and Hubbell J A, 2010).

Although FN molecules are the product of a single gene, the resulting protein can exist in multiple forms that arise from alternative splicing of a single pre-mRNA that can generate as many as 20 variants in human FN. A major type of splicing occurs within the central set of type III repeats (FN III7 to FN III15). Exon usage or skipping leads to inclusion or exclusion of either of two type III repeats—EDB (also termed EIIIB or EDII and located between FN repeats III7 and III8) and EDA (also called EIIIA or EDI and located between FN repeats III11 and III12). The alternatively spliced EDA and EDB domains are almost always absent from plasma FN. Binding of $α_4β_1$ as well as $α_9β_1$ to an EDGIHEL sequence (SEQ ID NO: 51) located within the alternatively spliced EDA segment has been reported, suggesting a possible adhesive function for the increased EDA-containing FN species. FN EDA has been explored as a platform for subunit vaccines. Based on the observation that FN EDA ligates and activates Toll-like receptor 4 (TLR4), one research group has explored using FN EDA as an adjuvant DAMP in subunit vaccines, generating the fusion protein FN III EDA-antigen (Lasarte J J, et al., 2007). A fusion protein containing EDA and the MHC I epitope SIINFEKL (SEQ ID NO: 63) derived from ovalbumin at the C-terminus as well as a fusion protein containing EDA and the full ovalbumin improved ovalbumin presentation by DCs and induced cytotoxic response in vivo. These EDA recombinant proteins were shown to protect mice from a challenge with tumor cells expressing ovalbumin. In spite of a useful effect of FN EDA in recombinant subunit vaccines, the adjuvancy of FN EDA has not been adequate to confer protection in viral challenge models in the mouse (Mansilla C, et al., 2009). Indeed, a combination with another adjuvant, poly(I:C), and anti-CD40 was needed to downregulate intrahepatic expression of hepatitis virus RNA. As such, FN EDA has been found to be insufficiently potent for the arts of vaccinology.

Tenascin C

Tenascin C (TNC) is a large multifunctional extracellular matrix glycoprotein that is present during development and re-expressed in adult life in the case of tissue remodeling, such as wound healing (Trebaul A, et al., 2007), cancer (Orend G, 2005), and inflammation (Udalova I A, et al., 2011). During development, tenascin C plays a highly restricted and dynamic role in the patterning of the neural and vascular networks and the skeleton. It has shown to affect cell adhesion, proliferation, and migration via direct interaction with cells or indirectly through binding to other extracellular matrix molecules, such as fibronectin (Jones F S and Jones P L, 2000).

In a healthy adult organism, tenascin C is produced in a tightly controlled, rapid, and transient manner and contained to specific locations where tissue repair, such as wound healing and nerve regeneration (Joester A and Faissner A, 2001), is necessary and infection needs to be resolved (Udalova I A, et al., 2011). However, in the case of uncontrolled tenascin C production, this molecule becomes pathological resulting in abnormal tissue growth, such as cancer, restenosis after percutaneous coronary angioplasty (Imanaka-Yoshida K, et al., 2001) and stent implantation, fibrotic diseases, chronic wounds, cardiovascular diseases (Golledge J, et al., 2011), and autoimmune diseases (Udalova I A, et al., 2011). Recently, tenascin C has been linked to cardiac and arterial injury, tumor angiogenesis and metastasis (O'Connell J T, et al., 2011; Oskarsson T, et al., 2011), as well as in modulating stem cell behavior (Midwood K S, et al., 2011). In the case of cancer metastasis, it has been shown that cancer cells, responsible for metastasis, produce tenascin C, with inhibition of this tenascin C production resulting in reduced metastasis (Oskarsson T, et al., 2011). Therefore, tenascin could be an important target in the development of diagnostic and therapeutic treatments, especially when particular functions in this large molecule can be defined and localized to a narrowed, specific region.

Human tenascin C is a disulfide-bonded hexabranchion containing 4 major domains: First, an assembly domain at the N-terminal forms a coiled coil structure and interchain disulfide bonds that mediates the hexamer formation. Second, a series of 14.5 epidermal growth factor-like repeats, which are between 30 and 50 amino acids long and each contain six cysteines, have shown to obtain anti-adhesive properties. Third, a series of 15 fibronectin type III repeats, which are approximately 90 amino acids long and form two sheets of antiparallel beta-strands, contain several integrin binding regions (Jones F S and Jones P L, 2000). Fourth, a fibrinogen like globular domain is located at the C terminal (Midwood K S, et al., 2011; Udalova I A, et al., 2011). This fibrinogen-like globular domain has been shown to agonize TLR4 (Midwood K, et al., 2009). As such, this domain is a signal of danger to the body and initiates immunological reactions.

The fibronectin type III domain region of tenascin has shown a large variability due to alternative splicing depending on the TNC source (Jones F S and Jones P L, 2000). The numbers (x-y) of fibronectin type III domains of TNC will be defined in this report as TNC IIIx-y. Domain TNC III3 (Peng Q, et al., 2009) contains an RGD peptide and multiple integrin binding domains (for example: $\alpha_v\beta_3$, $\alpha_9\beta_1$, $\alpha_3\beta_6$, $\alpha_8\beta_1$ (Yokosaki Y, et al., 1998), $\alpha_v\beta_1$, $\alpha_8\beta_1$) (for a large variety of cell types (for example: smooth muscle cells, endothelial cells, neurons, astrocytes, glioma) (Jones F S and Jones P L, 2000). Domain TNC III5 has demonstrated to bind heparin (Weber P, et al., 1995). As reported herein, the domain TNC III5, and longer domains comprising the TNC III5 domain such as TNC III1-5 and TNC III3-5, have been shown to bind chemokines.

Fibrinogen and Fibrin

Fibrinogen is a soluble plasma glycoprotein that is synthesized by the liver and the precursor protein during blood coagulation. The proteolytic enzyme thrombin, coagulation factor II, will polymerize fibrinogen into fibrin during coagulation by cleaving fibrinopeptides from its central domain, preventing physicochemical self-assembly or polymerization of the molecule (Weisel J W, 2007). Fibrin is sequentially chemically cross-linked by factor XIIIa forming the primary structural protein of a viscoelastic blood clot (Mosesson M W, 2005), and functioning as a specialized provisional protein network that is formed principally in spontaneous tissue repair. The stability of fibrin depends on its interplay with molecular/cellular components of the hemostatic system (Hantgan R R, et al., 1994). In addition to cross-linking fibrin to itself, factor XIIIa cross-links other adhesive proteins into the blood clot. Fibrin can bind several cell-adhesion receptors such as integrins and notably promotes the adhesion of platelet and leukocytes such as monocytes and neutrophils (Flick M J, et al., 2004; Ugarova T P and Yakubenko V P, 2001).

Fibrin matrices were one of the first biomaterials used to prevent bleeding and promote wound healing (Janmey P A, et al., 2009). Fibrin is available from autologous sources and from cryoprecipitated pooled human blood plasma. Today, fibrin is one of the most used hydrogel in the clinic. The complex fibril structure and cross-linked character of fibrin matrix can be controlled by the details of its formation (Lorand L and Graham R M, 2003; Standeven K F, et al., 2007; Weisel J W, 2004). Importantly, in contrast to fibrillar collagen matrices where cell migration occurs both through mechanisms that are dependent and independent of proteolytic degradation, cell migration in fibrin is almost exclusively dependent upon cell-associated proteolytic activity (essentially from plasmin and matrix metalloproteinases (Mosesson M W, 2005)). One of the main advantages of fibrin is that several proteins are naturally incorporated into fibrin matrix during the coagulation such as fibronectin and alpha-2-plasmin inhibitor, by covalent cross-linking via the transglutaminase factor XIIIa (Mosesson M W, 2005). Therefore, this natural reaction can be easily exploited to functionalize fibrin with multiple cell-signaling molecules (Patterson J, et al., 2010; Schense J C and Hubbell J A, 1999). In addition, fibrinogen is known to possess specific interactions with fibroblast growth factor (FGF)-2, VEGF-A165 and insulin-like growth factor binding protein (IG-FBP)-3 (Peng H, et al., 2004; Sahni A, et al., 1998; Sahni A, et al., 2006; Werner S and Grose R, 2003).

Fibrin is a useful base matrix, and heparin binding peptides and molecular fusions described herein may be used with the same. Other materials may also be engineered to include TG or moieties that interact with transglutaminases to receive a TG molecular fusion. U.S. Pat. Nos. 7,241,730, 6,331,422, U.S. Pat. No. 6,607,740, U.S. Pat. No. 6,723,344, US Pub 2007/0202178, US Pub 2007/0264227 are hereby incorporated herein by reference for all purposes; in case of conflict, the specification is controlling.

Fibrin matrices are subject to degradation by proteases in vivo, and protease inhibitors are frequently formulated in fibrinogen/fibrin matrixes to prolong their lifetime in vivo. This renders the fibrin matrices more useful in applications of tissue adhesives and sealants, and in applications of tissue engineering. One such protease inhibitor is aprotinin. A fibrin-binding form of aprotinin has been engineered by including a factor XIIIa substrate within a fusion protein comprising aprotinin (Lorentz K M, et al., 2011).

Matrices are useful for purposes of sustained release of drugs. Drugs may be entrapped in the matrix and slowly diffuse from the matrix. Affinity may be engineered between a drug and components of the matrix. For example, affinity for heparin has been used to prolong the release of heparin-binding cytokines from fibrin-based matrices, incorporating binding sites for heparin into the fibrin matrix and employing heparin as an intermediate in that binding interaction (Sakiyama S E, et al., 1999).

Tissue Repair and Regeneration

After damage, tissue repair or regeneration is the result of a spatio-temporal coordination of cell fate processes that are controlled by a multitude of cell-signaling events coming from the extracellular microenvironment and recruited cells at the site of injury (Gurtner G C, et al., 2008). Within a biomechanical context provided by this elastic milieu (Discher D E, et al., 2009), cells adhere by receptor-mediated interactions with extracellular matrix components such as fibronectin and laminin (among many others), mediated by specialized adhesion receptors such as integrins and others (Berrier A L and Yamada K M, 2007). These receptors transmit stress from the extracellular matrix, through the membrane, to the cytoskeleton within the cell in a dynamic and concerted manner (Hinz B, 2009). The adhesion receptors do much more than transmit stress, however; in particular within clusters of adhesion receptors in the membrane, biochemical signal transduction takes place through kinase activation and other mechanisms (Berrier A L and Yamada K M, 2007; Hinz B, 2009). In addition to adhesion proteins, the extracellular matrix also sequesters and presents a number of morphoregulatory molecules including, morphogens, cytokines, and growth factors, which control processes of cell division, and/or migration, and/or differentiation, and/or multicellular morphogenesis (Discher D E, et al., 2009; Schultz G S and Wysocki A, 2009). Morphogens, cytokines, and growth factors are powerful soluble signaling molecules, because they can change cell fate and induce tissue morphogenesis directly. The term morphogen is principally used in developmental biology to describes a particular type of signaling molecule that can induce a cellular response in a concentration-dependent manner (Affolter M and Basler K, 2007), while cytokines and chemokines (small cytokine inducing chemotaxis) are regulatory proteins essential for the development and functioning of both innate and adaptive immune response (Rossi D and Zlotnik A, 2000; Vilcek J and Feldmann M, 2004). By definition growth factors are capable of inducing cell growth, in addition to other cellular response such as migration and differentiation (Cross M and Dexter T M, 1991). A growth factor can be either a morphogen or a cytokine.

For example, key cytokines involved in tissue morphogenesis include vascular endothelial growth factors (VEGFs), platelet derived growth factors (PDGFs), fibroblast growth factors (FGFs), insulin-like growth factors (IGFs), bone morphogenetic proteins (BMPs), transforming growth factors beta (TGF-βs), and neurotrophins (β-NGF, NT-3, BDNF). Many cytokines bind extracellular matrix components such as heparan sulfate proteoglycans (Lindahl U and Li J P, 2009), and reside there until released by enzymatic processes or dissociation. These factors, when released and sometimes also when matrix-bound (Makarenkova H P, et al., 2009), bind to cell-surface receptors and trigger signaling, principally through kinase activation. Thus, the extracellular matrix serves as a reservoir of signaling molecules, both adhesion molecules and cytokines, that instruct cell decision processes. Angiogenesis, multicellular morphogenesis, and stem cell differentiation are cellular processes that are tightly controlled by the extracellular matrix and cytokines, and especially by their cooperative signaling. Because tissue repair is driven by these processes, the function of the extracellular matrix guides the design of biomaterials in tissue engineering and regenerative medicine, with the overall goal of mimicking the following key features: the presentation of adhesion molecules and the release of cytokines.

Vaccinology

As mentioned above, cytokines play a fundamental role in tissue morphogenesis. Cytokines also play a fundamental role in immunology, by regulating proliferation, maturation and migration of different immune cell types, thus driving the appropriate immune response to different types of antigens. The cytokine TGF-β is a particularly important cytokine in immunology.

Chemokines are small proteins that also play fundamental roles in immunology. Among the chemokines, interferon-γ (IFN-γ) is a critical immunomodulatory chemokine for innate and adaptive immunity against viral and bacterial antigens and for tumor control. IFN-γ is mainly expressed by natural killer (NK) and natural killer T-cells (NKT) as part of the innate immune response, and by CD4 and CD8 T cells during the adaptive immune response. IFN-γ is the most important chemokine in regulating the balance between Th1 and Th2 cells: Th1 cells express IFN-γ, which in turn causes Th1 differentiation and Th2 differentiation suppression. The different cellular response to IFN-γ are activated by its binding to an heterodimeric receptor (IFNGR1 and IFNGR2) that activates JAK/STAT1 signaling pathway. The activation of this intracellular signaling triggers the expression of multiple downstream genes, among them the chemokine interferon gamma-induced protein 10 (CXCL10) and chemokine (C-X-X motif) ligand 11 (CXCL11). These two chemokines elicit their effect by binding CXCR3 receptor on the cell surface and are considered potent chemoattractants for monocyte/macrophages, dendritic cells, NK and T-cells, respectively.

In vaccinology, antigens are peptide or protein domains or whole proteins of pathogen or self-origin (Hubbell J A, et al., 2009). Vaccine antigens in infectious diseases are based on proteins found in the pathogens of interest, such as influenza antigens or tuberculosis antigens. The number of antigens targeted in infectious disease, both in prophylactic and therapeutic vaccines, are myriad. Vaccine antigens in cancer are based on proteins found in the tumor cell type, such as the antigen survivin to be highly expressed in many tumor types or the antigen TRP-2 expressed in melanocytes and a target for cancer vaccination in melanoma. The number of antigens targeted in cancer are myriad.

A vaccine may be made that comprises a PlGF2 domain and an antigen, for instance a vehicle or a matrix as described herein. The PlFG2 provides attachment to native tissue or ECM in the matrix. A vaccine composition may comprise adjuvants, danger signals, and/or chemokines, which may be part of a matrix, a molecular fusion that comprises a PlGF2 domain, or may be added in addition to the PlFG2.

PlGF

Peptides that mimic a domain from PlGF2 are described herein. The cytokine PlGF exists in multiple isoforms. PlGF2 is an elongated isoform of PlGF-1, containing an insert of sequence RRRPKGRGKRRREKQRPTDCHL (SEQ ID NO:4) in the human, RRKTKGKRKRSRNSQ-TEEPHP (SEQ ID NO:5) in the mouse, and related sequences in other mammalian species. Herein the unexpected surprising discovery is reported that this peptide binds very strongly to fibrinogen and fibrin, as well as the extracellular matrix proteins fibronectin, vitronectin, osteopontin, tenascin C, and to lesser extent collagen I. This domain is referred to as the $PlGF2_{123-144}$. The term PlGF2 domain is used to refer to this domain and to subdomains that demonstrate specific binding for extracellular matrix. The strong binding between the $PlGF2_{123-144}$ and fibrinogen/fibrin can be used to bind proteins comprising $PlGF2_{123-144}$, including protein drugs and antigens, in fibrin matrices. The strong binding between $PlGF2_{123-144}$ and fibrinogen/fibrin and/or extracellular matrix proteins can be used to prolong the presence of proteins comprising $PlGF2_{123-144}$ that have been administered in fibrin matrices, that have been administered upon or within the site of an injury, or that have been administered upon or within a tissue site. The strong binding between the PlGF2 domain and extracellular matrix proteins can be used to prolong the retention of proteins comprising the PlGF2 domain in tissues by virtue of binding to extracellular matrix endogenously present in the tissue or tissue lesion site. The discovered affinity between $PlGF2_{123-144}$ and fibrinogen/fibrin and the affinity that exists between $PlGF2_{123-144}$ and extracellular matrix molecules leads to a number of preferred embodiments.

The term PlGF2 or PlGF2 domain includes the peptides of SEQ ID NO:4 and 5, and subsequences thereof, as well as the variations of those sequences. SEQ ID NO:4 and 5 are embodiments of a PlGF2 domain. Further embodiments of a PlGF2 domain include conservative substitutions of the sequences and also truncated forms, with N-terminal and/or C-terminal residues being truncated. Identifying truncations can be readily accomplished by the artisan reading the instant disclosure. The number of consecutive residues that provide specific binding is between about 4 and about 15 residues, with longer sequences also showing specific binding. Accordingly, embodiments of PlGF2 include an isolated polypeptide comprising a sequence chosen from the group consisting of SEQ ID NO:4 having from 0 to 5 conservative substitutions, SEQ ID NO:5 having from 0 to 5 conservative substitutions, and subsequences thereof, said subsequences exhibiting specific binding to one or more of: fibrinogen, fibronectin, vitronectin, tenascin C, osteopontin, and fibrin.

The subsequences include all subsequences of 4 to 15 residues in length, e.g., all 4, 5, 6, and 7-residue subsequences, and all 7-12 and all 5-15 residue subsequences. The value of the dissociation constant for the sequences is low, e.g., wherein the specific binding of the polypeptide to fibrinogen has a dissociation constant ($K_D$) of less than about 40 nM. Moreover, the substitution of L-amino acids in the discovered sequence with D-amino acids can be frequently accomplished, as in Giordano.

Figure 2:
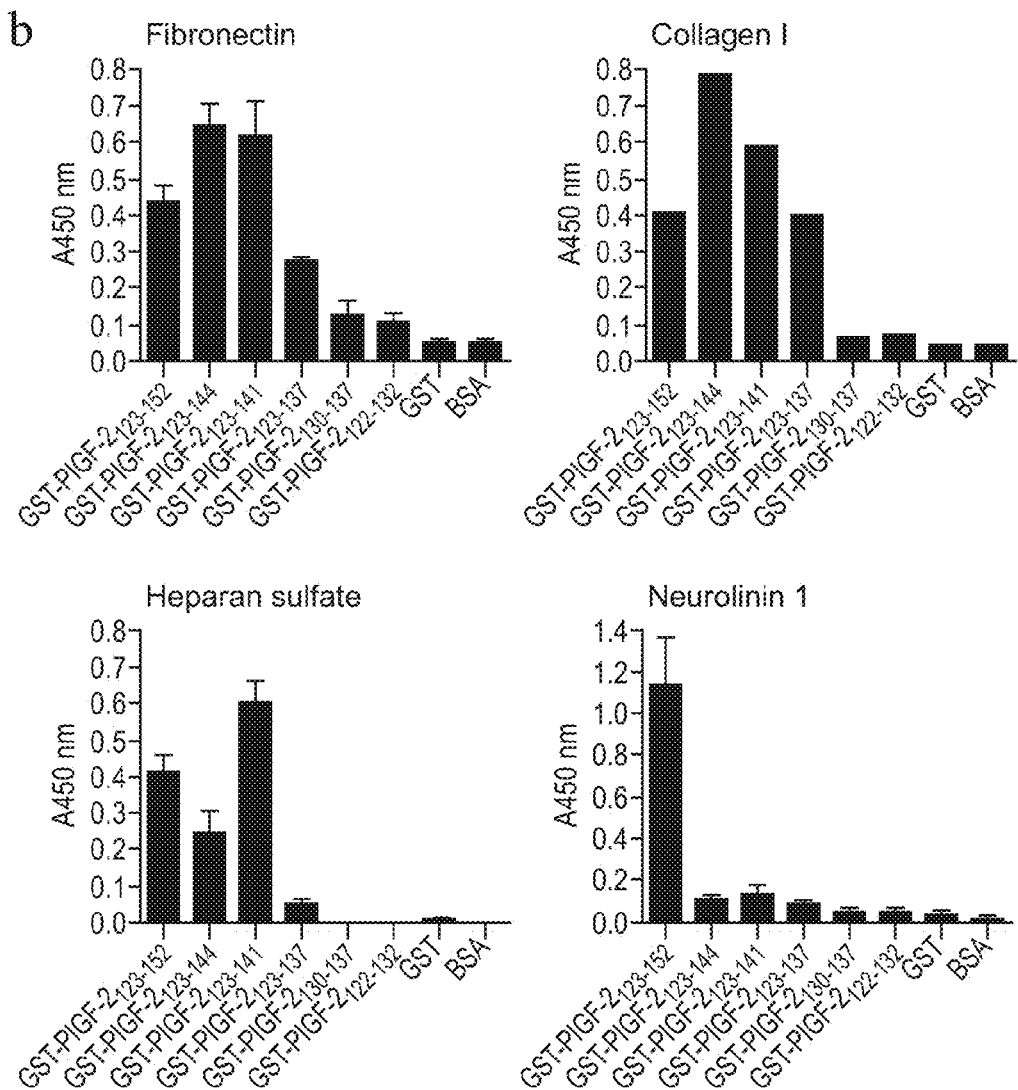

Referring to FIG. 2, panel a, data for the testing subsequences of the PlGF2$_{123-152}$ showed that fragments of 7 residues retained specific binding for extracellular matrix (ECM). The larger fragments, however, showed higher affinity. This data indicates that even shorter sequences can reasonably be expected to show specific binding to appropriate ECM, including all subsequences of four or more residues. Further, many sequences in the biological arts are known to be effective when they are part of even very large molecules, e.g., the RGD cell adhesion motif. Even though some molecules will fold in a way that confounds the specific binding of such relatively small sequences, artisans are very familiar with techniques for creating even very large molecules that employ such sequences in an effective manner. On the other hand, there are a certain number of natural biomolecules that may have one or more such sequences occurring as a result of random chance, considering that there are many natural biomolecules and only about 20 natural amino acids. Such sequences should not be assumed to be active for specific binding because such biomolecules have been evolutionarily tuned to accomplish specific functions. Binding to ECM is a very important naturally-occurring, specific function that should not be attributed to particular biomolecules without suitable biological evidence in such instances.

Most adhesion binding motifs can undergo some conservative substitutions and retain functionality. Although not all such substitutions will be effective, such changes are often effective. There are a variety of conservative changes that can generally be made to an amino acid sequence without altering activity. These changes are termed conservative substitutions or mutations; that is, an amino acid belonging to a grouping of amino acids having a particular size or characteristic can be substituted for another amino acid. Substitutes for an amino acid sequence may be selected from other members of the class to which the amino acid belongs. For example, the nonpolar (hydrophobic) amino acids include alanine, leucine, isoleucine, valine, proline, phenylalanine, tryptophan, methionine, and tyrosine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Such alterations are not expected to substantially affect apparent molecular weight as determined by polyacrylamide gel electrophoresis or isoelectric point. Conservative substitutions also include substituting optical isomers of the sequences for other optical isomers, specifically D amino acids for L amino acids for one or more residues of a sequence. Moreover, all of the amino acids in a sequence may undergo a D to L isomer substitution. Exemplary conservative substitutions include, but are not limited to, Lys for Arg and vice versa to maintain a positive charge; Glu for Asp and vice versa to maintain a negative charge; Ser for Thr so that a free —OH is maintained; and Gln for Asn to maintain a free $NH_2$. Moreover, point mutations, deletions, and insertions of the polypeptide sequences or corresponding nucleic acid sequences may in some cases be made without a loss of function of the polypeptide or nucleic acid fragment. Substitutions may include, e.g., 1, 2, 3, or more residues. The amino acid residues described herein employ either the single letter amino acid designator or the three-letter abbreviation. Abbreviations used herein are in keeping with the standard polypeptide nomenclature, J. Biol. Chem., (1969), 243, 3552-3559. All amino acid residue sequences are represented herein by formulae with left and right orientation in the conventional direction of amino-terminus to carboxy-terminus. Accordingly, conservative substitutions of the peptides set forth herein are contemplated and may be described in terms of quantity, e.g., 1 to 5, or percent, e.g., 0% to 33%. Artisans will immediately appreciate that all values and ranges within the expressly stated limits are contemplated, e.g., about 5%, 7 about %, or about 15%. In the case of 1 substitution in 7 residues, the substitution is 14.2%, which is about 15%. In the case of 2 substitutions in 22, the percentage is 9.1, which is about 10%.

Certain embodiments provide various polypeptide sequences and/or purified or isolated polypeptides. A polypeptide is a term that refers to a chain of amino acid residues, regardless of post-translational modification (e.g., phosphorylation or glycosylation) and/or complexation with additional polypeptides, synthesis into multisubunit complexes, with nucleic acids and/or carbohydrates, or other molecules. Proteoglycans therefore also are referred to herein as polypeptides. As used herein, a “functional polypeptide” is a polypeptide that is capable of promoting the indicated function. Polypeptides can be produced by a number of methods, many of which are well known in the art. For example, polypeptides can be obtained by extraction (e.g., from isolated cells), by expression of a recombinant nucleic acid encoding the polypeptide, or by chemical synthesis. Polypeptides can be produced by, for example, recombinant technology, and expression vectors encoding the polypeptide introduced into host cells (e.g., by transformation or transfection) for expression of the encoded polypeptide.

In some cases a determination of the percent identity of a peptide to a sequence set forth herein may be required. In such cases, the percent identity is measured in terms of the number of residues of the peptide, or a portion of the peptide. A polypeptide of, e.g., 90% identity, may also be a portion of a larger peptide The term purified as used herein with reference to a polypeptide refers to a polypeptide that has been chemically synthesized and is thus substantially uncontaminated by other polypeptides, or has been separated or purified from other most cellular components by which it is naturally accompanied (e.g., other cellular proteins, polynucleotides, or cellular components). An example of a purified polypeptide is one that is at least 70%, by dry weight, free from the proteins and naturally occurring organic molecules with which it naturally associates. A preparation of the a purified polypeptide therefore can be, for example, at least 80%, at least 90%, or at least 99%, by dry weight, the polypeptide. Polypeptides also can be engineered to contain a tag sequence (e.g., a polyhistidine tag, a myc tag, or a FLAG® tag) that facilitates the polypeptide to be purified or marked (e.g., captured onto an affinity matrix, visualized under a microscope). Thus a purified composition that comprises a polypeptide refers to a purified polypeptide unless otherwise indicated. The term isolated indicates that the polypeptides or nucleic acids of the invention are not in their natural environment. Isolated products of the invention may thus be contained in a culture supernatant, partially enriched, produced from heterologous sources, cloned in a vector or formulated with a vehicle, etc.

Polypeptides may include a chemical modification; a term that, in this context, refers to a change in the naturally-occurring chemical structure of amino acids. Such modifications may be made to a side chain or a terminus, e.g., changing the amino-terminus or carboxyl terminus. In some embodiments, the modifications are useful for creating chemical groups that may conveniently be used to link the polypeptides to other materials, or to attach a therapeutic agent.

Specific binding, as that term is commonly used in the biological arts, refers to a molecule that binds to a target with a relatively high affinity compared to non-target tissues, and generally involves a plurality of non-covalent interactions, such as electrostatic interactions, van der Waals interactions, hydrogen bonding, and the like. Specific binding interactions characterize antibody-antigen binding, enzyme-substrate binding, and specifically binding protein-receptor interactions; while such molecules may bind tissues besides their targets from time to time, such binding is said to lack specificity and is not specific binding.

Discussion

Example 1 (see FIG. 1) describes results establishing that the domain $PlGF2_{123-144}$ was discovered within PlGF2 that strongly and promiscuously binds ECM proteins. This domain is only a part of PlGF2 and, as such, does not exist in nature. PlGF2 strongly bound all ECM proteins tested (FIG. 1, gray bars). Alignment of the protein sequences of the splice variants PlGF2 and PlGF-1 (which does not bind) illustrates how PlGF2 contains an additional 21 amino-acid insert ($PlGF2_{123-144}$, in gray) located near the C-terminus. Binding was also shown to be effective when the PlGF2 domain was fused to a protein, GST ($GST-PlGF2_{123-144}$). From Example 1, it was concluded that $PlGF2_{123-144}$ comprises a ECM protein binding domain. The binding of various PLGF2 fragments to various ECM proteins, heparan sulfate, and neuropilin-1 was tested, with the results depicted in FIG. 2. Example 2 details the experiments as well as describing examples of making truncations and/or substitutions into the sequence.

Figure 3:
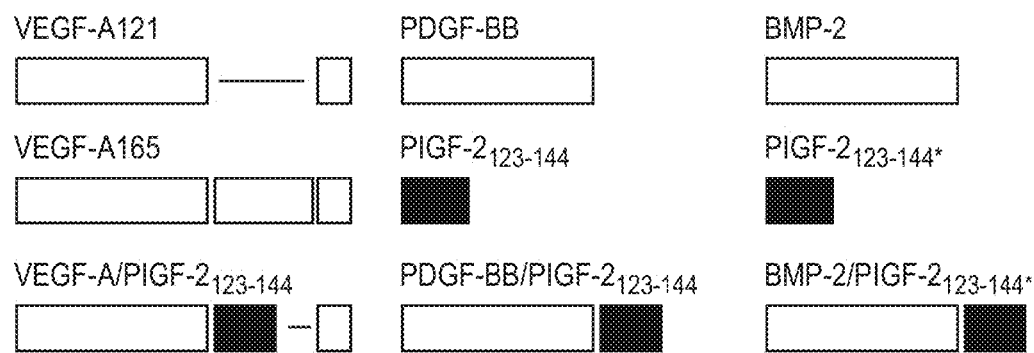
Figures 1, 4:
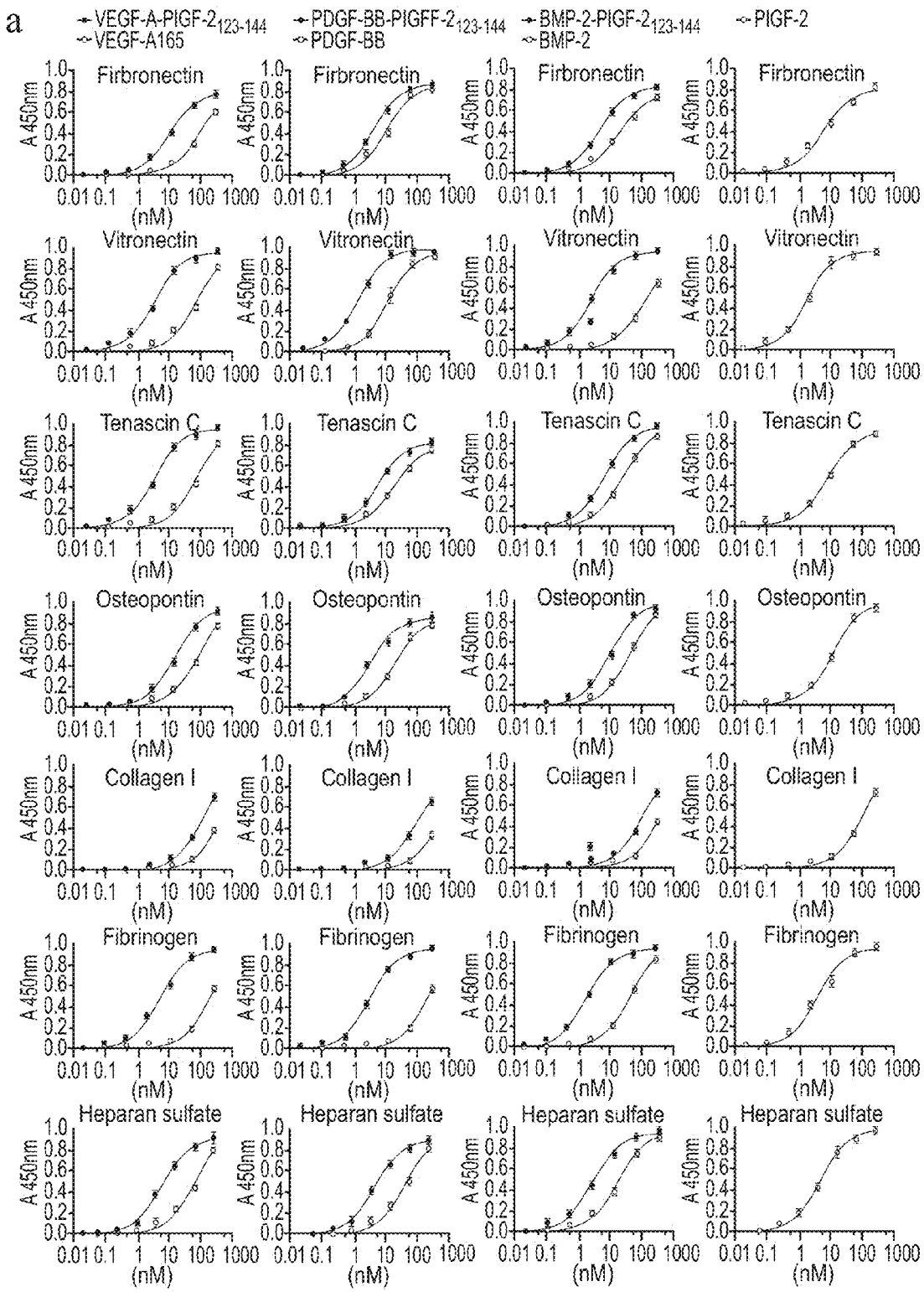
Figures 2, 4:
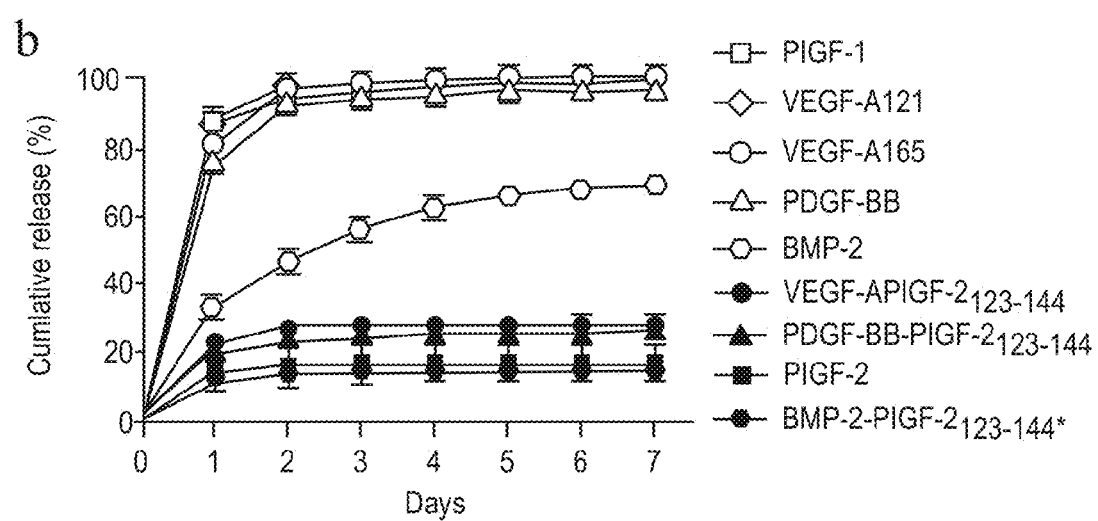

A variety of cytokines were made as fusion proteins with the PlGF2 domain (Example 3; FIG. 3). FIG. 4 (see Example 4) sets forth results for the binding of such fusion proteins with ECM. The dissociation constants for the specific binding were measured and it was determined that the affinity of PlGF2 for a wide variety of ECM proteins was conferred upon the fusion molecules. These included Vascular endothelial growth factor (VEGF), Platelet-derived growth factor (PDGF), and Bone morphogenetic protein (BMP). Example 5 details the further manufacture of cytokine-PlGF2 domain molecular fusions, including fusions with Insulin Growth Factor-I (IGF-I), Transforming Growth Factor beta 1 (TGF-β1), TGF-beta 2 (TGF-β2), Brain-derived neurotrophic factor (BDNF), and a neurotrophin (NT), NT-3. These biological factors were observed (Example 6, FIG. 5) to maintain their biological activity in when fused to the PlGF2 domain. In fact the VEGF fusion molecule had increased activity.

There is a major problem that has arisen in translating VEGF-A to clinical use. Indeed, while VEGF-A activation of VEGF-receptor 2 (VEGF-R2) is potentially a powerful approach to promote angiogenesis, actual administration of VEGF-A has been shown to rapidly induce vascular permeability, which leads to systemic hypotension and edema; this phenomenon has been the dose-limiting toxic response in peripheral and cardio-vascular applications (Simons M and Ware J A, 2003) and presents serious issues in regenerative medicine. It was theorized that combining VEGF and a PlGF2 domain would not affect the potency of the VEGF but would cause it to be released more slowly so that vascular permeability would be lessened and the combination would be more effective than the VEGF by itself. Similarly, the fusion of various cytokines to the PlGF2 domain is similarly theorized to be effective. These theories were supported in a series of experiments. Example 7 (FIG. 6) details how various ECM super-affinity cytokine variants were created that bind to, and are retained by, ECM molecules in vivo. Example 8 (FIG. 7) used clinically important models to test the healing power of molecular fusions of PDGF-BB and VEGF-A with a PlGF2 domain. Wounds treated with the engineered molecular fusions of PDGF-BB and VEGF-A led to significantly faster wound closure, and improved healing was corroborated by observing better granulation tissue and biomarkers (CD31 and desmin) that showed improved angiogenesis.

Further, the molecular fusion of VEGF and a PlGF2 domain was observed to cause much less vascular permeability despite causing these improved results. Example 9 (FIG. 8) details the results. In brief, the fusion molecule appeared to decouple angiogenesis from hyper-permeability.

In light of these various results showing that the PlGF2 domains could create a desired specific binding in a fusion molecule without disrupting cytokine functions, further tests were conducted to demonstrate the general applicability of such combinations. Example 10 (FIG. 9) details the treatment of bone defects with molecular fusions of cytokines with a PlGF2 domain. In these experiments, a matrix was used to retain and controllably deliver the molecular fusions. In brief, the fusion molecules were much more effective than the cytokines by themselves, and much lower doses were effective (nanograms of the fusion molecule compared to micrograms of the unaltered cytokines). These results demonstrate the effectiveness of a matrix that specifically binds the molecular fusions as well as their effectiveness in a bone healing treatment.

A variety of detailed Examples are further provided that describe how to design and make various molecular fusions. Example 11 details how cell adhesion motifs may be fused to a PlGF2 domain. A fibronectin domain is used as an example. Matrices for delivery drugs and/or promoting cell invasion or healing can be exposed to such molecular fusions to and be modified to carry a drug or other bioactive agent such as a cell adhesion motif. Various matrices are known, including synthetic matrices, fibrin matrices, and natural or synthetic matrices, including those that are covalently crosslinked and those that are not covalently crosslinked. Example 12 details a molecular fusion of a drug for release from a matrix, with Parathyroid Hormone Fragment 1-34 used as an example. Example 13 details a molecular fusion of a PlGF2 domain and a protease inhibitor. The context is a fibrin matrix with aprotinin as an example. Example 14 details a molecular fusion of the chemokines CXCL10, CXCL11, IFN-γ, and CCL21 with PlGF2.

Vaccines may also be made using a PlGF2 domain. Example 15 details the molecular fusion of an immunogenic antigen with a PlGF2 domain. This molecule may be administered in the context of a pharmaceutically acceptable compound and in combination with other features for vaccines, e.g., as detailed elsewhere herein. For instance, Example 16 provides details for engineering the Toll-like receptor agonist fused with a PlGF2 domain.

Drug-delivery and controlled release is generally exemplified by the details of Example 17, which describes a molecular fusion of a bioactive agent with a PlGF2 domain.

For instance, the an extracellular matrix-binding FGF18 is provided by a fusion protein between FGF18 and a PlGF2 domain. Various alternatives for this fusion are presented.

Molecular Fusion

A preferred embodiment is a molecular fusion between a PlGF2 domain and a therapeutic agent. Embodiments include a PlGF2 domain in a molecular fusion with, e.g., a therapeutic agent, marker, cell adhesion molecule, antigen, protein, protein drug, or cytokine. A molecular fusion may be formed between a first PlGF2 peptide and a second peptide. Instead of second peptide a chemical moiety may be used, e.g., a marker, fluorescent marker. The fusion comprises the peptides conjugated directly or indirectly to each other. The peptides may be directly conjugated to each other or indirectly through a linker. The linker may be a peptide, a polymer, an aptamer, a nucleic acid, or a particle. The particle may be, e.g., a microparticle, a nanoparticle, a polymersome, a liposome, or a micelle. The polymer may be, e.g., natural, synthetic, linear, or branched. A fusion protein that comprises the first peptide and the second peptide is an example of a molecular fusion of the peptides, with the fusion protein comprising the peptides directly joined to each other or with intervening linker sequences and/or further sequences at one or both ends. The conjugation to the linker may be through covalent bonds. Methods include preparing a molecular fusion or a composition comprising the molecular fusion, including such a composition in a pharmaceutically acceptable form.

Embodiments include a molecular fusion of a polypeptide that comprises a PlGF2 domain and a transglutaminase substrate (TG). An embodiment of a TG substrate is a peptide that comprises residues 1-8 of alpha 2-plasmin inhibitor (NQEQVSPL) (SEQ ID NO:50). Embodiments include such a polypeptide being a recombinant fusion polypeptide. The molecular fusion may be further comprising a cell adhesion moiety having a specific binding affinity for a cell adhesion molecule. Various cell adhesion moieties are known, for instance, wherein the cell adhesion moiety comprises a ligand for a glycoprotein or a cell surface receptor. Or the cell adhesion moiety may comprise a ligand with specific binding to the cell adhesion molecule and the cell adhesion molecule is a cell surface receptor chosen from the group consisting of an integrin, and a cadherin.

The term molecular fusion, or the term conjugated, refers to direct or indirect association by chemical bonds, including covalent, electrostatic ionic, or charge-charge. The conjugation creates a unit that is sustained by chemical bonding. Direct conjugation refers to chemical bonding to the agent, with or without intermediate linkers or chemical groups. Indirect conjugation refers to chemical linkage to a carrier. The carrier may largely encapsulate the agent, e.g., a polymersome, a liposome or micelle or some types of nanoparticles, or have the agent on its surface, e.g., a metallic nanoparticle or bead, or both, e.g., a particle that includes some of the agent in its interior as well as on its exterior. The carrier may also encapsulate an antigen for immunotolerance. For instance a polymersome, liposome, or a particle may be made that encapsulates the antigen. The term encapsulate means to cover entirely, effectively without any portion being exposed, for instance, a polymersome may be made that encapsulates an antigen or an agent.

Conjugation may be accomplished by covalent bonding of the peptide to another molecule, with or without use of a linker. The formation of such conjugates is within the skill of artisans and various techniques are known for accomplishing the conjugation, with the choice of the particular technique being guided by the materials to be conjugated. The addition of amino acids to the polypeptide (C- or N-terminal) which contain ionizable side chains, i.e. aspartic acid, glutamic acid, lysine, arginine, cysteine, histidine, or tyrosine, and are not contained in the active portion of the polypeptide sequence, serve in their unprotonated state as a potent nucleophile to engage in various bioconjugation reactions with reactive groups attached to polymers, i.e. homo- or hetero-bi-functional PEG (e.g., Lutolf and Hubbell, *Biomacromolecules* 2003; 4:713-22, Hermanson, *Bioconjugate Techniques*, London. Academic Press Ltd; 1996). In some embodiments, a soluble polymer linker is used, and may be administered to a patient in a pharmaceutically acceptable form. Or a drug may be encapsulated in polymerosomes or vesicles or covalently attached to the peptide ligand.

The molecular fusion may comprise a particle. The PlGF2 domain may be attached to the particle. An antigen, agent, or other substance may be in or on the particle. Examples of nanoparticles, micelles, and other particles are found at, e.g., US 2008/0031899, US 2010/0055189, US 2010/0003338, which applications are hereby incorporated by reference herein for all purposes, including combining the same with a ligand as set forth herein; in the case of conflict, however, the instant specification controls.

Nanoparticles may be prepared as collections of particles having an average diameter of between about 10 nm and about 200 nm, including all ranges and values between the explicitly articulated bounds, e.g., from about 20 to about 200, and from about 20 to about 40, to about 70, or to about 100 nm, depending on the polydispersity which is yielded by the preparative method. Various nanoparticle systems can be utilized, such as those formed from copolymers of poly (ethylene glycol) and poly(lactic acid), those formed from copolymers of poly(ethylene oxide) and poly(beta-amino ester), and those formed from proteins such as serum albumin. Other nanoparticle systems are known to those skilled in these arts. See also Devalapally et al., *Cancer Chemother Pharmacol.*, Jul. 25, 2006; Langer et al., *International Journal of Pharmaceutics,* 257:169-180 (2003); and Tobío et al., *Pharmaceutical Research,* 15(2):270-275 (1998).

Larger particles of more than about 200 nm average diameter incorporating the heparin binding ligands may also be prepared, with these particles being termed microparticles herein since they begin to approach the micron scale and fall approximately within the limit of optical resolution. For instance, certain techniques for making microparticles are set forth in U.S. Pat. Nos. 5,227,165, 6,022,564, 6,090,925, and 6,224,794.

Functionalization of nanoparticles to employ targeting capability requires association of the targeting polypeptide with the particle, e.g., by covalent binding using a bioconjugation technique, with choice of a particular technique being guided by the particle or nanoparticle, or other construct, that the polypeptide is to be joined to. In general, many bioconjugation techniques for attaching peptides to other materials are well known and the most suitable technique may be chosen for a particular material. For instance, additional amino acids may be attached to the polypeptide sequences, such as a cysteine in the case of attaching the polypeptide to thiol-reactive molecules.

The molecular fusion may comprise a polymer. The polymer may be branched or linear. The molecular fusion may comprise a dendrimer. In general, soluble hydrophilic biocompatible polymers may be used so that the conjugate is soluble and is bioavailable after introduction into the patient. Examples of soluble polymers are polyvinyl alcohols, polyethylene imines, and polyethylene glycols (a term including polyethylene oxides) having a molecular weight of at least 100, 400, or between 100 and 400,000 (with all ranges and values between these explicit values being contemplated). Solubility in this context refers to a solubility in water or physiological saline of at least 1 gram per liter. Domains of biodegradable polymers may also be used, e.g., polylactic acid, polyglycolic acid, copolymers of polylactic and polyglycolic acid, polycaprolactones, polyhydroxy butyric acid, polyorthoesters, polyacetals, polydihydropyrans, and polycyanoacylates.

Embodiments include a polymer comprising a polypeptide comprising a synthetic PlGF2 peptide. For example embodiments include the polymers listed above as well as a polysaccharide, polyethylene glycol, polyalkylene oxide, collagen, or gelatin. The polymer may further comprises a transglutaminase substrate (TG), a cytokine, and the like.

In some embodiments, a polypeptide-polymer association, e.g., a molecular fusion, is prepared and introduced into the body as a purified composition in a pharmaceutically acceptable condition, or with a pharmaceutical excipient. The site of introduction may be, e.g., systemic, or at a tissue or a transplantation site.

Embodiments include a molecular fusion between a PlGF2 domain and a protein drug, such as a recombinant fusion protein comprising a PlGF2 domain and the protein drug, a chemical conjugate comprising a PlGF2 domain and the protein drug, or an indirect chemical conjugate comprising the PlGF2 domain and the protein drug mediated through joint fusion to a polymer or a polymeric micelle or nanoparticle. Molecular fusions between the PlGF2 domain and the protein drug may serve to anchor the protein drug to tissues when administered in tissue sites, by affinity with fibrinogen/fibrin in injured tissue sites or by affinity to ECM proteins in tissue sites. As such, a preferred embodiment is a molecular fusion of a PlGF2 domain and a protein drug in a pharmaceutically acceptable carrier. Alternatively, molecular fusions between the PlGF2 domain and a protein drug may serve to anchor the protein drug within a fibrin matrix. Fibrin is a commonly used biomaterial matrix, used in sealing and adhering tissues, in regenerative medicine applications, and in drug delivery applications. Anchoring protein drugs within fibrin matrices may provide pharmacological benefits in these and other applications. Peptide and protein antigens may also be linked anchored within fibrin matrices by forming a molecular fusion between the antigen and a PlGF2 domain. As such, a preferred embodiment is a molecular fusion of a PlGF2 domain and a protein drug or antigen in a pharmaceutically acceptable formulation of fibrinogen/fibrin. Fibrinogen/fibrin may also be prepared from autologous sources, and as such a preferred embodiment is a molecular fusion of a PlGF2 domain and a protein drug or antigen in a pharmaceutically acceptable carrier for application in autologous fibrin.

Vehicle

In many cases, a therapeutic agent, e.g., protein drugs such as cytokines, hormones, or cell-adhesion proteins might be delivered directly at the body site that needs to be treated without the use of any matrix. However, due to interstitial flow and drainage, cytokines or other soluble agents can be rapidly cleared from the site of injection, depending of their binding affinity for the ECM. Since cytokines modified with a PlGF2 sequence, e.g., $PlGF2_{123-144}$ sequence, show improved binding to several extracellular matrix proteins including fibronectin, tenascin C, vitronectin, osteopontin, and collagen I, they can be better retained at the site of injection, resulting in an improved treatment.

A PlGF2 peptide may be used as a vehicle for delivery of a therapeutic agent. The vehicle is soluble or a colloid in a physiological solution with all components of the vehicle preferably being less than about 500 μm in maximum dimension when released in the body. Embodiments of the PlGF2 vehicle include a molecular fusion of a biological agent and a peptide comprising a sequence chosen from the group consisting of SEQ ID NO:4 having from 0 to 5 conservative substitutions, SEQ ID NO:5 having from 0 to 5 conservative substitutions, and subsequences thereof, said nucleic acid exhibiting specific binding to one or more of fibrinogen, fibronectin, vitronectin, tenascin C, osteopontin, and fibrin. The biological agent may be chosen from the group consisting of a protein, a protein drug, a marker, an immunoagent, a chemokine, a cytokine, and a cell adhesion peptide.

In use, a PlGF2 peptide, by itself or as part of a molecular fusion, exhibits binding specificity for various ECM molecules, including fibrinogen, fibronectin, vitronectin, tenascin C, osteopontin, and fibrin. In this context, fibrinogen and fibrin may be viewed as temporary ECM. Placement of the PlGF2 vehicle into a tissue results in localized immobilization of the vehicle at or near the site of placement, and is not systemic. The agent(s) carried by the vehicle will be released over time or be consumed where they are immobilized by cells that are interacting with the tissue. The patient's own tissue can thus serve as a biomatrix for delivery of factors. Many uses for biomatrices are known, including extended release of drugs.

Matrices

Embodiments include a biomaterial incorporating a PlGF2 domain in a matrix. The term matrix refers to a synthetic three-dimensional structure, including a block, sheet, or film; it is a term used in contrast to a soluble or fluid material. The term synthetic means not native to the patient, and being exogenous relative to the patient. The matrices, when used internally as scaffolds, have to withstand mechanical loads, contain suitable degradation kinetics, and present bioactive molecules. Scaffolds function as a fusion of cell carrier and drug delivery device for the purpose of tissue engineering. To mimic the natural microenvironment for cells in order to induce tissue repair and regeneration, synthetic materials can be modified with ECM fragments. ECM fragments described in this report may be designed to form a molecular fusion with a transglutaminase (TG) substrate at the N terminus, consisting of residues 1-8 of the protein alpha2 plasmin inhibitor (α2PI1-8, NQEQVSPL (SEQ ID NO:50)). Factor XIIIa can therefore be used as a transglutaminase to catalyze the reaction between the glutamines of this sequence (NQEQVSPL) and the lysines of different biomaterials. The coagulation enzyme, factor XIIIa, will covalently bind the free amine group of the lysines (Lys) to the gamma-carboxamid group of glutamine (Gln), resulting in bonds that exhibit high resistance to proteolytic degradation. For example, natural fibrin hydrogels are cross-linked by this mechanism and a TG-PlGF2 domain can therefore be cross-linked inside the gel (Schense and Hubbell, 1999).

With regard to preferred embodiments to anchor biomolecules to a fibrin matrix, the biomolecule may be a recombinant protein drug for local delivery in tissue repair, including cytokines. Thus, a preferred embodiment for tissue repair is a pharmaceutical formulation of a tissue repair matrix comprising fibrinogen or fibrin and a molecular fusion between the PlGF2$_{123-144}$ and a recombinant cytokine, including members of the epidermal growth factor (EGF), VEGF, PDGF, FGF, IGF, BMP, TGF-β and neurotrophin families and superfamiles. The fibrin matrix may also serve as a controlled release matrix for sustained delivery of molecular fusions of protein drugs with a PLGF2 domain or PlGF2$_{123-144}$ and protein drugs.

A preferred embodiment is a fusion protein comprising the PLGF2 domain or PlGF2$_{123-144}$ and the cytokine VEGF-A, the denotation VEGF-A referring to any of the isoforms of VEGF-A.

The PlGF2$_{123-144}$ may be used to engineer fibrin matrixes for local immunomodulation and immunopotentiation, including vaccination. Preferred embodiments are molecular fusions comprising the $PlGF2_{123-144}$ and a chemokine, chemokines of interest including INF-β, CXCL10, CXCL11, and CCL21 or cytokines including TGF-β1, TGF-β2 or TGF-β3. Preferred embodiments are an immunomodulation or immunopotentiation matrix comprising fibrinogen or fibrin and a molecular fusion between the PLGF2 domain or $PlGF2_{123-144}$ and a recombinant chemokine, chemokines of interest including INF-β, CXCL10, CXCL11, and CCL21 or cytokines including TGF-β1, TGF-β2 or TGF-β3. $PlGF2_{123-144}$ may be used to incorporate immunological danger signal extracellular matrix proteins in fibrin. $PlGF2_{123-144}$ may be used to incorporate danger signal extracellular matrix proteins in fibrin, including the fibrinogen-like globular domain of tenascin C, an immunological danger signal. A preferred embodiment is a molecular fusion of a PLGF2 domain and the fibrinogen-like globular domain of tenascin C.

An important application in immunopotentiation is vaccination. A preferred embodiment is a vaccine matrix comprising fibrinogen or fibrin and a molecular fusion of the PLGF2 domain and a peptide or protein antigen. A preferred embodiment is a molecular fusion between a PLGF2 domain and a peptide or protein antigen. A further preferred embodiment is a vaccine matrix comprising fibrinogen or fibrin, a molecular fusion between PLGF2 domain and a chemokine, a molecular fusion of PLGF2 and the fibrinogen-like globular domain of tenascin C, and a molecular fusion between a PLGF2 domain and a peptide or protein antigen.

Fibrin matrices also provide an adhesive environment within which cells migrate, infiltrate and invade. It is useful to be able to modulate this adhesion environment, and this may be done by making molecular fusions of adhesion peptides or adhesion protein domains, such as FN III9-10, or many corresponding domains found in fibronectin, vitronectin, laminin, and tenascin C, for example. Preferred embodiments are molecular fusions of $PlGF2_{123-144}$ and adhesion domains, the adhesion domains including the integrin-binding peptides derived from fibronectin, adhesion domains comprising the amino acid sequences RGD, RGDS (SEQ ID NO: 64), RGDSP (SEQ ID NO: 52), KLDAPT (SEQ ID NO: 51), IDGIHEL (SEQ ID NO: 49), IDAPS (SEQ ID NO: 48), LDV, and REDV (SEQ ID NO: 65), and the fibronectin adhesion domains FN III10, FN III9-10, as well as the $1^{st}$-$5^{th}$ FN type III repeats of tenascin, and the $3^{th}$ FN type III repeat of tenascin C.

In addition to adhesion domains, it is useful to anchor cytokine- and chemokine-binding domains within fibrin matrices. This can be accomplished with molecular fusions of a PLGF2 domain and cytokine- and chemokine-binding domains, for example from fibronectin, tenascin C, vitronectin, laminin and other matrix molecules. Preferred embodiments are a molecular fusion of a PLGF2 domain and FN III12-14, a molecular fusion of a PLGF2 domain and TNC III1-5, a molecular fusion of a PLGF2 domain and TNCIII 3-5, and a molecular fusion of a PLGF2 domain and TNCIII5.

It is also of value to anchor protease inhibitors within fibrin, to delay degradation of fibrin after implantation within or on the surface of the body. This can be accomplished with molecular fusions of a PLGF2 domain and a protease inhibitor, such as aprotinin. A preferred embodiment is a molecular fusion of PLGF2 and aprotinin. A preferred embodiment is a fibrin formulation comprising a molecular fusion of a PLGF2 domain and aprotinin.

Administration

Pharmaceutically acceptable carriers or excipients may be used to deliver embodiments as described herein. Excipient refers to an inert substance used as a diluent or vehicle for a therapeutic agent. Pharmaceutically acceptable carriers are used, in general, with a compound so as to make the compound useful for a therapy or as a product. In general, for any substance, a carrier is a material that is combined with the substance for delivery to an animal. Conventional pharmaceutical carriers, aqueous, powder or oily bases, thickeners and the like may be necessary or desirable. In some cases the carrier is essential for delivery, e.g., to solubilize an insoluble compound for liquid delivery; a buffer for control of the pH of the substance to preserve its activity; or a diluent to prevent loss of the substance in the storage vessel. In other cases, however, the carrier is for convenience, e.g., a liquid for more convenient administration. Pharmaceutically acceptable salts of the compounds described herein may be synthesized according to methods known to those skilled in the arts. Pharmaceutically acceptable substances or compositions are highly purified to be free of contaminants, are sterile, and are biocompatible. They further may include a carrier, salt, or excipient suited to administration to a patient. In the case of water as the carrier, the water is highly purified and processed to be free of contaminants, e.g., endotoxins.

The compounds described herein may be administered in admixture with suitable pharmaceutical diluents, excipients, extenders, or carriers (termed herein as a pharmaceutically acceptable carrier, or a carrier) suitably selected with respect to the intended form of administration and as consistent with conventional pharmaceutical practices. Thus the deliverable compound may be made in a form suitable for oral, rectal, topical, intravenous injection, intra-articular injection, parenteral administration, intra-nasal, or tracheal administration. Carriers include solids or liquids, and the type of carrier is chosen based on the type of administration being used. Suitable binders, lubricants, disintegrating agents, coloring agents, flavoring agents, flow-inducing agents, and melting agents may be included as carriers, e.g., for pills. For instance, an active component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. The compounds can be administered orally in solid dosage forms, such as capsules, tablets, and powders, or in liquid dosage forms, such as elixirs, syrups, and suspensions. The active compounds can also be administered parentally, in sterile liquid dosage forms. Buffers for achieving a physiological pH or osmolarity may also be used.

EXAMPLES

Example 1: A Short Amino-Acid Sequence within PlGF2 ($PlGF2_{123-144}$) Strongly Binds ECM Proteins A domain was discovered within PlGF2 ($PlGF2_{123-144}$) strongly and promiscuously binds ECM proteins. GF binding to ECM proteins was measured by ELISA. A signal over 0.1 (gray box) was considered as representative of a specific binding. PlGF2 strongly bound all ECM proteins tested (gray bars). Alignment of the protein sequences of the splice variants PlGF2 and PlGF-1 (which does not bind) illustrates how PlGF2 contains an additional 21 amino-acid insert (PlGF2$_{123-144}$, in gray) located near the C-terminus. Binding of PlGF2$_{123-144}$ to ECM proteins when fused to a non-binding model protein, Glutathione S-transferase (GST) (GST-PlGF2$_{123-144}$) was tested. A scrambled version of PlGF2$_{123-144}$ (GST-PlGF2$_{scr}$) does not bind ECM proteins. FIG. 1 sets forth experimental data for the same.

Example 2: Optimization of the ECM Binding Domain of PlGF2

From Example 1, it was concluded that PlGF2$_{123-144}$ comprises an ECM protein binding domain. The binding of various GST-PLGF2 fragments to various ECM proteins, heparan sulfate, and neuropilin-1 was tested, with the results depicted in FIG. 2

This domain may be further engineered through removal of sequences that are not critical for binding ECM proteins through experimentation. Such experimentation can be carried out as follows. The ELISA assay described in Example 1 is useful as a read-out in such experimental optimization. Fusion proteins are made from a protein such as GST that comprise the full-length domain PlGF2$_{123-144}$ at one terminus, for example the C-terminus, and binding to surface-bound fibrinogen is measured by an ELISA assay using an antibody that detects the protein GST to establish a baseline of binding induced by the full-length PlGF2$_{123-144}$ domain.

Further fusion proteins are made, comprising the PlGF2$_{123-144}$ domain that has been trimmed by one or more amino acid residues from the C-terminal end of the full-length PlGF2$_{123-144}$ or from the N-terminal end of the full-length PlGF2$_{123-144}$. Thus, two families of fusion proteins are formed, one with shortening at the N-terminal end of PlGF2$_{123-144}$ and one with shortening at the C-terminal end of PlGF2$_{123-144}$. Measurement of binding to the surface-bound ECM allows determination of the structure-function relationship between PlGF2$_{123-144}$ length (from either end) and affinity for ECM proteins. Conservative substitutions of amino acids within this domain may be similarly characterized.

Example 3: Design and Production of ECM-Binding Cytokines Containing PlGF2$_{123-144}$ Sequences encoding for molecular fusions, in particular fusion proteins, of human cytokines (VEGF-A165, PDGF-BB and BMP-2) and the PlGF2$_{123-144}$ domain were amplified by the polymerase chain reaction and were assembled into the mammalian expression vector pXLG, in order to obtain cytokine-PlGF2$_{123-144}$ (SEQ ID NOs: 7, 9, 11, 12, and 13). In order to avoid a protein-misfolding issue due to the inclusion of PlGF2$_{123-144}$, the single cysteine within the PlGF2$_{123-144}$ (Cys$^{142}$), can be removed or substituted with another amino acid such as a serine (PlGF2$_{123-144*}$.) The fusion proteins were expressed in HEK cells and purified by immobilized metal affinity chromatography using a binding buffer containing 500 mM NaCl, 20 mM sodium phosphate and 10 mM imidazole, pH 7.4. The protein was further dialyzed against Tris buffer (20 mM Tris, 150 mM NaCl, pH 7.4). Design examples of cytokines containing PlGF2$_{123-144*}$ are shown in FIG. 3.

```
SEQ ID NO: 6: human VEGF-A121
APMAEGGGQNHHEVVKFMDVYQRSYCHPIETLVDIFQEYPDEIEYIFKPSCVPLMRCGG

CCNDEGLECVPTEESNITMQIMRIKPHQGQHIGEMSFLQHNKCECRPKKDRARQECDKP

RR

SEQ ID NO: 7: human VEGF-A121-PlGF2₁₂₃₋₁₄₄
APMAEGGGQNHHEVVKFMDVYQRSYCHPIETLVDIFQEYPDEIEYIFKPSCVPLMRCGG

CCNDEGLECVPTEESNITMQIMRIKPHQGQHIGEMSFLQHNKCECRPKKDRARQERRRPK

GRGKRRREKQRPTDCHLCDKPRR
```

The denotation VEGF-A-PlGF2$_{123-144}$ is used to refer to SEQ ID NO: 7 and to other fusion designs of VEGF-A comprising the PlGF2$_{123-144}$ domain.

```
SEQ ID NO: 8: human PDGF-BB
SLGSLTIAEPAMIAECKTRTEVFEISRRLIDRTNANFLVWPPCVEVQRCSGCCNNRNVQCR

PTQVQLRPVQVRKIEIVRKKPIFKKATVTLEDHLACKCETVAAARPVT

SEQ ID NO: 9: human PDGF-BB-PlGF2₁₂₃₋₁₄₄
SLGSLTIAEPAMIAECKTRTEVFEISRRLIDRTNANFLVWPPCVEVQRCSGCCNNRNVQCR

PTQVQLRPVQVRKIEIVRKKPIFKKATVTLEDHLACKCETVAAARPVTRRRPKGRGKRRR

EKQRPTDCHL

SEQ ID NO: 10: human BMP-2
QAKHKQRKRLKSSCKRHPLYVDFSDVGWNDWIVAPPGYHAFYCHGECPFPLADHLNST

NHAIVQTLVNSVNSKIPKACCVPTELSAISMLYLDENEKVVLKNYQDMVVEGCGCR

SEQ ID NO: 11: human BMP-2-PlGF2₁₂₃₋₁₄₄
```

-continued
```
QAKHKQRKRLKSSCKRHPLYVDFSDVGWNDWIVAPPGYHAFYCHGECPFPLADHLNST

NHAIVQTLVNSVNSKIPKACCVPTELSAISMLYLDENEKVVLKNYQDMVVEGCGCRRRP

KGRGKRRREKQRPTDCHL

SEQ ID NO: 12: human PlGF2$_{123-144}$ - BMP-2

RRRPKGRGKRRREKQRPTDCHLSCKRHPLYVDFSDVGWNDWIVAPPGYHAFYCHGECP

FPLADHLNSTNHAIVQTLVNSVNSKIPKACCVPTELSAISMLYLDENEKVVLKNYQDMV

VEGCGCR

SEQ ID NO: 13: human BMP-2-PlGF2$_{123-144*}$
QAKHKQRKRLKSSCKRHPLYVDFSDVGWNDWIVAPPGYHAFYCHGECPFPLADHLNST

NHAIVQTLVNSVNSKIPKACCVPTELSAISMLYLDENEKVVLKNYQDMVVEGCGCRRRP

KGRGKRRREKQRPTDSHL
```

Example 4: Cytokines Modified with PlGF2$_{123-144}$, or PlGF2$_{123-144*}$ Display Enhanced Affinity for ECM Components The binding of various cytokines modified with PlGF2123-144(*) to various ECM proteins and heparan sulfate was tested, with the results depicted in FIG. 4 panels a and b. Dissociation constants were determined as shown in Table 1, which sets forth the cytokines-PlGF2$_{123-144(*)}$ affinity constants to various ECM proteins and heparan sulfate, measured by ELISA. The dissociation constant ($K_D$) was obtained by non-linear regression using A450 nm=Bmax*[concentration]/($K_D$+[concentration]). The affinity to ECM protein and heparan sulfate of cytokines modified with PlGF2$_{123-144(*)}$ (VEGF-A121-PlGF2$_{123-144}$, PDGF-BB-PlGF2$_{123-144}$, and BMP-2-PlGF2$_{123-144*}$) was observed to be much higher (lower $K_D$) than wild-type cytokines. As such, the affinity of PlGF2 for ECM proteins was conferred upon VEGF-A165, PDGF-BB, and BMP-2 by fusion of the PlGF2$_{123-144}$ to VEGF-A165, PDGF-BB, and BMP-2, respectively.

TABLE 1

| KD (nM) | Fibronectin | Vitronectin | Tenascin C | Osteopontin | Fibrinogen | Collagen I | Heparan sulfate |
|---|---|---|---|---|---|---|---|
| VEGF-A165 | 97.2 ± 10.4 | 70.9 ± 11.3 | 115.3 ± 15.7 | 71.0 ± 8.4 | 301.5 ± 73.0 | >500 | 60.9 ± 9.7 |
| VEGF-A-PlGF-2$_{123-144}$ | 11.2 ± 3.3 | 2.8 ± 0.3 | 18.0 ± 1.2 | 26.4 ± 13.2 | 5.8 ± 0.6 | 123.9 ± 16.1 | 5.9 ± 0.5 |
| PDGF-BB | 11.6 ± 1.4 | 10.5 ± 1.0 | 19.0 ± 2.8 | 20.3 ± 2.2 | 250.4 ± 57.6 | >500 | 42.3 ± 6.3 |
| PDGF-BB-PlGF-2$_{123-144}$ | 4.5 ± 0.3 | 1.2 ± 0.1 | 6.3 ± 0.6 | 3.3 ± 0.5 | 3.2 ± 0.2 | 96.3 ± 13.4 | 4.8 ± 0.4 |
| BMP-2 | 19.2 ± 2.3 | 94.7 ± 12.8 | 25.5 ± 2.1 | 47.8 ± 4.2 | 47.1 ± 4.5 | >500 | 17.1 ± 1.9 |
| BMP-2-PlGF-2$_{123-144*}$ | 5.2 ± 0.4 | 2.4 ± 0.2 | 6.9 ± 0.7 | 11.2 ± 1.1 | 2.0 ± 0.1 | 101.7 ± 17.9 | 2.8 ± 0.3 |
| PlGF-2 | 7.2 ± 1.1 | 2.0 ± 0.2 | 10.1 ± 1.0 | 13.1 ± 1.4 | 4.5 ± 0.6 | 126.4 ± 15.7 | 4.6 ± 0.4 |

Example 5: Design of ECM-Binding Cytokines Fused to $PlGF2_{123-144(*)}$ or with a Cytokine Domain Substituted with PlGF2123-133 (*)

Sequences encoding for molecular fusions, in particular fusion proteins, of cytokines and the $PlGF2_{123-144(*)}$ domain were amplified by the polymerase chain reaction and were assembled into the mammalian expression vector pXLG, in order to obtain cytokine-$PlGF2_{123-144(*)}$ or $PlGF2_{123-144(*)}$-cytokine. A fusion protein between $PlGF2_{123-144(*)}$ and the human forms of IGF-I, TGF-β1, TGF-β2, BDNF, and NT-3 are designed in SEQ ID NOs: 15, 17, 18, 20, 22, and 24. A shorter sequence from $PlGF2_{123-144(*)}$ can also be used. SEQ ID NOs: 1-20 were actually made, and SEQ ID NO: Nos 21-24 are shown as examples of further embodiments.

```
SEQ ID NO: 14: human IGF-I:
GPETLCGAELVDALQFVCGDRGFYFNKPTGYGSSSRRAPQTGIVDECCFRSCDLRRLEM

YCAPLKPAKSA

SEQ ID NO: 15: human IGF-I-PlGF2123-144:
GPETLCGAELVDALQFVCGDRGFYFNKPTGYGSSSRRAPQTGIVDECCFRSCDLRRLEM

YCAPLKPAKSARRRPKGRGKRRREKQRPTDCHL

SEQ ID NO: 16: human TGF-β1:
ALDTNYCFSSTEKNCCVRQLYIDFRKDLGWKWIHEPKGYHANFCLGPCPYIWSLDTQYS

KVLALYNQHNPGASAAPCCVPQALEPLPIVYYVGRKPKVEQLSNMIVRSCKCS

SEQ ID NO: 17: human TGF-β1-PlGF2123-144:
ALDTNYCFSSTEKNCCVRQLYIDFRKDLGWKWIHEPKGYHANFCLGPCPYIWSLDTQYS

KVLALYNQHNPGASAAPCCVPQALEPLPIVYYVGRKPKVEQLSNMIVRSCKCSRRRPKG

RGKRRREKQRPTDCHL

SEQ ID NO: 18: human PlGF2123-144*-TGF-β1:
RRRPKGRGKRRREKQRPTDSHLALDTNYCFSSTEKNCCVRQLYIDFRKDLGWKWIHEPK

GYHANFCLGPCPYIWSLDTQYSKVLALYNQHNPGASAAPCCVPQALEPLPIVYYVGRKP

KVEQLSNMIVRSCKCS

SEQ ID NO: 19: human TGF-β2:
ALDAAYCFRNVQDNCCLRPLYIDFKRDLGWKWIHEPKGYNANFCAGACPYLWSSDTQH

SRVLSLYNTINPEASASPCCVSQDLEPLTILYYIGKTPKIEQLSNMIVKSCKCS

SEQ ID NO: 20: human PlGF2123-144*-TGF-β2
RRRPKGRGKRRREKQRPTDSHLALDAAYCFRNVQDNCCLRPLYIDFKRDLGWKWIHEP

KGYNANFCAGACPYLWSSDTQHSRVLSLYNTINPEASASPCCVSQDLEPLTILYYIGKTP

KIEQLSNMIVKSCKCS

SEQ ID NO: 21: human BDNF
HSDPARRGELSVCDSISEWVTAADKKTAVDMSGGTVTVLEKVPVSKGQLKQYFYETKC

NPMGYTKEGCRGIDKRHWNSQCRTTQSYVRALTMDSKKRIGWRFIRIDTSCVCTLTIKR

GR

SEQ ID NO: 22: human BDNF-PlGF2123-144
HSDPARRGELSVCDSISEWVTAADKKTAVDMSGGTVTVLEKVPVSKGQLKQYFYETKC

NPMGYTKEGCRGIDKRHWNSQCRTTQSYVRALTMDSKKRIGWRFIRIDTSCVCTLTIKR

GRRRPKGRGKRRREKQRPTDCHL

SEQ ID NO: 23: human NT-3:
YAEHKSHRGEYSVCDSESLWVTDKSSAIDIRGHQVTVLGEIKTGNSPVKQYFYETRCKE

ARPVKNGCRGIDDKHWNSQCKTSQTYVRALTSENNKLVGWRWIRIDTSCVCALSRKIGR

T

SEQ ID NO: 24: human NT-3-PlGF2123-144
YAEHKSHRGEYSVCDSESLWVTDKSSAIDIRGHQVTVLGEIKTGNSPVKQYFYETRCKE

ARPVKNGCRGIDDKHWNSQCKTSQTYVRALTSENNKLVGWRWIRIDTSCVCALSRKIGR

TRRRPKGRGKRRREKQRPTDCHL
```

Example 6: Activity of Cytokines Fused to PlGF2$_{123-144}$

FIG. 5 sets forth the results. In vitro, PlGF2$_{123-144}$-fused growth factors (GFs) showed similar bioactivity compared to wild-type GFs. Human ECs were stimulated with VEGF-A121, VEGF-A165, or VEGF-A-PlGF2$_{123-144}$, and human mesenchymal stem cells were stimulated with PDGF-BB or PDGF-BB-PlGF2$_{123-144}$. Phosphorylated GF receptors (VEGFR-2 and PDGFR-13) were quantified by ELISA (n=3, mean±SEM). The insertion of the PlGF2$_{123-144}$ into VEGF-A and PDGF-BB did not alter their signaling. Moreover, the insertion of PlGF2$_{123-144}$ into VEGF-A121 increased its activity to the level of VEGF-A165. BMP-2-PlGF2$_{123-144*}$ was evaluated by its ability to promote ALP activity in human mesenchymal stem cells (induction of osteoblastic differentiation). Cellular ALP was quantified after 14 days of culture in presence of BMP-2 or BMP-2-PlGF2$_{123-144*}$. No differences in cell number and ALP activity were observed between cells treated with BMP-2 or BMP-2-PlGF2$_{123-144*}$.

Example 7: In Vivo Retention of Cytokines Fused to PlGF2$_{123-144(*)}$

Results are shown in FIG. 6. ECM super-affinity cytokine variants were created that bind to and are retained by ECM molecules in vivo. For example, when injected subcutaneously in the back skin of mice, VEGF-A165 rapidly disappeared from the injection site, with only 10% remaining in the skin tissue after 3 days. In contrast, about 50% of the injected VEGF-A-PlGF2$_{123-144}$ remained after 3 days, and more than 10% could be detected after 6 days. Additionally, in the back skin or calvarium of mice filled with a fibrin matrix containing wild-type or PlGF2$_{123-144}$-fused cytokines, low amounts of wild-type cytokines were detectable within the delivery site after 3 and 6 days, while PlGF2$_{123-144}$-fused cytokines were significantly retained in the fibrin matrix and within the tissue surrounding the defects.

Example 8: Treatment of Skin Wounds with Fibrin Matrix Comprising Cytokines Fused to PlGF2$_{123-144}$ Results are shown in FIG. 7. Preclinical evaluations of cytokines for chronic skin-wound healing are generally performed in rodents and most commonly in the db/db diabetic mouse (Hanft J R, et al., 2008; Robson M C, et al., 1992; Robson M C, et al., 1992; Robson M C, et al., 2001), despite the fact that the optimal disease model does not yet exist for human chronic wounds. Nevertheless, there is consensus that the genetically modified db/db mouse represents a clinically relevant model for diabetes-impaired skin-wound healing (Davidson J M, 1998; Sullivan S R, et al., 2004). Success in the db/db mouse model directly opens the way for clinical trials (Hanft J R, et al., 2008; Robson M C, et al., 1992). Full-thickness back-skin wounds were treated with a roughly 100-fold lower dose of cytokines (200 ng of each PDGF-BB and VEGF-A, combined) delivered once in a fibrin matrix or simply applied topically three to four times. These low doses of wild-type PDGF-BB and VEGF-A (delivered in fibrin or topically) did not significantly enhance wound healing compared to untreated or fibrin alone-treated wounds as indicated by either extent of wound closure (the latter indicated by re-epithelialization) or amount of granulation tissue. In contrast, wounds treated with the engineered ECM super-affinity PlGF2$_{123-144}$-fused PDGF-BB and VEGF-A led to significantly faster wound closure and to more granulation tissue, both topically and in fibrin. Because angiogenesis is a crucial step in sustaining newly formed granulation tissue (Gunner G C, et al., 2008), we focused on the extent to which angiogenesis differed between the treatments. Immunohistological analysis for CD31 (highly expressed by ECs) and desmin (expressed by smooth muscle cells (SMCs) stabilizing blood vessels) revealed that angiogenesis within the granulation tissues was much more pronounced when PlGF2$_{123-144}$-fused GFs were delivered. For example, 20 μg/wound of VEGF-A165 or 10 μg/wound of PDGF-BB (REGRANEX®) applied topically for five consecutive days has been reported to be efficient in the db/db mouse (Chan R K, et al., 2006; Galiano R D, et al., 2004).

Example 9: Vascular Permeability Induced by VEGF-A Fused to PlGF2$_{123-144}$ Results are shown in FIG. 8. VEGF-A-PlGF2$_{123-144}$ induces much less vascular permeability than the same dose of wild-type VEGF-A165 (10 μg). Vascular permeability was measured in the mouse ear skin. Permeability induced by VEGF-A was visualized by the red-labeled dextran leaking from the vessels. VEGF-A165 was compared to VEGF-A-PlGF2$_{123-144}$ Images of the mouse ear skin vasculature were analyzed after VEGF-A application. The results indicated that this approach could resolve a major problem that has arisen in translating VEGF-A to clinical use. Indeed, while VEGF-A activation of VEGF-receptor 2 (VEGF-R2) may be a powerful approach to promote angiogenesis, actual administration of VEGF-A has been shown to rapidly induce vascular permeability, which leads to systemic hypotension and edema; this phenomenon has been the dose-limiting toxic response in peripheral and cardiovascular applications (Simons M and Ware J A, 2003) and presents serious issues in regenerative medicine. Because VEGF-A-PlGF2$_{123-144}$ has an enhanced capacity to bind endogenous ECM, VEGF-A-PlGF2$_{123-144}$ might induce less vascular permeability. In a model of dextran extravasation from vessels in the skin of the mouse ear (Kilarski W W, et al., 2013), the rate of leakage due to application of 10 μg VEGF-A-PlGF2$_{123-144}$ was only 19±7% of that due to application of wild-type VEGF-A165, even though it showed equivalent activity in phosphorylation of VEGFR-2 as VEGF-A165. As such, engineering of VEGF-A to form VEGF-A-PlGF2$_{123-144}$ appears to decouple angiogenesis (as shown in the model of skin wound healing) from hyperpermeability, potentially solving a major problem with VEGF-A's clinical translation.

Example 10: Treatment of Bone Defects with Fibrin Matrix Comprising Cytokines Fused to PlGF2$_{123-144}$ Results are shown in FIG. 9. Cytokines fused to PlGF2$_{123-144}$ are useful in engineering a microenvironment for bone healing. Since, the cytokines BMP-2 and PDGF-BB are beneficial for bone repair (Hollinger J O, et al., 2008), fibrin matrices containing a low dose of combined BMP-2 (200 ng) and PDGF-BB (200 ng), were evaluated for bone repair. A relevant model to illustrate human translational potential is the critical-size calvarial defect in a skeletally mature rat, which is a standard and clinically relevant model for nonunion bone healing (Hollinger J O and Kleinschmidt J C, 1990; Muschler G F, et al.). Preclinical evaluations of bone repair materials and osteoinductive proteins commonly include critical-size bone defect models, such as the critical-size calvarial defect in the rat (Hollinger J O and Kleinschmidt J C, 1990). A combination of BMP-2-PlGF2$_{123-144*}$ and PDGF-BB-PlGF2$_{123-144}$ (200 ng of each) were delivered in a fibrin matrix, or delivered topically to the dura prior to surgical skin closure at a somewhat higher dose (1 µg of each, combined). After 4 weeks, bone healing—characterized by bone tissue deposition and coverage of the defects—was analyzed using microcomputed tomography (microCT). The delivery of wild-type GFs alone or within fibrin slightly increase bone healing when compared to the defects without treatment or treated with fibrin only. In contrast, treatment with PlGF2$_{123-144}$-fused GFs led to a marked increase of bone tissue deposition compared to wild-type GF. For comparison, 1 µg is usually insufficient to treat calvarial defect of 6 mm in the rat (Schmoekel H G, et al., 2005), and milligram-quantities of BMP-2 are needed to treat tibial fractures in humans (Gautschi O P, et al., 2007).

Example 11: Engineering the Adhesion Domain of ECM Proteins Fused to the PlGF2$_{123-144}$ Domain To incorporate a cell adhesion-promoting domain within fibrin matrices, molecular fusions of FN III10 and FN III9-10 and PlGF2$_{123-144}$ are useful. SEQ ID NO: 25 presents a design using FN III9-10 that may easily be made by the artisan reading this specification.

```
SEQ ID NO: 25: human FN III9-10-PlGF2₁₂₃₋₁₄₄
GLDSPTGIDFSDITANSFTVHWIAPRATITGYRIRHHPEHFSGRPREDRVPHSRNSITLTNLT

PGTEYVVSIVALNGREESPPLIGQQSTVSDVPRDLEVVAATPTSLLISWDAPAVTVRYYRI

TYGETGGNSPVQEFTVPGSKSTATISGLKPGVDYTITVYAVTGRGDSPASSKPISINYRTR

RRPKGRGKRRREKQRPTDCHL
```

Example 12: Engineering a Protein Drug for Sustained Release from Fibrin Matrices Utilizing the PlGF2$_{123-144}$ Domain PTH1-34 is known to be useful in regulating system bone mass, and local application of fibrin-binding PTH1-34 variants has been shown to stimulate local bone formation (Arrighi I, et al., 2009). A fusion protein of PTH1-34 and PlGF2$_{123-144}$ is designed as in SEQ ID NO: 27; this protein may be readily made by the artisan reading this specification.

```
SEQ ID NO: 26: human PTH1-34
SVSEIQLMHNLGKHLNSMERVEWLRKKLQDVHNF

SEQ ID NO: 27: human PTH1-34-PlGF2₁₂₃₋₁₄₄
SVSEIQLMHNLGKHLNSMERVEWLRKKLQDVHNFRRRPKGRGKRRREKQ

RPTDCHL
```

Example 13: Engineering a Protease Inhibitor Fused to PlGF2$_{123-144}$

Fibrin has been long used clinically for hemostasis and sealing, yet extension of use in other applications has been limited due to its relatively rapid resorption in vivo, even with addition of aprotinin or other protease inhibitors. Retention of the protease inhibitor aprotinin in fibrin matrices can be accomplished by design and use of a fusion of aprotinin with PlGF2$_{123-144}$. This fusion is designed as in SEQ ID NO: 29; this protein may be readily made by the artisan reading this specification.

```
SEQ ID NO: 28: bovine aprotinin
RPDFCLEPPYTGPCKARIIRYFYNAKAGLCQTFVYGGCRAKRNNFKSAEDCMRTCGGA SEQ ID NO: 29: bovine aprotinin-PlGF2₁₂₃₋₁₄₄
RPDFCLEPPYTGPCKARIIRYFYNAKAGLCQTFVYGGCRAKRNNFKSAEDCMRTCGGAR

RRPKGRGKRRREKQRPTDCHL
```

Example 14: Engineering a Chemokine Fused to PlGF2$_{123-144}$

Fibrin-binding chemokines are useful in immunomodulation and immunotherapy, including vaccination. Fusions of the chemokines CXCL10, CXCL11, IFN-γ, and CCL21 with $PlGF2_{123-144}$ are designed in SEQ ID NO: 31, 33, 35 and 37, respectively. These proteins may be readily made by the artisan reading this specification.

SEQ ID NO: 30: human CXCL10
VPLSRTVRCTCISISNQPVNPRSLEKLEIIPASQFCPRVEIIATMKKKGEKRCLNPESKAIKN
LLKAVSKERSKRSP SEQ ID NO: 31: human CXCL10-$PlGF2_{123-144}$
VPLSRTVRCTCISISNQPVNPRSLEKLEIIPASQFCPRVEIIATMKKKGEKRCLNPESKAIKN
LLKAVSKERSKRSPRRRPKGRGKRRREKQRPTDCHL SEQ ID NO: 32: human CXCL11-$PlGF2_{123-144}$
FPMFKRGRCLCIGPGVKAVKVADIEKASIMYPSNNCDKIEVIITLKENKGQRCLNPKSKQ
ARLIIKKVERKNF SEQ ID NO: 33: human CXCL11-$PlGF2_{123-144}$
FPMFKRGRCLCIGPGVKAVKVADIEKASIMYPSNNCDKIEVIITLKENKGQRCLNPKSKQ
ARLIIKKVERKNFRRRPKGRGKRRREKQRPTDCHL SEQ ID NO: 34: human IFN-γ
QDPYVKEAENLKKYFNAGHSDVADNGTLFLGILKNWKEESDRKIMQSQIVSFYFKLFKN
FKDDQSIQKSVETIKEDMNVKFFNSNKKKRDDFEKLTNYSVTDLNVQRKAIHELIQVMA
ELSPAAKTGKRKRSQMLFRG SEQ ID NO: 35: human IFN-γ-$PlGF2_{123-144}$
QDPYVKEAENLKKYFNAGHSDVADNGTLFLGILKNWKEESDRKIMQSQIVSFYFKLFKN
FKDDQSIQKSVETIKEDMNVKFFNSNKKKRDDFEKLTNYSVTDLNVQRKAIHELIQVMA
ELSPAAKTGKRKRSQMLFRGRRRPKGRGKRRREKQRPTDCHL SEQ ID NO: 36: human CCL21
SDGGAQDCCLKYSQRKIPAKVVRSYRKQEPSLGCSIPAILFLPRKRSQAELCADPKELWV
QQLMQHLDKTPSPQKPAQGCRKDRGASKTGKKGKGSKGCKRTERSQTPKGP SEQ ID NO: 37: human CCL21-$PlGF2_{123-144}$
SDGGAQDCCLKYSQRKIPAKVVRSYRKQEPSLGCSIPAILFLPRKRSQAELCADPKELWV
QQLMQHLDKTPSPQRRRPKGRGKRRREKQRPTDCHL

Example 15: Engineering a Peptide and a Protein Antigen Fused to PlGF2$_{123-144}$ L-dopachrome tautomerase, also called tyrosinase-related protein 2 (TRP-2), has been identified as a human melanoma-associated antigen and it is expressed by most melanomas as well as normal melanocytes in humans and mice. Human TRP-2 protein or peptide-pulsed dendritic cells have shown the induction of specific CD8+T cells, suggesting that self-reactive TRP-2 CD81 T-cell epitope 180-188 (trp2)-specific cells may escape thymic selection (Sierro S R, et al., 2011). The fibrin-binding affinity of $PlGF2_{123-144}$ can be used to incorporate antigens into fibrin matrices used as vaccines. An antigen relevant for cancer vaccine in treatment of melanoma is designed as SEQ ID NO: 39, comprising a specific peptide antigen from TRP-2 and as SEQ ID NO: 41, comprising the entire protein TRP-2, in both cases fused to $PlGF2_{123-144}$. These examples are designed and presented to show how artisans can readily adapt these methods to use these or other antigens.

SEQ ID NO: 38: human L-dopachrome tautomerase 180-188
SVYDFFVWL

SEQ ID NO: 39: human $PlGF2_{123-144}$/plasmin cleavage site derived from factor X/L-dopachrome tautomerase 180-188
RRRPKGRGKRRREKQRPTDCHLITFRSVYDFFVWL SEQ ID NO: 40: human L-dopachrome tautomerase
QFPRVCMTVDSLVNKECCPRLGAESANVCGSQQGRGQCTEVRADTRPWSGPYILRNQD

DRELWPRKFFHRTCKCTGNFAGYNCGDCKFGWTGPNCERKKPPVIRQNIHSLSPQEREQ

FLGALDLAKKRVHPDYVITTQHWLGLLGPNGTQPQFANCSVYDFFVWLHYYSVRDTLL

GPGRPYRAIDFSHQGPAFVTWHRYHLLCLERDLQRLIGNESFALPYWNFATGRNECDVC

TDQLFGAARPDDPTLISRNSRFSSWETVCDSLDDYNHLVTLCNGTYEGLLRRNQMGRNS

MKLPTLKDIRDCLSLQKFDNPPFFQNSTFSFRNALEGFDKADGTLDSQVMSLHNLVHSFL

NGTNALPHSAANDPIFVVLHSFTDAIFDEWMKRFNPPADAWPQELAPIGHNRMYNMVPF

FPPVTNEELFLTSDQLGYSYAIDLPVSVEETPGWPTTLLVVMGTLVALVGLFVLLAFLQY

RRLRKGYTPLMETHLSSKRYTEEA

SEQ ID NO: 41: human L-dopachrome tautomerase-$PlGF2_{123-144}$
QFPRVCMTVDSLVNKECCPRLGAESANVCGSQQGRGQCTEVRADTRPWSGPYILRNQD

DRELWPRKFFHRTCKCTGNFAGYNCGDCKFGWTGPNCERKKPPVIRQNIHSLSPQEREQ

FLGALDLAKKRVHPDYVITTQHWLGLLGPNGTQPQFANCSVYDFFVWLHYYSVRDTLL

GPGRPYRAIDFSHQGPAFVTWHRYHLLCLERDLQRLIGNESFALPYWNFATGRNECDVC

TDQLFGAARPDDPTLISRNSRFSSWETVCDSLDDYNHLVTLCNGTYEGLLRRNQMGRNS

MKLPTLKDIRDCLSLQKFDNPPFFQNSTFSFRNALEGFDKADGTLDSQVMSLHNLVHSFL

NGTNALPHSAANDPIFVVLHSFTDAIFDEWMKRFNPPADAWPQELAPIGHNRMYNMVPF

FPPVTNEELFLTSDQLGYSYAIDLPVSVEETPGWPTTLLVVMGTLVALVGLFVLLAFLQY

RRLRKGYTPLMETHLSSKRYTEEARRRPKGRGKRRREKQRPTDCHL

Example 16: Engineering the Toll-Like Receptor Agonist Fused to PlGF2$_{123-144}$ Vaccines with incorporated danger signals provide signals to activate immune responses to incorporated antigens. The ECM protein fragment TNC fibrin globular domain (also referred to as the fibrinogen globe domain) is such a danger signal. The danger signal domain can be incorporated into fibrin matrixes by affinity of PlGF2$_{123-144}$ for fibrin. A fusion protein of TNC fibrin globe (SEQ ID NO: 42) and PlGF2$_{123-144}$ is designed in SEQ ID NO: 43.

```
SEQ ID NO: 42: human TNC fibrinogen globular domain
GLLYPFPKDCSQAMLNGDTTSGLYTIYLNGDKAQALEVFCDMTSDGGGWIVFLRRKNG

RENFYQNWKAYAAGFGDRREEFLHWLGLDNLNKITAQGQYELRVDLRDHGETAFAVY

DKFSVGDAKTRYKLKVEGYSGTAGDSMAYHNGRSFSTFDKDTDSAITNCALSYKGAFW

YRNCHRVNLMGRYGDNNHSQGVNWFHWKGHEHSIQFAEMKLRPSNFRNLEGRRKRA

SEQ ID NO: 43: human TNC fibrinogen globular domain-PlGF2₁₂₃₋₁₄₄
GLLYPFPKDCSQAMLNGDTTSGLYTIYLNGDKAQALEVFCDMTSDGGGWIVFLRRKNG

RENFYQNWKAYAAGFGDRREEFLHWLGLDNLNKITAQGQYELRVDLRDHGETAFAVY

DKFSVGDAKTRYKLKVEGYSGTAGDSMAYHNGRSFSTFDKDTDSAITNCALSYKGAFW

YRNCHRVNLMGRYGDNNHSQGVNWFHWKGHEHSIQFAEMKLRPSNFRNLEGRRRPKG

RGKRRREKQRPTDCHL
```

Example 17: Tissue Retention of Cytokines Containing the PlGF2$_{123-144}$

The cytokine FGF18 has been shown to lead to improved cartilage repair when injected in the joints of animals in osteoarthritis models (Moore E E, et al., 2005). Elimination from the site of injection limits the efficacy of this approach. An extracellular matrix-binding FGF18 variant is provided by a fusion protein between FGF18 and PlGF2$_{123-144}$, designed in SEQ ID NO: 45. This protein may be readily made by the artisan reading this specification, as well as other vehicles for other agents or cytokines.

```
SEQ ID NO: 44: human FGF18
EENVDFRIHVENQTRARDDVSRKQLRLYQLYSRTSGKHIQVLGRRISARGEDGDKYAQL

LVETDTFGSQVRIKGKETEFYLCMNRKGKLVGKPDGTSKECVFIEKVLENNYTALMSAK

YSGWYVGFTKKGRPRKGPKTRENQQDVHFMKRYPKGQPELQKPFKYTTVTKRSRRIRP

THPA

SEQ ID NO: 45: human FGF18-PlGF2₁₂₃₋₁₄₄
EENVDFRIHVENQTRARDDVSRKQLRLYQLYSRTSGKHIQVLGRRISARGEDGDKYAQL

LVETDTFGSQVRIKGKETEFYLCMNRKGKLVGKPDGTSKECVFIEKVLENNYTALMSAK

YSGWYVGFTKKGRPRKGPKTRENQQDVHFMKRYPKGQPELQKPFKYTTVTKRSRRIRP

THPARRRPKGRGKRRREKQRPTDCHL
```

One can make other FGF-18 variants in which the native domain within FGF-18 is replaced with a PlFG-2 domain. A hypothetical heparin binding domain exists within FGF-18, namely KRYPKGQPELQKPFKYTTVTKRSRRIR (SEQ ID NO:56), the key domain of which is KRSRRIR (SEQ ID NO:57). Thus, one substitutional implementation is to replace the KRSRRIR domain with a PlGF2 domain, for example SEQ ID NO: 53.

SEQ ID NO: 53: human FGF18-PlGF2$_{123-138}$
EENVDFRIHVENQTRARDDVSRKQLRLYQLYSRTSGKHIQVLGRRISARGEDGDKYAQL

LVETDTFGSQVRIKGKETEFYLCMNRKGKLVGKPDGTSKECVFIEKVLENNYTALMSAK

YSGWYVGFTKKGRPRKGPKTRENQQDVHFMKRYPKGQPELQKPFKYTTVTRRRPKGR

GKRRREKQRPTHPA

A second substitutional example is to extend the PlGF2 domain on its N terminal end so as to better match the amino acids within FGF-18, SEQ ID NO:54, using PlGF2$_{119-144}$, namely MKPERRRPKGRGKRRREKQRPTDCHL (SEQ ID NO:55) Other possible implementations exist as well.

SEQ ID NO: 54: human FGF18-PlGF2$_{121-138}$
EENVDFRIHVENQTRARDDVSRKQLRLYQLYSRTSGKHIQVLGRRISARGEDGDKYAQL

LVETDTFGSQVRIKGKETEFYLCMNRKGKLVGKPDGTSKECVFIEKVLENNYTAL

MSAKYSGWYVGFTKKGRPRKGPKTRENQQDVHFMKPERRRPKGRGKRRREKQRPTHP

A

The cytokine TGF-β3 has been extensively explored in limitation of dermal scars, for example post-surgical incisional scars. The cytokine has been injected along such incision lines (Ferguson M W, et al., 2009). Elimination from the site of injection limits the efficacy of this approach. An extracellular matrix-binding TGF-β3 variant is provided by a fusion protein between TGF-β3 and $PlGF2_{123-144*}$, designed in SEQ ID NO: 47. This protein may be readily made by the artisan reading this specification, as well as other vehicles for other agents or cytokines.

```
SEQ ID NO: 46: human TGF-β3:
ALDTNYCFRNLEENCCVRPLYIDFRQDLGWKWVHEPKGYYANFCSGPCPYLRSADTTH

STVLGLYNTLNPEASASPCCVPQDLEPLTILYYVGRTPKVEQLSNMVVKSCKCS

SEQ ID NO: 47: human PlGF2123-144*-TGF-β3:
RRRPKGRGKRRREKQRPTDSHLALDTNYCFRNLEENCCVRPLYIDFRQDLGWKWVHEP

KGYYANFCSGPCPYLRSADTTHSTVLGLYNTLNPEASASPCCVPQDLEPLTILYYVGRTP

KVEQLSNMVVKSCKCS
```

Further Disclosure

A biologic delivery vehicle comprising a molecular fusion of a biological agent and a peptide comprising a sequence or subsequence of at least 5, or 6, or 7, residues of a sequence chosen from the group consisting of SEQ ID NO: 4 having from 0 to about 15% conservative substitutions and SEQ ID NO:5 having from 0 to about 15% conservative substitutions. Said peptide exhibits specific binding to fibrinogen. 2. The vehicle of 1 with the peptide exhibiting specific binding to fibrinogen, fibronectin, vitronectin, tenascin C, osteopontin, fibrin, and heparan sulfate. 3. The vehicle of 1 or 2 wherein the peptide has a specific binding to fibrinogen with a dissociation constant (Kd) of less than about 24, about 40, or about 100 nM. 4. The vehicle of any of 1-3 wherein the biological agent is chosen from the group consisting of a protein, a protein drug, a marker, an immunoagent, a chemokine, a cytokine, and a cell adhesion peptide. 5. The vehicle of any of 1-4 wherein the molecular fusion comprises a recombinant protein comprising the biologic agent and the peptide. 6. The vehicle of any of 1-4 wherein the molecule fusion comprises a linker covalently bonded with the agent and the peptide. 7. The vehicle of 6 wherein the linker comprises a polymer having a first covalent bond to an N-terminus or a C-terminus of the peptide and a second covalent bond to the biological agent. 8. The vehicle of any of 1-4 wherein the molecule fusion comprises a particle that is joined to the biological agent and to the peptide. 9. The vehicle of 8 wherein the particle is chosen from the group consisting of a microparticle, a nanoparticle, a polymersome, a micelle, and a liposome. 10. The vehicle of 8 being soluble or a colloid in a physiological solution with all components of the vehicle being less than about 500 m in maximum dimension. 11. The vehicle of 8 wherein the particle comprises a plurality of amines and/or thiols that participate in a covalent bond to the biological and/or the peptide. 12. The vehicle of any of 1-11 wherein the biological agent comprises a cytokine chosen from the group consisting of epidermal growth factors (EGFs), VEGFs, VEGF-A, VEGF-C, PDGFs, PDGF-AB, PDGF-BB, FGFs, FGF-2, FGF-18, IGFs, IGF-1, BMPs, BMP-2, BMP-7, TGF-βs, TGF-β1, TGF-β2, TGF-β3, the neurotrophins, NT-3, and BDNF 13. The vehicle of any of 1-11 wherein the biological agent comprises a chemokine chosen from the group consisting of interferons, INF-beta, CXCL chemokines, CXCL10, CXCL11, CXCL12, CCL chemokines, and CCL21 14. The vehicle of any of 1-11 wherein the biological agent comprises an immunoagent 15. The vehicle of 14 wherein the immunoagent provides an antigen. 16. The vehicle of 15 wherein the antigen is at least a portion of tyrosine-related protein 2 (TRP-2). 17. The vehicle of 14 wherein the immunoagent comprises a danger signal 18. The vehicle of 17 wherein the danger signal comprises a globular domain of tenascin or an EDA domain of fibronectin 19. The vehicle of any of 1-11 wherein the biological agent comprises a cell adhesion peptide. 20. The vehicle of 19 wherein the cell adhesion peptide comprises a ligand for a cell surface receptor chosen from the group consisting of integrin and cadherin. 21. The vehicle of 19 wherein the cell adhesion peptide comprises a cell adhesion motif chosen from the group consisting a fibronectin cell adhesion domain, a vitronectin cell adhesion domain, a laminin cell adhesion domain, a tenascin cell adhesion domain, a fibronectin FN III10 domain, a fibronectin FN III9-10 domain, a tenascin domain taken from one or more of a fibronectin type III repeats 1 to 5, a $3^{rd}$ FN type III repeat of tenascin C, a FN III9-10 domain of tenascin, RGD, RGDS (SEQ ID NO: 64), RGDSP (SEQ ID NO: 52), KLDAPT (SEQ ID NO: 66), IDGIHEL (SEQ ID NO: 49), IDAPS (SEQ ID NO: 48), LDV, and REDV (SEQ ID NO: 65). 22. The vehicle of any of 1-11 wherein the biologic agent comprises a protease inhibitor.

23. A biomolecule comprising a cytokine derivatized to include a PlGF2 domain. 24. The biomolecule of 23 wherein an endogenous extracellular-matrix binding domain of the cytokine has been removed or disabled 25. The biomolecule of 23 or 24 wherein the derivatized cytokine has specific binding to an extracellular matrix molecule selected from the group of fibrinogen, fibronectin, vitronectin, tenascin C, osteopontin and fibrin. 26. The biomolecule of 25 wherein the dissociation constant of binding of the derivatized cytokine with the extracellular matrix molecule is less than 50% of a dissociation constant of binding of the underivatized cytokine to the same extracellular matrix molecule. 27. The biomolecule of any of 23-26 wherein the cytokine is selected from the group consisting of epidermal growth factors (EGFs), VEGFs, VEGF-A, VEGF-C, PDGFs, PDGF-AB, PDGF-BB, the FGFs, FGF-2, FGF-18, IGFs, IGF-1, BMPs, BMP-2, BMP-7, TGF-βs, TGF-β1, TGF-β2, TGF-β3, neurotrophins, NT-3, and BDNF. 27. The biomolecule of any of 23-27 wherein the biomolecule is a fusion protein or a molecular fusion that further comprises a biologic agent.

28. An isolated polypeptide comprising a sequence or subsequence of at least 6 residues (or at least 5, or at least 7, or at least 8) of a sequence chosen from the group consisting of SEQ ID NO: 4 having from 0 to about 15% conservative substitutions and SEQ ID NO:5 having from 0 to about 15% conservative substitutions, said peptide exhibiting specific binding to fibrinogen. 29. The polypeptide of 28 further exhibiting specific binding to fibronectin, vitronectin, tenascin C, osteopontin, and fibrin. 30. The polypeptide of 28 or 29 wherein the specific binding of the polypeptide to fibrinogen has a dissociation constant (Kd) of less than about 25 nM. 31. The polypeptide of any of 28-30 wherein the sequence is chosen from the group consisting of SEQ ID NO:4 and SEQ ID NO:5. 32. A fusion protein comprising the polypeptide of any of 28-31.

33. A biomaterial comprising a matrix, with the matrix comprising a peptide comprising a sequence or subsequence of at least 6 residues of a sequence chosen from the group consisting of SEQ ID NO: 4 having from 0 to about 15% conservative substitutions and SEQ ID NO:5 having from 0 to about 15% conservative substitutions, said peptide exhibiting specific binding to the matrix. 34. The biomaterial of 33 wherein the specific binding of the peptide to the matrix has a dissociation constant (Kd) of less than about 100 nM. 35. The biomaterial of 33 wherein the specific binding of the peptide to the matrix has a dissociation constant (Kd) of less than about 25 nM. 36. The biomaterial of any of 33-35 wherein the peptide is specifically bound to the matrix and is available for binding to biomolecules. 37. The biomaterial of 33 or 34 wherein the peptide is free of covalent bonds to the matrix. 38. The biomaterial of any of 33-37 comprising an extracellular matrix domain that specifically binds to the peptide. 39. The biomaterial of 38 wherein the extracellular matrix domain is a domain of a biomolecule chosen from the group consisting of fibrinogen, fibronectin, vitronectin, tenascin C, osteopontin, and fibrin. 40. The biomaterial of any of 33-39 comprising hydrophilic polymers, wherein the peptide is attached to the matrix though a transglutaminase substrate, with a bond being formed by a transglutaminase enzyme between the substrate and the polypeptide. 41. The biomaterial of 40 wherein the polymers or the peptide comprise a transglutaminase substrate that comprises NQEQVSPL (SEQ ID NO:50). 42. The biomaterial of any of 33-41 further comprising a molecular fusion of the peptide and a biologic agent. 43. The biomaterial of 42 wherein the biological agent comprises a cytokine is selected from the group consisting of epidermal growth factors (EGFs), VEGFs, VEGF-A, VEGF-C, PDGFs, PDGF-AB, PDGF-BB, the FGFs, FGF-2, FGF-18, IGFs, IGF-1, BMPs, BMP-2, BMP-7, TGF-βs, TGF-β1, TGF-β2, TGF-β3, neurotrophins, NT-3, and BDNF. 44. The biomaterial of 42 wherein the biological agent comprises a the biological agent comprises a chemokine chosen from the group consisting of interferons, INF-γ, CXCL chemokines, CXCL10, CXCL11, CXCL12, CCL chemokines, and CCL21. 45. The biomaterial of 42 wherein the biological agent comprises an immunoagent. 46. The biomaterial of 42 wherein the immunoagent provides an antigen. 47. The biomaterial of 42 wherein the antigen is at least a portion of tyrosine-related protein 2 (TRP-2). 48. The biomaterial of 42 wherein the immunoagent comprises a danger signal. 49. The biomaterial of 48 wherein the danger signal comprises a globular domain of tenascin or an EDA domain of fibronectin. 50. The biomaterial of 42 wherein the biological agent comprises a cell adhesion peptide. 51. The biomaterial of 42 wherein the cell adhesion peptide comprises a ligand for a cell surface receptor chosen from the group consisting of integrin, cadherin. 52. The biomaterial of 42 wherein the cell adhesion peptide comprises a cell adhesion motif chosen from the group consisting a fibronectin cell adhesion domain, a vitronectin cell adhesion domain, a laminin cell adhesion domain, a tenascin cell adhesion domain, a fibronectin FN III10 domain, a fibronectin FN III9-10 domain, a tenascin domain taken from one or more of a fibronectin type III repeats 1 to 5, a $3^{rd}$ FN type III repeat of tenascin C, a FN III9-10 domain of tenascin, RGD, RGDS (SEQ ID NO: 64), RGDSP (SEQ ID NO: 52), KLDAPT (SEQ ID NO: 66), IDGIHEL (SEQ ID NO: 49), IDAPS (SEQ ID NO: 48), LDV, and REDV (SEQ ID NO: 65). 53. The biomaterial of 42 wherein the biologic agent comprises a protease inhibitor. 54. The biomaterial of any of 28-53 wherein the biologic agent comprises a protease inhibitor. 55. The biomaterial of 54 wherein the protease inhibitor comprises aprotinin and the matrix comprises fibrin. 56. The biomaterial of any of 28-55 further comprising a plurality of molecular fusions, with each of the plurality of the fusions having a distinct biologic agent fused with at least one of the peptides. 57. The biomaterial of 56 comprising between 2 and 10 molecular fusions, with the biologic agent for each of the fusions being independently chosen. 58. The biomaterial of 57 wherein the plurality of molecular fusions have a biologic agent independently chosen from the group consisting of epidermal growth factors (EGFs), VEGFs, VEGF-A, VEGF-C, PDGFs, PDGF-AB, PDGF-BB, FGFs, FGF-2, FGF-18, IGFs, IGF-1, BMPs, BMP-2, BMP-7, TGF-βs, TGF-β1, TGF-β2, TGF-β3, the neurotrophins, NT-3, BDNF, interferon-β, interferons, CXCL chemokines, CXCL10, CXCL11, CXCL12, CCL chemokines, and CCL21, a globular domain, a fibronectin cell adhesion domain, a vitronectin cell adhesion domain, a laminin cell adhesion domain, a tenascin cell adhesion domain, a fibronectin FN III10 domain, a fibronectin FN III9-10 domain, a tenascin domain taken from one or more of a fibronectin type III repeats 1 to 5, a $3^{rd}$ FN type III repeat of tenascin C, a FN III9-10 domain of tenascin, RGD, RGDS (SEQ ID NO: 64), RGDSP (SEQ ID NO: 52), KLDAPT (SEQ ID NO: 66), IDGIHEL (SEQ ID NO: 49), IDAPS (SEQ ID NO: 48), LDV, and REDV (SEQ ID NO: 65).

59. A medicament comprising pharmaceutically acceptable vehicle of any of 1-22, the biomolecule of any of 23-27, the polypeptide of any of 28-31, the fusion protein of 32, or the biomaterial of any of 33-58. 60. The medicament of 59 for treating a condition of disease, for wound healing, for bone healing, or for vaccination. 61. The medicament of 59 comprising a plurality of molecular fusions, with each of the plurality of the fusions having a distinct biologic agent fused with at least one of the polypeptides. 62. The medicament of 61 comprising between 2 and 10 molecular fusions, with the biologic agent for each of the fusions being independently chosen. 63. A method of treating a patient with a medicament comprising administering a pharmaceutically acceptable vehicle of any of 1-22, the biomolecule of any of 23-27, the polypeptide of any of 28-31, the fusion protein of 32, or the biomaterial of any of 33-58. 64. A method of treating a patient with a medicament comprising administering a pharmaceutically acceptable molecular fusion of a biological agent and a peptide, or a biomaterial matrix comprising a pharmaceutically acceptable molecular fusion of a biological agent and a peptide, with the polypeptide comprising a sequence or subsequence of at least 6 residues of a sequence chosen from the group consisting of SEQ ID NO: 4 having from 0 to about 15% conservative substitutions and SEQ ID NO:5 having from 0 to about 15% conservative substitutions. 65. The method of 64 wherein the biologic agent provides an antigen, with the patient being vaccinated by administration of the molecule fusion. 66. The method of 64 wherein the agent comprises a danger signal, with an antigen being administered in combination with the agent. 67. The method of 64 wherein the molecular fusion provides for an extended release of the biologic agent from the site of administration. 68. The method of 64 wherein the biologic agent comprises a cytokine, with the site of administration being chosen from the group consisting of a fistula, a wound, and an ulcer. 69. A vaccine comprising any of the embodiments of 1-68. 70. A matrix or system comprising any of the embodiments of 1-69 for drug delivery, vaccination, wound healing, or bone healing. A nucleic acid comprising a sequence encoding a peptide or protein of any of 1-70.

REFERENCES

All references, patents, patent applications, journal articles and publications set forth herein are hereby incorporated by reference herein for all purposes; in case of conflict, the instant specification is controlling.

Affolter M, Basler K (2007). The Decapentaplegic morphogen gradient: from pattern formation to growth regulation. *Nat Rev Genet.* 8:663-674.

Arrighi I, et al. (2009). Bone healing induced by local delivery of an engineered parathyroid hormone prodrug. *Biomaterials* 30:1763-1771.

Berrier A L, Yamada K M (2007). Cell-matrix adhesion. *J Cell Physiol* 213:565-573.

Chan R K, et al. (2006). Effect of recombinant platelet-derived growth factor (Regranex) on wound closure in genetically diabetic mice. *J Burn Care Res* 27:202-205.

Cross M, Dexter T M (1991). Growth factors in development, transformation, and tumorigenesis. *Cell* 64:271-280.

Danen E H, et al. (1995). Requirement for the synergy site for cell adhesion to fibronectin depends on the activation state of integrin alpha 5 beta 1. *J Biol Chem* 270:21612-21618.

Davidson J M (1998). Animal models for wound repair. *Arch Dermatol Res* 290 Suppl:S1-11.

Discher D E, Mooney D J, Zandstra P W (2009). Growth factors, matrices, and forces combine and control stem cells. *Science* 324:1673-1677.

Ferguson M W, et al. (2009). Prophylactic administration of avotermin for improvement of skin scarring: three double-blind, placebo-controlled, phase I/II studies. *Lancet* 373:1264-1274.

Flick M J, et al. (2004). Leukocyte engagement of fibrin (ogen) via the integrin receptor alphaMbeta2/Mac-1 is critical for host inflammatory response in vivo. *J Clin Invest* 113:1596-1606.

Galiano R D, et al. (2004). Topical vascular endothelial growth factor accelerates diabetic wound healing through increased angiogenesis and by mobilizing and recruiting bone marrow-derived cells. *Am J Pathol* 164:1935-1947.

Gautschi O P, Frey S P, Zellweger R (2007). Bone morphogenetic proteins in clinical applications. *ANZ J Surg* 77:626-631.

Golledge J, et al. (2011). The role of tenascin C in cardiovascular disease. *Cardiovasc Res* 92:19-28.

Gurtner G C, Werner S, Barrandon Y, Longaker M T (2008). Wound repair and regeneration. *Nature* 453:314-321.

Hanft J R, et al. (2008). Phase I trial on the safety of topical rhVEGF on chronic neuropathic diabetic foot ulcers. *J Wound Care* 17:30-32, 34-37.

Hantgan R R, Francis C W, Marder V J (1994) Chapter 14: *Fibrinogen structure and physiology* (Lippincott Company, Philadelphia) 3rd Ed.

Hinz B (2009). The myofibroblast: paradigm for a mechanically active cell. *J Biomech*:doi:10.1016/j.jbiomech.2009.1009.1020.

Hollinger J O, Kleinschmidt J C (1990). The critical size defect as an experimental model to test bone repair materials. *J Craniofac Surg* 1:60-68.

Hollinger J O, et al. (2008). Recombinant human platelet-derived growth factor: biology and clinical applications. *J Bone Joint Surg Am* 90 Suppl 1:48-54.

Hubbell J A, Thomas S N, Swartz M A (2009). Materials engineering for immunomodulation. *Nature* 462:449-460.

Imanaka-Yoshida K, et al. (2001). Serial extracellular matrix changes in neointimal lesions of human coronary artery after percutaneous transluminal coronary angioplasty: clinical significance of early tenascin-C expression. *Virchows Arch* 439:185-190.

Janmey P A, Winer J P, Weisel J W (2009). Fibrin gels and their clinical and bioengineering applications. *J R Soc Interface* 6:1-10.

Joester A, Faissner A (2001). The structure and function of tenascins in the nervous system. *Matrix Biol* 20:13-22.

Jones F S, Jones P L (2000). The tenascin family of ECM glycoproteins: structure, function, and regulation during embryonic development and tissue remodeling. *Dev Dyn* 218:235-259.

Krammer A, et al. (2002). A structural model for force regulated integrin binding to fibronectin's RGD-synergy site. *Matrix Biol* 21:139-147.

Lindahl U, Li J P (2009). Interactions between heparan sulfate and proteins-design and functional implications. *Int Rev Cell Molec Biol* 276:105-159.

Lorand L, Graham R M (2003). Transglutaminases: cross-linking enzymes with pleiotropic functions. Nature reviews. *Molecular cell biology* 4:140-156.

Lorentz K M, Kontos S, Frey P, Hubbell J A (2011). Engineered aprotinin for improved stability of fibrin biomaterials. *Biomaterials* 32:430-438.

Makarenkova H P, et al. (2009). Differential interactions of FGFs with heparan sulfate control gradient formation and branching morphogenesis. *Sci Signal* 2:ra55.

Mao Y, Schwarzbauer J E (2005). Fibronectin fibrillogenesis, a cell-mediated matrix assembly process. *Matrix Biol* 24:389-399.

Mardon H J, Grant K E (1994). The role of the ninth and tenth type III domains of human fibronectin in cell adhesion. *FEBS Lett* 340:197-201.

Martino M M, Hubbell J A (2010). The 12th-14th type III repeats of fibronectin function as a highly promiscuous growth factor-binding domain. *Faseb J* 24:4711-4721.

Midwood K, et al. (2009). Tenascin-C is an endogenous activator of Toll-like receptor 4 that is essential for maintaining inflammation in arthritic joint disease. *Nat Med* 15:774-780.

Midwood K S, Hussenet T, Langlois B, Orend G (2011). Advances in tenascin-C biology. *Cell Mol Life Sci* 68:3175-3199.

Moore E E, et al. (2005). Fibroblast growth factor-18 stimulates chondrogenesis and cartilage repair in a rat model of injury-induced osteoarthritis. *Osteoarthritis Cartilage* 13:623-631.

Mosesson M W (2005). Fibrinogen and fibrin structure and functions. *J Thromb Haemost* 3:1894-1904.

Mould A P, et al. (1997). Defining the topology of integrin alpha5beta1-fibronectin interactions using inhibitory anti-alpha5 and anti-beta1 monoclonal antibodies. Evidence that the synergy sequence of fibronectin is recognized by the amino-terminal repeats of the alpha5 subunit. *J Biol Chem* 272:17283-17292.

Muschler G F, et al. The design and use of animal models for translational research in bone tissue engineering and regenerative medicine. *Tissue Eng Part B Rev* 16:123-145.

O'Connell J T, et al. (2011). VEGF-A and Tenascin-C produced by S100A4+ stromal cells are important for metastatic colonization. *Proc Natl Acad Sci USA* 108: 16002-16007.

Orend G (2005). Potential oncogenic action of tenascin-C in tumorigenesis. *Int J Biochem Cell Biol* 37:1066-1083.

Oskarsson T, et al. (2011). Breast cancer cells produce tenascin C as a metastatic niche component to colonize the lungs. *Nat Med* 17:867-874.

Pankov R, Yamada K M (2002). Fibronectin at a glance. *J Cell Sci* 115:3861-3863.

Patterson J, Martino M M, Hubbell J A (2010). Biomimetic materials in tissue engineering. *Mater Today* 13:14-22.

Peng H, et al. (2004). Identification of a binding site on human FGF-2 for fibrinogen. *Blood* 103:2114-2120.

Peng Q, et al. (2009). Mechanical design of the third FnIII domain of tenascin-C. *J Mol Biol* 386:1327-1342.

Ribatti D (2008). The discovery of the placental growth factor and its role in angiogenesis: a historical review. *Angiogenesis* 11:215-221.

Robson M C, et al. (1992). The safety and effect of topically applied recombinant basic fibroblast growth factor on the healing of chronic pressure sores. *Ann Surg* 216:401-406; discussion 406-408.

Robson M C, et al. (1992). Platelet-derived growth factor BB for the treatment of chronic pressure ulcers. *Lancet* 339:23-25.

Robson M C, et al. (2001). Randomized trial of topically applied repifermin (recombinant human keratinocyte growth factor-2) to accelerate wound healing in venous ulcers. *Wound Repair Regen* 9:347-352.

Rossi D, Zlotnik A (2000). The biology of chemokines and their receptors. *Annu Rev Immunol* 18:217-242.

Sahni A, Odrljin T, Francis C W (1998). Binding of basic fibroblast growth factor to fibrinogen and fibrin. *Journal of Biological Chemistry* 273:7554-7559.

Sahni A, et al. (2006). FGF-2 binding to fibrin(ogen) is required for augmented angiogenesis. *Blood* 107:126-131.

Sakiyama S E, Schense J C, Hubbell J A (1999). Incorporation of heparin-binding peptides into fibrin gels enhances neurite extension: an example of designer matrices in tissue engineering. *Faseb J* 13:2214-2224.

Schense J C, Hubbell J A (1999). Cross-linking exogenous bifunctional peptides into fibrin gels with factor XIIIa. *Bioconjug Chem* 10:75-81.

Schmoekel H G, et al. (2005). Bone repair with a form of BMP-2 engineered for incorporation into fibrin cell ingrowth matrices. *Biotechnol Bioeng* 89:253-262.

Schultz G S, Wysocki A (2009). Interactions between extracellular matrix and growth factors in wound healing. *Wound Repair Regen* 17:153-162.

Sierro S R, et al. (2011). Combination of lentivector immunization and low-dose chemotherapy or PD-1/PD-L1 blocking primes self-reactive T cells and induces anti-tumor immunity. *Eur J Immunol* 41:2217-2228.

Standeven K F, et al. (2007). Functional analysis of fibrin {gamma}-chain cross-linking by activated factor XIII: determination of a cross-linking pattern that maximizes clot stiffness. *Blood* 110:902-907.

Sullivan S R, et al. (2004). Validation of a model for the study of multiple wounds in the diabetic mouse (db/db). *Plast Reconstr Surg* 113:953-960.

Trebaul A, Chan E K, Midwood K S (2007). Regulation of fibroblast migration by tenascin-C. *Biochem Soc Trans* 35:695-697.

Udalova I A, Ruhmann M, Thomson S J, Midwood K S (2011). Expression and immune function of tenascin-C. *Crit. Rev Immunol* 31:115-145.

Ugarova T P, Yakubenko V P (2001). Recognition of fibrinogen by leukocyte integrins. *Ann N Y Acad Sci* 936:368-385.

Vilcek J, Feldmann M (2004). Historical review: Cytokines as therapeutics and targets of therapeutics. *Trends Pharmacol Sci* 25:201-209.

Weber P, Zimmermann D R, Winterhalter K H, Vaughan L (1995). Tenascin-C binds heparin by its fibronectin type III domain five. *J Biol Chem* 270:4619-4623.

Weisel J W (2004). The mechanical properties of fibrin for basic scientists and clinicians. *Biophys Chem* 112:267-276.

Weisel J W (2007). Structure of fibrin: impact on clot stability. *J Thromb Haemost* 5 Suppl 1:116-124.

Werner S, Grose R (2003). Regulation of wound healing by growth factors and cytokines. *Physiol Rev* 83:835-870.

Yokosaki Y, et al. (1998). Identification of the ligand binding site for the integrin alpha9 beta1 in the third fibronectin type III repeat of tenascin-C. *The Journal of biological chemistry* 273:11423-11428.

Kilarski W W, et al. (2013). Intravital immunofluorescence for visualizing the microcirculatory and immune microenvironments in the mouse ear dermis. PLoS One 8:e57135.

Lasarte J J, et al. (2007). The extra domain A from fibronectin targets antigens to TLR4-expressing cells and induces cytotoxic T cell responses in vivo. *J Immunol* 178:748-756.

Mansilla C, et al. (2009). Immunization against hepatitis C virus with a fusion protein containing the extra domain A from fibronectin and the hepatitis C virus NS3 protein. *J Hepatol* 51:520-527.

Migdal M, et al. (1998). Neuropilin-1 is a placenta growth factor-2 receptor. *J Biol Chem* 273:22272-22278.

Pan Q, et al. (2007). Neuropilin-1 binds to VEGF121 and regulates endothelial cell migration and sprouting. *J Biol Chem* 282:24049-24056.

Simons M, Ware J A (2003). Therapeutic angiogenesis in cardiovascular disease. *Nat Rev Drug Discov* 2:863-871.

Whitaker G B, Limberg B J, Rosenbaum J S (2001). Vascular endothelial growth factor receptor-2 and neuropilin-1 form a receptor complex that is responsible for the differential signaling potency of VEGF(165) and VEGF (121). *J Biol Chem* 276:25520-25531.

The invention claimed is:

1. A biologic delivery vehicle comprising
a molecular fusion of a cytokine that comprises a first endogenous heparin binding domain (HBD) and a peptide,
wherein the cytokine is selected from the group consisting of a Vascular Endothelial Growth Factor (VEGF) that comprises an endogenous HBD that provides said first HBD, an Epidermal Growth Factor (EGF) that comprises an endogenous HBD that provides said first HBD, a Platelet-Derived Growth Factor (PDGF) that comprises an endogenous HBD that provides said first HBD, a Fibroblast Growth Factor (FGF) that comprises an endogenous HBD that provides said first HBD, a Transforming Growth Factor-Beta (TGF-β) that comprises an endogenous HBD that provides said first HBD, and a Bone Morphogenetic Protein (BMP) that comprises an endogenous HBD that provides said first HBD,
wherein the peptide consists of a second heparin binding domain having a sequence chosen from the group consisting of SEQ ID NO: 1, SEQ ID NO: 2, SEQ ID NO: 3, SEQ ID NO: 4, SEQ ID NO:5, SEQ ID NO: 60, and SEQ ID NO: 62, said peptide exhibiting specific binding to fibrinogen,
with the biomolecule being free of wild-type full-length PlGF2.

2. The vehicle of claim 1 wherein the molecular fusion comprises
a recombinant protein comprising the cytokine and the peptide;
a linker covalently bonded with the cytokine and the peptide; or
a particle that is joined to the cytokine and to the peptide.

3. The vehicle of claim 2 being soluble or a colloid in a physiological solution with all components of the vehicle being less than about 500 µm in maximum dimension.

4. The vehicle of claim 1 wherein the cytokine that has an endogenous HBD that provides said first HBD comprises VEGF-A, PDGF-AB, PDGF-BB, FGF-2, FGF-18, BMP-2, BMP-7, TGF-β1, or TGF-β2.

5. A biomolecule comprising
a cytokine that comprises a first endogenous heparin binding domain (HBD) and a PlGF2 domain that comprises a second heparin binding domain, wherein the cytokine is selected from the group consisting of a Vascular Endothelial Growth Factor (VEGF) that comprises an endogenous HBD that provides said first HBD, an Epidermal Growth Factor (EGF) that comprises an endogenous HBD that provides said first HBD, a Platelet-Derived Growth Factor (PDGF) that comprises an endogenous HBD that provides said first HBD, a Fibroblast Growth Factor (FGF) that comprises an endogenous HBD that provides said first HBD, a Transforming Growth Factor-Beta (TGF-β) that comprises an endogenous HBD that provides said first HBD, and a Bone Morphogenetic Protein (BMP) that comprises an endogenous HBD that provides said first HBD,
wherein the PlGF2 domain that comprises the second heparin binding domain consists of a sequence chosen from the group consisting of SEQ ID NO: 1, SEQ ID NO: 2, SEQ ID NO: 3, SEQ ID NO: 4, SEQ ID NO: 5, SEQ ID NO: 60, and SEQ ID NO: 62,
with the biomolecule being free of wild-type full-length PlGF2.

6. The biomolecule of claim 5 wherein the endogenous HBD of the cytokine has been removed or disabled.

7. The biomolecule of claim 5 wherein the cytokine is selected from the group consisting of VEGF-A, PDGF-AB, PDGF-BB, FGF-2, FGF-18, BMP-2, BMP-7, TGF-β1, and TGF-β2.

8. The biomolecule of claim 5 further comprising another biological agent.

9. A fusion protein comprising the biomolecule of claim 5.

10. A biomaterial comprising a matrix, with the matrix comprising
a peptide chosen from the group consisting of SEQ ID NO: 1, SEQ ID NO: 2, SEQ ID NO: 3, SEQ ID NO: 4 SEQ ID NO: 5, SEQ ID NO: 60, and SEQ ID NO: 62,
said peptide exhibiting specific binding to the matrix,
wherein the biomaterial is free of wild-type full-length PlGF2.

11. The biomaterial of claim 10 wherein the peptide is specifically bound to the matrix and is available for binding to biomolecules.

12. The biomaterial of claim 10 comprising a plurality of molecular fusions that each comprise one or more of the peptides, with each of the plurality of the molecular fusions having a distinct biologic agent.

13. A method of promoting wound healing in a patient need thereof, said method comprising administering a medicament comprising the biomolecule of claim 5 to the patient.

14. The method of claim 13 wherein the biomolecule provides for an extended release of the peptide.

15. The method of claim 13, with a site of administration of the medicament being chosen from the group consisting of a wound and skin.

16. A method of treating a bone defect in a patient in need thereof, said method comprising administering a medicament comprising the biologic delivery vehicle of claim 1 to the patient.

17. The vehicle of claim 1 with the second heparin binding domain consisting of SEQ ID NO: 4.

18. A method of treating a bone defect in a patient in need thereof, said method comprising administering a medicament comprising the biologic delivery vehicle of claim 17 to the patient.

19. A method of promoting wound healing in a patient in need thereof, said method comprising administering a medicament comprising the biomaterial of claim 10 to the patient.

20. The vehicle of claim 1 wherein the cytokine is VEGF-A165, PDGF-BB, BMP-2, TGF-β1, or TGF-β2.

21. The vehicle of claim 1 wherein the cytokine comprises VEGF-A.

22. The vehicle of claim 1 wherein the cytokine comprises VEGF.

23. The vehicle of claim 1 wherein the cytokine comprises BMP-2 or PDGF-BB.

24. The biomolecule of claim 5 wherein the cytokine is VEGF-A165, PDGF-BB, BMP-2, TGF-β1, or TGF-β2.

25. The biomolecule of claim 5 wherein the cytokine comprises VEGF-A.

26. The biomolecule of claim 5 wherein the cytokine comprises BMP-2 or PDGF-BB.

27. The method of claim 16, with a site of administration of the medicament being bone.

28. The method of claim 19, with a site of administration of the medicament being chosen from the group consisting of a wound skin.

* * * * *

SEQUENCE LISTING

```
<160> NUMBER OF SEQ ID NOS: 66

<210> SEQ ID NO 1
<211> LENGTH: 15
<212> TYPE: PRT
<213> ORGANISM: artificial
<220> FEATURE:
<223> OTHER INFORMATION: Portion of GST-PlGF2 fusion

<400> SEQUENCE: 1

Arg Arg Arg Pro Lys Gly Arg Gly Lys Arg Arg Glu Lys Gln
1               5                   10                  15

<210> SEQ ID NO 2
<211> LENGTH: 8
<212> TYPE: PRT
<213> ORGANISM: Artificial
<220> FEATURE:
<223> OTHER INFORMATION: GSP-PlGF2 fragment

<400> SEQUENCE: 2

Gly Lys Arg Arg Arg Glu Lys Gln
1               5

<210> SEQ ID NO 3
<211> LENGTH: 8
<212> TYPE: PRT
<213> ORGANISM: Artificial
<220> FEATURE:
<223> OTHER INFORMATION: GSP_PlGF2 fragment

<400> SEQUENCE: 3

Arg Arg Arg Pro Lys Gly Arg Gly
1               5

<210> SEQ ID NO 4
<211> LENGTH: 22
<212> TYPE: PRT
<213> ORGANISM: Artificial
<220> FEATURE:
<223> OTHER INFORMATION: Portion of human PlGF2

<400> SEQUENCE: 4

Arg Arg Arg Pro Lys Gly Arg Gly Lys Arg Arg Glu Lys Gln Arg
1               5                   10                  15

Pro Thr Asp Cys His Leu
            20
```

-continued

```
<210> SEQ ID NO 5
<211> LENGTH: 21
<212> TYPE: PRT
<213> ORGANISM: artificial
<220> FEATURE:
<223> OTHER INFORMATION: poretion of mouse PlGF2.

<400> SEQUENCE: 5

Arg Arg Lys Thr Lys Gly Lys Arg Lys Ser Arg Asn Ser Gln Thr
1               5                   10                  15

Glu Glu Pro His Pro
            20

<210> SEQ ID NO 6
<211> LENGTH: 120
<212> TYPE: PRT
<213> ORGANISM: Artificial
<220> FEATURE:
<223> OTHER INFORMATION: portion of human VEGF-A121

<400> SEQUENCE: 6

Ala Pro Met Ala Glu Gly Gly Gln Asn His His Glu Val Val Lys
1               5                   10                  15

Phe Met Asp Val Tyr Gln Arg Ser Tyr Cys His Pro Ile Glu Thr Leu
            20                  25                  30

Val Asp Ile Phe Gln Glu Tyr Pro Asp Glu Ile Glu Tyr Ile Phe Lys
        35                  40                  45

Pro Ser Cys Val Pro Leu Met Arg Cys Gly Gly Cys Cys Asn Asp Glu
    50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg Ala Arg
            100                 105                 110

Gln Glu Cys Asp Lys Pro Arg Arg
        115                 120

<210> SEQ ID NO 7
<211> LENGTH: 142
<212> TYPE: PRT
<213> ORGANISM: artificial
<220> FEATURE:
<223> OTHER INFORMATION: fusion protein of VEGF-A121 and PlGF2 domain

<400> SEQUENCE: 7

Ala Pro Met Ala Glu Gly Gly Gly Gln Asn His His Glu Val Val Lys
1               5                   10                  15

Phe Met Asp Val Tyr Gln Arg Ser Tyr Cys His Pro Ile Glu Thr Leu
            20                  25                  30

Val Asp Ile Phe Gln Glu Tyr Pro Asp Glu Ile Glu Tyr Ile Phe Lys
        35                  40                  45

Pro Ser Cys Val Pro Leu Met Arg Cys Gly Gly Cys Cys Asn Asp Glu
    50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg Ala Arg
            100                 105                 110
```

```
Gln Glu Arg Arg Arg Pro Lys Gly Arg Gly Lys Arg Arg Glu Lys
        115                 120                 125

Gln Arg Pro Thr Asp Cys His Leu Cys Asp Lys Pro Arg Arg
        130                 135                 140

<210> SEQ ID NO 8
<211> LENGTH: 109
<212> TYPE: PRT
<213> ORGANISM: Artificial
<220> FEATURE:
<223> OTHER INFORMATION: portion of human PDGF

<400> SEQUENCE: 8

Ser Leu Gly Ser Leu Thr Ile Ala Glu Pro Ala Met Ile Ala Glu Cys
1               5                   10                  15

Lys Thr Arg Thr Glu Val Phe Glu Ile Ser Arg Arg Leu Ile Asp Arg
            20                  25                  30

Thr Asn Ala Asn Phe Leu Val Trp Pro Pro Cys Val Glu Val Gln Arg
        35                  40                  45

Cys Ser Gly Cys Cys Asn Asn Arg Asn Val Gln Cys Arg Pro Thr Gln
    50                  55                  60

Val Gln Leu Arg Pro Val Gln Val Arg Lys Ile Glu Ile Val Arg Lys
65                  70                  75                  80

Lys Pro Ile Phe Lys Lys Ala Thr Val Thr Leu Glu Asp His Leu Ala
                85                  90                  95

Cys Lys Cys Glu Thr Val Ala Ala Ala Arg Pro Val Thr
            100                 105

<210> SEQ ID NO 9
<211> LENGTH: 131
<212> TYPE: PRT
<213> ORGANISM: homo sapiens

<400> SEQUENCE: 9

Ser Leu Gly Ser Leu Thr Ile Ala Glu Pro Ala Met Ile Ala Glu Cys
1               5                   10                  15

Lys Thr Arg Thr Glu Val Phe Glu Ile Ser Arg Arg Leu Ile Asp Arg
            20                  25                  30

Thr Asn Ala Asn Phe Leu Val Trp Pro Pro Cys Val Glu Val Gln Arg
        35                  40                  45

Cys Ser Gly Cys Cys Asn Asn Arg Asn Val Gln Cys Arg Pro Thr Gln
    50                  55                  60

Val Gln Leu Arg Pro Val Gln Val Arg Lys Ile Glu Ile Val Arg Lys
65                  70                  75                  80

Lys Pro Ile Phe Lys Lys Ala Thr Val Thr Leu Glu Asp His Leu Ala
                85                  90                  95

Cys Lys Cys Glu Thr Val Ala Ala Ala Arg Pro Val Thr Arg Arg
            100                 105                 110

Pro Lys Gly Arg Gly Lys Arg Arg Glu Lys Gln Arg Pro Thr Asp
        115                 120                 125

Cys His Leu
    130

<210> SEQ ID NO 10
<211> LENGTH: 114
<212> TYPE: PRT
<213> ORGANISM: Homo sapiens
```

```
<400> SEQUENCE: 10

Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Val Ala Pro Pro Gly Tyr His Ala Phe Tyr Cys His Gly Glu Cys Pro
        35                  40                  45

Phe Pro Leu Ala Asp His Leu Asn Ser Thr Asn His Ala Ile Val Gln
    50                  55                  60

Thr Leu Val Asn Ser Val Asn Ser Lys Ile Pro Lys Ala Cys Cys Val
65                  70                  75                  80

Pro Thr Glu Leu Ser Ala Ile Ser Met Leu Tyr Leu Asp Glu Asn Glu
                85                  90                  95

Lys Val Val Leu Lys Asn Tyr Gln Asp Met Val Val Glu Gly Cys Gly
            100                 105                 110

Cys Arg

<210> SEQ ID NO 11
<211> LENGTH: 135
<212> TYPE: PRT
<213> ORGANISM: artificial
<220> FEATURE:
<223> OTHER INFORMATION: fusion protein of BMP-2 and PlGF2 domain

<400> SEQUENCE: 11

Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Val Ala Pro Pro Gly Tyr His Ala Phe Tyr Cys His Gly Glu Cys Pro
        35                  40                  45

Phe Pro Leu Ala Asp His Leu Asn Ser Thr Asn His Ala Ile Val Gln
    50                  55                  60

Thr Leu Val Asn Ser Val Asn Ser Lys Ile Pro Lys Ala Cys Cys Val
65                  70                  75                  80

Pro Thr Glu Leu Ser Ala Ile Ser Met Leu Tyr Leu Asp Glu Asn Glu
                85                  90                  95

Lys Val Val Leu Lys Asn Tyr Gln Asp Met Val Val Glu Gly Cys Gly
            100                 105                 110

Cys Arg Arg Arg Pro Lys Gly Arg Gly Lys Arg Arg Arg Glu Lys Gln
            115                 120                 125

Arg Pro Thr Asp Cys His Leu
        130                 135

<210> SEQ ID NO 12
<211> LENGTH: 124
<212> TYPE: PRT
<213> ORGANISM: artificial
<220> FEATURE:
<223> OTHER INFORMATION: fusion protein of BMP-2 and PlGF2 domain

<400> SEQUENCE: 12

Arg Arg Arg Pro Lys Gly Arg Gly Lys Arg Arg Arg Glu Lys Gln Arg
1               5                   10                  15

Pro Thr Asp Cys His Leu Ser Cys Lys Arg His Pro Leu Tyr Val Asp
            20                  25                  30

Phe Ser Asp Val Gly Trp Asn Asp Trp Ile Val Ala Pro Pro Gly Tyr
```

```
                35                  40                  45
His Ala Phe Tyr Cys His Gly Glu Cys Pro Phe Pro Leu Ala Asp His
         50                  55                  60

Leu Asn Ser Thr Asn His Ala Ile Val Gln Thr Leu Val Asn Ser Val
 65                  70                  75                  80

Asn Ser Lys Ile Pro Lys Ala Cys Cys Val Pro Thr Glu Leu Ser Ala
                 85                  90                  95

Ile Ser Met Leu Tyr Leu Asp Glu Asn Glu Lys Val Val Leu Lys Asn
            100                 105                 110

Tyr Gln Asp Met Val Val Glu Gly Cys Gly Cys Arg
        115                 120

<210> SEQ ID NO 13
<211> LENGTH: 135
<212> TYPE: PRT
<213> ORGANISM: artificial
<220> FEATURE:
<223> OTHER INFORMATION: fusion protein of BMP-2 and PlGF2 domain

<400> SEQUENCE: 13

Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Val Ala Pro Pro Gly Tyr His Ala Phe Tyr Cys His Gly Glu Cys Pro
        35                  40                  45

Phe Pro Leu Ala Asp His Leu Asn Ser Thr Asn His Ala Ile Val Gln
 50                  55                  60

Thr Leu Val Asn Ser Val Asn Ser Lys Ile Pro Lys Ala Cys Cys Val
 65                  70                  75                  80

Pro Thr Glu Leu Ser Ala Ile Ser Met Leu Tyr Leu Asp Glu Asn Glu
                 85                  90                  95

Lys Val Val Leu Lys Asn Tyr Gln Asp Met Val Val Glu Gly Cys Gly
            100                 105                 110

Cys Arg Arg Arg Pro Lys Gly Arg Gly Lys Arg Arg Arg Glu Lys Gln
        115                 120                 125

Arg Pro Thr Asp Ser His Leu
        130                 135

<210> SEQ ID NO 14
<211> LENGTH: 70
<212> TYPE: PRT
<213> ORGANISM: homo sapiens

<400> SEQUENCE: 14

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
 50                  55                  60

Lys Pro Ala Lys Ser Ala
 65                  70

<210> SEQ ID NO 15
```

-continued

<211> LENGTH: 92
<212> TYPE: PRT
<213> ORGANISM: artificial
<220> FEATURE:
<223> OTHER INFORMATION: fusion protein of IGF-I and PlGF2 domain

<400> SEQUENCE: 15

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
    50                  55                  60

Lys Pro Ala Lys Ser Ala Arg Arg Pro Lys Gly Arg Gly Lys Arg
65                  70                  75                  80

Arg Arg Glu Lys Gln Arg Pro Thr Asp Cys His Leu
                85                  90

<210> SEQ ID NO 16
<211> LENGTH: 112
<212> TYPE: PRT
<213> ORGANISM: homo sapiens

<400> SEQUENCE: 16

Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Trp Lys Trp
            20                  25                  30

Ile His Glu Pro Lys Gly Tyr His Ala Asn Phe Cys Leu Gly Pro Cys
        35                  40                  45

Pro Tyr Ile Trp Ser Leu Asp Thr Gln Tyr Ser Lys Val Leu Ala Leu
    50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110

<210> SEQ ID NO 17
<211> LENGTH: 134
<212> TYPE: PRT
<213> ORGANISM: artificial
<220> FEATURE:
<223> OTHER INFORMATION: fusion protein of TGF beta and PlGF2 domain

<400> SEQUENCE: 17

Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Trp Lys Trp
            20                  25                  30

Ile His Glu Pro Lys Gly Tyr His Ala Asn Phe Cys Leu Gly Pro Cys
        35                  40                  45

Pro Tyr Ile Trp Ser Leu Asp Thr Gln Tyr Ser Lys Val Leu Ala Leu
    50                  55                  60

Tyr Asn Gln His Asn Pro Gly Ala Ser Ala Ala Pro Cys Cys Val Pro
65                  70                  75                  80

```
Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110

Arg Arg Arg Pro Lys Gly Arg Gly Lys Arg Arg Glu Lys Gln Arg
        115                 120                 125

Pro Thr Asp Cys His Leu
    130

<210> SEQ ID NO 18
<211> LENGTH: 134
<212> TYPE: PRT
<213> ORGANISM: artificial
<220> FEATURE:
<223> OTHER INFORMATION: fusion of PlGf2 and TGF beta

<400> SEQUENCE: 18

Arg Arg Arg Pro Lys Gly Arg Gly Lys Arg Arg Glu Lys Gln Arg
1               5                   10                  15

Pro Thr Asp Ser His Leu Ala Leu Asp Thr Asn Tyr Cys Phe Ser Ser
            20                  25                  30

Thr Glu Lys Asn Cys Cys Val Arg Gln Leu Tyr Ile Asp Phe Arg Lys
        35                  40                  45

Asp Leu Gly Trp Lys Trp Ile His Glu Pro Lys Gly Tyr His Ala Asn
    50                  55                  60

Phe Cys Leu Gly Pro Cys Pro Tyr Ile Trp Ser Leu Asp Thr Gln Tyr
65                  70                  75                  80

Ser Lys Val Leu Ala Leu Tyr Asn Gln His Asn Pro Gly Ala Ser Ala
                85                  90                  95

Ala Pro Cys Cys Val Pro Gln Ala Leu Glu Pro Leu Pro Ile Val Tyr
            100                 105                 110

Tyr Val Gly Arg Lys Pro Lys Val Glu Gln Leu Ser Asn Met Ile Val
        115                 120                 125

Arg Ser Cys Lys Cys Ser
    130

<210> SEQ ID NO 19
<211> LENGTH: 112
<212> TYPE: PRT
<213> ORGANISM: homo sapiens

<400> SEQUENCE: 19

Ala Leu Asp Ala Ala Tyr Cys Phe Arg Asn Val Gln Asp Asn Cys Cys
1               5                   10                  15

Leu Arg Pro Leu Tyr Ile Asp Phe Lys Arg Asp Leu Gly Trp Lys Trp
            20                  25                  30

Ile His Glu Pro Lys Gly Tyr Asn Ala Asn Phe Cys Ala Gly Ala Cys
        35                  40                  45

Pro Tyr Leu Trp Ser Ser Asp Thr Gln His Ser Arg Val Leu Ser Leu
    50                  55                  60

Tyr Asn Thr Ile Asn Pro Glu Ala Ser Ala Ser Pro Cys Cys Val Ser
65                  70                  75                  80

Gln Asp Leu Glu Pro Leu Thr Ile Leu Tyr Tyr Ile Gly Lys Thr Pro
                85                  90                  95

Lys Ile Glu Gln Leu Ser Asn Met Ile Val Lys Ser Cys Lys Cys Ser
            100                 105                 110
```

<210> SEQ ID NO 20
<211> LENGTH: 134
<212> TYPE: PRT
<213> ORGANISM: artificial
<220> FEATURE:
<223> OTHER INFORMATION: fusion protein of human PlGF2 and TGF beta 2

<400> SEQUENCE: 20

Arg Arg Arg Pro Lys Gly Arg Gly Lys Arg Arg Glu Lys Gln Arg
1               5                   10                  15

Pro Thr Asp Ser His Leu Ala Leu Asp Ala Ala Tyr Cys Phe Arg Asn
                20                  25                  30

Val Gln Asp Asn Cys Cys Leu Arg Pro Leu Tyr Ile Asp Phe Lys Arg
            35                  40                  45

Asp Leu Gly Trp Lys Trp Ile His Glu Pro Lys Gly Tyr Asn Ala Asn
        50                  55                  60

Phe Cys Ala Gly Ala Cys Pro Tyr Leu Trp Ser Ser Asp Thr Gln His
65                  70                  75                  80

Ser Arg Val Leu Ser Leu Tyr Asn Thr Ile Asn Pro Glu Ala Ser Ala
                85                  90                  95

Ser Pro Cys Cys Val Ser Gln Asp Leu Glu Pro Leu Thr Ile Leu Tyr
            100                 105                 110

Tyr Ile Gly Lys Thr Pro Lys Ile Glu Gln Leu Ser Asn Met Ile Val
        115                 120                 125

Lys Ser Cys Lys Cys Ser
        130

<210> SEQ ID NO 21
<211> LENGTH: 119
<212> TYPE: PRT
<213> ORGANISM: homo sapiens

<400> SEQUENCE: 21

His Ser Asp Pro Ala Arg Arg Gly Glu Leu Ser Val Cys Asp Ser Ile
1               5                   10                  15

Ser Glu Trp Val Thr Ala Ala Asp Lys Lys Thr Ala Val Asp Met Ser
                20                  25                  30

Gly Gly Thr Val Thr Val Leu Glu Lys Val Pro Val Ser Lys Gly Gln
            35                  40                  45

Leu Lys Gln Tyr Phe Tyr Glu Thr Lys Cys Asn Pro Met Gly Tyr Thr
        50                  55                  60

Lys Glu Gly Cys Arg Gly Ile Asp Lys Arg His Trp Asn Ser Gln Cys
65                  70                  75                  80

Arg Thr Thr Gln Ser Tyr Val Arg Ala Leu Thr Met Asp Ser Lys Lys
                85                  90                  95

Arg Ile Gly Trp Arg Phe Ile Arg Ile Asp Thr Ser Cys Val Cys Thr
            100                 105                 110

Leu Thr Ile Lys Arg Gly Arg
        115

<210> SEQ ID NO 22
<211> LENGTH: 140
<212> TYPE: PRT
<213> ORGANISM: artificial
<220> FEATURE:
<223> OTHER INFORMATION: fusion protein of BDNF and PlGF2 domain

<400> SEQUENCE: 22

```
His Ser Asp Pro Ala Arg Arg Gly Glu Leu Ser Val Cys Asp Ser Ile
1               5                   10                  15

Ser Glu Trp Val Thr Ala Ala Asp Lys Lys Thr Ala Val Asp Met Ser
            20                  25                  30

Gly Gly Thr Val Thr Val Leu Glu Lys Val Pro Val Ser Lys Gly Gln
            35                  40                  45

Leu Lys Gln Tyr Phe Tyr Glu Thr Lys Cys Asn Pro Met Gly Tyr Thr
    50                  55                  60

Lys Glu Gly Cys Arg Gly Ile Asp Lys Arg His Trp Asn Ser Gln Cys
65                  70                  75                  80

Arg Thr Thr Gln Ser Tyr Val Arg Ala Leu Thr Met Asp Ser Lys Lys
                85                  90                  95

Arg Ile Gly Trp Arg Phe Ile Arg Ile Asp Thr Ser Cys Val Cys Thr
            100                 105                 110

Leu Thr Ile Lys Arg Gly Arg Arg Pro Lys Gly Arg Gly Lys Arg
            115                 120                 125

Arg Arg Glu Lys Gln Arg Pro Thr Asp Cys His Leu
130                 135                 140
```

```
<210> SEQ ID NO 23
<211> LENGTH: 119
<212> TYPE: PRT
<213> ORGANISM: homo sapiens

<400> SEQUENCE: 23

Tyr Ala Glu His Lys Ser His Arg Gly Glu Tyr Ser Val Cys Asp Ser
1               5                   10                  15

Glu Ser Leu Trp Val Thr Asp Lys Ser Ser Ala Ile Asp Ile Arg Gly
            20                  25                  30

His Gln Val Thr Val Leu Gly Glu Ile Lys Thr Gly Asn Ser Pro Val
            35                  40                  45

Lys Gln Tyr Phe Tyr Glu Thr Arg Cys Lys Glu Ala Arg Pro Val Lys
    50                  55                  60

Asn Gly Cys Arg Gly Ile Asp Asp Lys His Trp Asn Ser Gln Cys Lys
65                  70                  75                  80

Thr Ser Gln Thr Tyr Val Arg Ala Leu Thr Ser Glu Asn Asn Lys Leu
                85                  90                  95

Val Gly Trp Arg Trp Ile Arg Ile Asp Thr Ser Cys Val Cys Ala Leu
            100                 105                 110

Ser Arg Lys Ile Gly Arg Thr
            115
```

```
<210> SEQ ID NO 24
<211> LENGTH: 141
<212> TYPE: PRT
<213> ORGANISM: artificial
<220> FEATURE:
<223> OTHER INFORMATION: fusion protein of NT-3 and PlGF2 domain

<400> SEQUENCE: 24

Tyr Ala Glu His Lys Ser His Arg Gly Glu Tyr Ser Val Cys Asp Ser
1               5                   10                  15

Glu Ser Leu Trp Val Thr Asp Lys Ser Ser Ala Ile Asp Ile Arg Gly
            20                  25                  30

His Gln Val Thr Val Leu Gly Glu Ile Lys Thr Gly Asn Ser Pro Val
            35                  40                  45

Lys Gln Tyr Phe Tyr Glu Thr Arg Cys Lys Glu Ala Arg Pro Val Lys
```

```
                50                  55                  60
Asn Gly Cys Arg Gly Ile Asp Asp Lys His Trp Asn Ser Gln Cys Lys
 65                  70                  75                  80

Thr Ser Gln Thr Tyr Val Arg Ala Leu Thr Ser Glu Asn Asn Lys Leu
                 85                  90                  95

Val Gly Trp Arg Trp Ile Arg Ile Asp Thr Ser Cys Val Cys Ala Leu
                100                 105                 110

Ser Arg Lys Ile Gly Arg Thr Arg Arg Pro Lys Gly Arg Gly Lys
            115                 120                 125

Arg Arg Arg Glu Lys Gln Arg Pro Thr Asp Cys His Leu
130                 135                 140
```

<210> SEQ ID NO 25
<211> LENGTH: 206
<212> TYPE: PRT
<213> ORGANISM: artificial
<220> FEATURE:
<223> OTHER INFORMATION: fusion protein of FN119 domain and PlGF2 domain

<400> SEQUENCE: 25

```
Gly Leu Asp Ser Pro Thr Gly Ile Asp Phe Ser Asp Ile Thr Ala Asn
 1               5                  10                  15

Ser Phe Thr Val His Trp Ile Ala Pro Arg Ala Thr Ile Thr Gly Tyr
                20                  25                  30

Arg Ile Arg His His Pro Glu His Phe Ser Gly Arg Pro Arg Glu Asp
             35                  40                  45

Arg Val Pro His Ser Arg Asn Ser Ile Thr Leu Thr Asn Leu Thr Pro
 50                  55                  60

Gly Thr Glu Tyr Val Val Ser Ile Val Ala Leu Asn Gly Arg Glu Glu
 65                  70                  75                  80

Ser Pro Pro Leu Ile Gly Gln Gln Ser Thr Val Ser Asp Val Pro Arg
                85                  90                  95

Asp Leu Glu Val Val Ala Ala Thr Pro Thr Ser Leu Leu Ile Ser Trp
                100                 105                 110

Asp Ala Pro Ala Val Thr Val Arg Tyr Tyr Arg Ile Thr Tyr Gly Glu
            115                 120                 125

Thr Gly Gly Asn Ser Pro Val Gln Glu Phe Thr Val Pro Gly Ser Lys
130                 135                 140

Ser Thr Ala Thr Ile Ser Gly Leu Lys Pro Gly Val Asp Tyr Thr Ile
145                 150                 155                 160

Thr Val Tyr Ala Val Thr Gly Arg Gly Asp Ser Pro Ala Ser Ser Lys
                165                 170                 175

Pro Ile Ser Ile Asn Tyr Arg Thr Arg Arg Pro Lys Gly Arg Gly
            180                 185                 190

Lys Arg Arg Arg Glu Lys Gln Arg Pro Thr Asp Cys His Leu
195                 200                 205
```

<210> SEQ ID NO 26
<211> LENGTH: 34
<212> TYPE: PRT
<213> ORGANISM: homo sapiens

<400> SEQUENCE: 26

```
Ser Val Ser Glu Ile Gln Leu Met His Asn Leu Gly Lys His Leu Asn
 1               5                  10                  15

Ser Met Glu Arg Val Glu Trp Leu Arg Lys Lys Leu Gln Asp Val His
                20                  25                  30
```

Asn Phe

<210> SEQ ID NO 27
<211> LENGTH: 56
<212> TYPE: PRT
<213> ORGANISM: artificial
<220> FEATURE:
<223> OTHER INFORMATION: fusion protein of PTH1 and PlGF2 domain

<400> SEQUENCE: 27

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Arg Arg Arg Pro Lys Gly Arg Gly Lys Arg Arg Arg Glu Lys
        35                  40                  45

Gln Arg Pro Thr Asp Cys His Leu
    50                  55

<210> SEQ ID NO 28
<211> LENGTH: 58
<212> TYPE: PRT
<213> ORGANISM: Bos taurus

<400> SEQUENCE: 28

Arg Pro Asp Phe Cys Leu Glu Pro Pro Tyr Thr Gly Pro Cys Lys Ala
1               5                   10                  15

Arg Ile Ile Arg Tyr Phe Tyr Asn Ala Lys Ala Gly Leu Cys Gln Thr
            20                  25                  30

Phe Val Tyr Gly Gly Cys Arg Ala Lys Arg Asn Asn Phe Lys Ser Ala
        35                  40                  45

Glu Asp Cys Met Arg Thr Cys Gly Gly Ala
    50                  55

<210> SEQ ID NO 29
<211> LENGTH: 80
<212> TYPE: PRT
<213> ORGANISM: artificial
<220> FEATURE:
<223> OTHER INFORMATION: fusion protein of aprotinin and PlGF2 domain

<400> SEQUENCE: 29

Arg Pro Asp Phe Cys Leu Glu Pro Pro Tyr Thr Gly Pro Cys Lys Ala
1               5                   10                  15

Arg Ile Ile Arg Tyr Phe Tyr Asn Ala Lys Ala Gly Leu Cys Gln Thr
            20                  25                  30

Phe Val Tyr Gly Gly Cys Arg Ala Lys Arg Asn Asn Phe Lys Ser Ala
        35                  40                  45

Glu Asp Cys Met Arg Thr Cys Gly Gly Ala Arg Arg Arg Pro Lys Gly
    50                  55                  60

Arg Gly Lys Arg Arg Arg Glu Lys Gln Arg Pro Thr Asp Cys His Leu
65                  70                  75                  80

<210> SEQ ID NO 30
<211> LENGTH: 77
<212> TYPE: PRT
<213> ORGANISM: homo sapiens

<400> SEQUENCE: 30

Val Pro Leu Ser Arg Thr Val Arg Cys Thr Cys Ile Ser Ile Ser Asn

```
                 1               5                  10                 15
            Gln Pro Val Asn Pro Arg Ser Leu Glu Lys Leu Glu Ile Ile Pro Ala
                             20                  25                 30

Ser Gln Phe Cys Pro Arg Val Glu Ile Ile Ala Thr Met Lys Lys Lys
                             35                  40                 45

Gly Glu Lys Arg Cys Leu Asn Pro Glu Ser Lys Ala Ile Lys Asn Leu
                 50                  55                  60

Leu Lys Ala Val Ser Lys Glu Arg Ser Lys Arg Ser Pro
            65                  70                  75

<210> SEQ ID NO 31
<211> LENGTH: 99
<212> TYPE: PRT
<213> ORGANISM: Artificial Sequence
<220> FEATURE:
<223> OTHER INFORMATION: fusion protein of CKCL10 and P1GF2

<400> SEQUENCE: 31

Val Pro Leu Ser Arg Thr Val Arg Cys Thr Cys Ile Ser Ile Ser Asn
            1               5                  10                 15

Gln Pro Val Asn Pro Arg Ser Leu Glu Lys Leu Glu Ile Ile Pro Ala
                             20                  25                 30

Ser Gln Phe Cys Pro Arg Val Glu Ile Ile Ala Thr Met Lys Lys Lys
                             35                  40                 45

Gly Glu Lys Arg Cys Leu Asn Pro Glu Ser Lys Ala Ile Lys Asn Leu
                 50                  55                  60

Leu Lys Ala Val Ser Lys Glu Arg Ser Lys Arg Ser Pro Arg Arg Arg
            65                  70                  75                 80

Pro Lys Gly Arg Gly Lys Arg Arg Glu Lys Gln Arg Pro Thr Asp
                             85                  90                 95

Cys His Leu

<210> SEQ ID NO 32
<211> LENGTH: 73
<212> TYPE: PRT
<213> ORGANISM: artificial
<220> FEATURE:
<223> OTHER INFORMATION: fusion protein of CXCL11 and PLGF2 domain

<400> SEQUENCE: 32

Phe Pro Met Phe Lys Arg Gly Arg Cys Leu Cys Ile Gly Pro Gly Val
            1               5                  10                 15

Lys Ala Val Lys Val Ala Asp Ile Glu Lys Ala Ser Ile Met Tyr Pro
                             20                  25                 30

Ser Asn Asn Cys Asp Lys Ile Glu Val Ile Ile Thr Leu Lys Glu Asn
                             35                  40                 45

Lys Gly Gln Arg Cys Leu Asn Pro Lys Ser Lys Gln Ala Arg Leu Ile
                 50                  55                  60

Ile Lys Lys Val Glu Arg Lys Asn Phe
            65                  70

<210> SEQ ID NO 33
<211> LENGTH: 95
<212> TYPE: PRT
<213> ORGANISM: artificial
<220> FEATURE:
<223> OTHER INFORMATION: fusion protein of CXCL11 and PlGF2 domain

<400> SEQUENCE: 33
```

```
Phe Pro Met Phe Lys Arg Gly Arg Cys Leu Cys Ile Gly Pro Gly Val
 1               5                  10                  15

Lys Ala Val Lys Val Ala Asp Ile Glu Lys Ala Ser Ile Met Tyr Pro
            20                  25                  30

Ser Asn Asn Cys Asp Lys Ile Glu Val Ile Thr Leu Lys Glu Asn
        35                  40                  45

Lys Gly Gln Arg Cys Leu Asn Pro Lys Ser Lys Gln Ala Arg Leu Ile
    50                  55                  60

Ile Lys Lys Val Glu Arg Lys Asn Phe Arg Arg Pro Lys Gly Arg
65                  70                  75                  80

Gly Lys Arg Arg Arg Glu Lys Gln Arg Pro Thr Asp Cys His Leu
            85                  90                  95
```

<210> SEQ ID NO 34
<211> LENGTH: 138
<212> TYPE: PRT
<213> ORGANISM: homo sapiens

<400> SEQUENCE: 34

```
Gln Asp Pro Tyr Val Lys Glu Ala Glu Asn Leu Lys Lys Tyr Phe Asn
 1               5                  10                  15

Ala Gly His Ser Asp Val Ala Asp Asn Gly Thr Leu Phe Leu Gly Ile
            20                  25                  30

Leu Lys Asn Trp Lys Glu Glu Ser Asp Arg Lys Ile Met Gln Ser Gln
        35                  40                  45

Ile Val Ser Phe Tyr Phe Lys Leu Phe Lys Asn Phe Lys Asp Asp Gln
    50                  55                  60

Ser Ile Gln Lys Ser Val Glu Thr Ile Lys Glu Asp Met Asn Val Lys
65                  70                  75                  80

Phe Phe Asn Ser Asn Lys Lys Lys Arg Asp Asp Phe Glu Lys Leu Thr
                85                  90                  95

Asn Tyr Ser Val Thr Asp Leu Asn Val Gln Arg Lys Ala Ile His Glu
            100                 105                 110

Leu Ile Gln Val Met Ala Glu Leu Ser Pro Ala Ala Lys Thr Gly Lys
        115                 120                 125

Arg Lys Arg Ser Gln Met Leu Phe Arg Gly
    130                 135
```

<210> SEQ ID NO 35
<211> LENGTH: 160
<212> TYPE: PRT
<213> ORGANISM: artificial
<220> FEATURE:
<223> OTHER INFORMATION: fusion protein of interferon gamm and PLGF2

Phe Phe Asn Ser Asn Lys Lys Lys Arg Asp Asp Phe Glu Lys Leu Thr
                85                  90                  95
Asn Tyr Ser Val Thr Asp Leu Asn Val Gln Arg Lys Ala Ile His Glu
            100                 105                 110
Leu Ile Gln Val Met Ala Glu Leu Ser Pro Ala Ala Lys Thr Gly Lys
        115                 120                 125
Arg Lys Arg Ser Gln Met Leu Phe Arg Gly Arg Arg Pro Lys Gly
    130                 135                 140
Arg Gly Lys Arg Arg Glu Lys Gln Arg Pro Thr Asp Cys His Leu
145                 150                 155                 160

<210> SEQ ID NO 36
<211> LENGTH: 111
<212> TYPE: PRT
<213> ORGANISM: homo sapiens

<400> SEQUENCE: 36

Ser Asp Gly Gly Ala Gln Asp Cys Cys Leu Lys Tyr Ser Gln Arg Lys
1               5                   10                  15
Ile Pro Ala Lys Val Val Arg Ser Tyr Arg Lys Gln Glu Pro Ser Leu
            20                  25                  30
Gly Cys Ser Ile Pro Ala Ile Leu Phe Leu Pro Arg Lys Arg Ser Gln
        35                  40                  45
Ala Glu Leu Cys Ala Asp Pro Lys Glu Leu Trp Val Gln Gln Leu Met
    50                  55                  60
Gln His Leu Asp Lys Thr Pro Ser Pro Gln Lys Pro Ala Gln Gly Cys
65                  70                  75                  80
Arg Lys Asp Arg Gly Ala Ser Lys Thr Gly Lys Lys Gly Lys Gly Ser
                85                  90                  95
Lys Gly Cys Lys Arg Thr Glu Arg Ser Gln Thr Pro Lys Gly Pro
            100                 105                 110

<210> SEQ ID NO 37
<211> LENGTH: 96
<212> TYPE: PRT
<213> ORGANISM: artificial
<220> FEATURE:
<223> OTHER INFORMATION: fusion protein of CCL21 and PlGF2 domain

<400> SEQUENCE: 37

Ser Asp Gly Gly Ala Gln Asp Cys Cys Leu Lys Tyr Ser Gln Arg Lys
1               5                   10                  15
Ile Pro Ala Lys Val Val Arg Ser Tyr Arg Lys Gln Glu Pro Ser Leu
            20                  25                  30
Gly Cys Ser Ile Pro Ala Ile Leu Phe Leu Pro Arg Lys Arg Ser Gln
        35                  40                  45
Ala Glu Leu Cys Ala Asp Pro Lys Glu Leu Trp Val Gln Gln Leu Met
    50                  55                  60
Gln His Leu Asp Lys Thr Pro Ser Pro Gln Arg Arg Pro Lys Gly
65                  70                  75                  80
Arg Gly Lys Arg Arg Glu Lys Gln Arg Pro Thr Asp Cys His Leu
                85                  90                  95

<210> SEQ ID NO 38
<211> LENGTH: 9
<212> TYPE: PRT
<213> ORGANISM: homo sapiens

<400> SEQUENCE: 38

```
Ser Val Tyr Asp Phe Phe Val Trp Leu
1               5

<210> SEQ ID NO 39
<211> LENGTH: 35
<212> TYPE: PRT
<213> ORGANISM: artificial
<220> FEATURE:
<223> OTHER INFORMATION: human PlGF2domain and plasmin cleavage site

<400> SEQUENCE: 39

Arg Arg Arg Pro Lys Gly Arg Gly Lys Arg Arg Glu Lys Gln Arg
1               5                   10                  15

Pro Thr Asp Cys His Leu Ile Thr Phe Arg Ser Val Tyr Asp Phe Phe
            20                  25                  30

Val Trp Leu
        35

<210> SEQ ID NO 40
<211> LENGTH: 496
<212> TYPE: PRT
<213> ORGANISM: homo sapiens

<400> SEQUENCE: 40

Gln Phe Pro Arg Val Cys Met Thr Val Asp Ser Leu Val Asn Lys Glu
1               5                   10                  15

Cys Cys Pro Arg Leu Gly Ala Glu Ser Ala Asn Val Cys Gly Ser Gln
            20                  25                  30

Gln Gly Arg Gly Gln Cys Thr Glu Val Arg Ala Asp Thr Arg Pro Trp
        35                  40                  45

Ser Gly Pro Tyr Ile Leu Arg Asn Gln Asp Asp Arg Glu Leu Trp Pro
    50                  55                  60

Arg Lys Phe Phe His Arg Thr Cys Lys Cys Thr Gly Asn Phe Ala Gly
65                  70                  75                  80

Tyr Asn Cys Gly Asp Cys Lys Phe Gly Trp Thr Gly Pro Asn Cys Glu
                85                  90                  95

Arg Lys Lys Pro Pro Val Ile Arg Gln Asn Ile His Ser Leu Ser Pro
            100                 105                 110

Gln Glu Arg Glu Gln Phe Leu Gly Ala Leu Asp Leu Ala Lys Lys Arg
        115                 120                 125

Val His Pro Asp Tyr Val Ile Thr Thr Gln His Trp Leu Gly Leu Leu
    130                 135                 140

Gly Pro Asn Gly Thr Gln Pro Gln Phe Ala Asn Cys Ser Val Tyr Asp
145                 150                 155                 160

Phe Phe Val Trp Leu His Tyr Tyr Ser Val Arg Asp Thr Leu Leu Gly
                165                 170                 175

Pro Gly Arg Pro Tyr Arg Ala Ile Asp Phe Ser His Gln Gly Pro Ala
            180                 185                 190

Phe Val Thr Trp His Arg Tyr His Leu Leu Cys Leu Glu Arg Asp Leu
        195                 200                 205

Gln Arg Leu Ile Gly Asn Glu Ser Phe Ala Leu Pro Tyr Trp Asn Phe
    210                 215                 220

Ala Thr Gly Arg Asn Glu Cys Asp Val Cys Thr Asp Gln Leu Phe Gly
225                 230                 235                 240

Ala Ala Arg Pro Asp Asp Pro Thr Leu Ile Ser Arg Asn Ser Arg Phe
                245                 250                 255
```

```
Ser Ser Trp Glu Thr Val Cys Asp Ser Leu Asp Asp Tyr Asn His Leu
            260                 265                 270

Val Thr Leu Cys Asn Gly Thr Tyr Glu Gly Leu Leu Arg Arg Asn Gln
        275                 280                 285

Met Gly Arg Asn Ser Met Lys Leu Pro Thr Leu Lys Asp Ile Arg Asp
    290                 295                 300

Cys Leu Ser Leu Gln Lys Phe Asp Asn Pro Phe Phe Gln Asn Ser
305                 310                 315                 320

Thr Phe Ser Phe Arg Asn Ala Leu Glu Gly Phe Asp Lys Ala Asp Gly
                325                 330                 335

Thr Leu Asp Ser Gln Val Met Ser Leu His Asn Leu Val His Ser Phe
            340                 345                 350

Leu Asn Gly Thr Asn Ala Leu Pro His Ser Ala Ala Asn Asp Pro Ile
        355                 360                 365

Phe Val Val Leu His Ser Phe Thr Asp Ala Ile Phe Asp Glu Trp Met
    370                 375                 380

Lys Arg Phe Asn Pro Pro Ala Asp Ala Trp Pro Gln Glu Leu Ala Pro
385                 390                 395                 400

Ile Gly His Asn Arg Met Tyr Asn Met Val Pro Phe Phe Pro Pro Val
                405                 410                 415

Thr Asn Glu Glu Leu Phe Leu Thr Ser Asp Gln Leu Gly Tyr Ser Tyr
            420                 425                 430

Ala Ile Asp Leu Pro Val Ser Val Glu Glu Thr Pro Gly Trp Pro Thr
        435                 440                 445

Thr Leu Leu Val Val Met Gly Thr Leu Val Ala Leu Val Gly Leu Phe
    450                 455                 460

Val Leu Leu Ala Phe Leu Gln Tyr Arg Arg Leu Arg Lys Gly Tyr Thr
465                 470                 475                 480

Pro Leu Met Glu Thr His Leu Ser Ser Lys Arg Tyr Thr Glu Glu Ala
                485                 490                 495

<210> SEQ ID NO 41
<211> LENGTH: 518
<212> TYPE: PRT
<213> ORGANISM: artificial
<220> FEATURE:
<223> OTHER INFORMATION: fusion protein of human L-dopachrome
      tautomerase and PlGF2 domain

<400> SEQUENCE: 41

Gln Phe Pro Arg Val Cys Met Thr Val Asp Ser Leu Val Asn Lys Glu
1               5                   10                  15

Cys Cys Pro Arg Leu Gly Ala Glu Ser Ala Asn Val Cys Gly Ser Gln
                20                  25                  30

Gln Gly Arg Gly Gln Cys Thr Glu Val Arg Ala Asp Thr Arg Pro Trp
            35                  40                  45

Ser Gly Pro Tyr Ile Leu Arg Asn Gln Asp Asp Arg Glu Leu Trp Pro
        50                  55                  60

Arg Lys Phe Phe His Arg Thr Cys Lys Cys Thr Gly Asn Phe Ala Gly
65                  70                  75                  80

Tyr Asn Cys Gly Asp Cys Lys Phe Gly Trp Thr Gly Pro Asn Cys Glu
                85                  90                  95

Arg Lys Lys Pro Pro Val Ile Arg Gln Asn Ile His Ser Leu Ser Pro
            100                 105                 110

Gln Glu Arg Glu Gln Phe Leu Gly Ala Leu Asp Leu Ala Lys Lys Arg
        115                 120                 125
```

Val His Pro Asp Tyr Val Ile Thr Thr Gln His Trp Leu Gly Leu Leu
    130                 135                 140

Gly Pro Asn Gly Thr Gln Pro Gln Phe Ala Asn Cys Ser Val Tyr Asp
145                 150                 155                 160

Phe Phe Val Trp Leu His Tyr Tyr Ser Val Arg Asp Thr Leu Leu Gly
                165                 170                 175

Pro Gly Arg Pro Tyr Arg Ala Ile Asp Phe Ser His Gln Gly Pro Ala
                180                 185                 190

Phe Val Thr Trp His Arg Tyr His Leu Leu Cys Leu Glu Arg Asp Leu
            195                 200                 205

Gln Arg Leu Ile Gly Asn Glu Ser Phe Ala Leu Pro Tyr Trp Asn Phe
210                 215                 220

Ala Thr Gly Arg Asn Glu Cys Asp Val Cys Thr Asp Gln Leu Phe Gly
225                 230                 235                 240

Ala Ala Arg Pro Asp Asp Pro Thr Leu Ile Ser Arg Asn Ser Arg Phe
                245                 250                 255

Ser Ser Trp Glu Thr Val Cys Asp Ser Leu Asp Asp Tyr Asn His Leu
                260                 265                 270

Val Thr Leu Cys Asn Gly Thr Tyr Glu Gly Leu Leu Arg Arg Asn Gln
            275                 280                 285

Met Gly Arg Asn Ser Met Lys Leu Pro Thr Leu Lys Asp Ile Arg Asp
290                 295                 300

Cys Leu Ser Leu Gln Lys Phe Asp Asn Pro Pro Phe Phe Gln Asn Ser
305                 310                 315                 320

Thr Phe Ser Phe Arg Asn Ala Leu Glu Gly Phe Asp Lys Ala Asp Gly
                325                 330                 335

Thr Leu Asp Ser Gln Val Met Ser Leu His Asn Leu Val His Ser Phe
            340                 345                 350

Leu Asn Gly Thr Asn Ala Leu Pro His Ser Ala Ala Asn Asp Pro Ile
            355                 360                 365

Phe Val Val Leu His Ser Phe Thr Asp Ala Ile Phe Asp Glu Trp Met
370                 375                 380

Lys Arg Phe Asn Pro Pro Ala Asp Ala Trp Pro Gln Glu Leu Ala Pro
385                 390                 395                 400

Ile Gly His Asn Arg Met Tyr Asn Met Val Pro Phe Phe Pro Pro Val
                405                 410                 415

Thr Asn Glu Glu Leu Phe Leu Thr Ser Asp Gln Leu Gly Tyr Ser Tyr
            420                 425                 430

Ala Ile Asp Leu Pro Val Ser Val Glu Glu Thr Pro Gly Trp Pro Thr
            435                 440                 445

Thr Leu Leu Val Val Met Gly Thr Leu Val Ala Leu Val Gly Leu Phe
450                 455                 460

Val Leu Leu Ala Phe Leu Gln Tyr Arg Arg Leu Arg Lys Gly Tyr Thr
465                 470                 475                 480

Pro Leu Met Glu Thr His Leu Ser Ser Lys Arg Tyr Thr Glu Glu Ala
                485                 490                 495

Arg Arg Arg Pro Lys Gly Arg Gly Lys Arg Arg Glu Lys Gln Arg
                500                 505                 510

Pro Thr Asp Cys His Leu
            515

<210> SEQ ID NO 42
<211> LENGTH: 229

-continued

<212> TYPE: PRT
<213> ORGANISM: homo sapiens

<400> SEQUENCE: 42

Gly Leu Leu Tyr Pro Phe Pro Lys Asp Cys Ser Gln Ala Met Leu Asn
1               5                   10                  15

Gly Asp Thr Thr Ser Gly Leu Tyr Thr Ile Tyr Leu Asn Gly Asp Lys
            20                  25                  30

Ala Gln Ala Leu Glu Val Phe Cys Asp Met Thr Ser Asp Gly Gly Gly
        35                  40                  45

Trp Ile Val Phe Leu Arg Arg Lys Asn Gly Arg Glu Asn Phe Tyr Gln
50                  55                  60

Asn Trp Lys Ala Tyr Ala Ala Gly Phe Gly Asp Arg Arg Glu Glu Phe
65                  70                  75                  80

Leu His Trp Leu Gly Leu Asp Asn Leu Asn Lys Ile Thr Ala Gln Gly
                85                  90                  95

Gln Tyr Glu Leu Arg Val Asp Leu Arg Asp His Gly Glu Thr Ala Phe
            100                 105                 110

Ala Val Tyr Asp Lys Phe Ser Val Gly Asp Ala Lys Thr Arg Tyr Lys
        115                 120                 125

Leu Lys Val Glu Gly Tyr Ser Gly Thr Ala Gly Asp Ser Met Ala Tyr
130                 135                 140

His Asn Gly Arg Ser Phe Ser Thr Phe Asp Lys Asp Thr Asp Ser Ala
145                 150                 155                 160

Ile Thr Asn Cys Ala Leu Ser Tyr Lys Gly Ala Phe Trp Tyr Arg Asn
                165                 170                 175

Cys His Arg Val Asn Leu Met Gly Arg Tyr Gly Asp Asn Asn His Ser
            180                 185                 190

Gln Gly Val Asn Trp Phe His Trp Lys Gly His Glu His Ser Ile Gln
        195                 200                 205

Phe Ala Glu Met Lys Leu Arg Pro Ser Asn Phe Arg Asn Leu Glu Gly
210                 215                 220

Arg Arg Lys Arg Ala
225

<210> SEQ ID NO 43
<211> LENGTH: 246
<212> TYPE: PRT
<213> ORGANISM: artificial sequence
<220> FEATURE:
<223> OTHER INFORMATION: fusion protein of tenascin fibrinogen globular
      domain and PlGF2 domain

<400> SEQUENCE: 43

Gly Leu Leu Tyr Pro Phe Pro Lys Asp Cys Ser Gln Ala Met Leu Asn
1               5                   10                  15

Gly Asp Thr Thr Ser Gly Leu Tyr Thr Ile Tyr Leu Asn Gly Asp Lys
            20                  25                  30

Ala Gln Ala Leu Glu Val Phe Cys Asp Met Thr Ser Asp Gly Gly Gly
        35                  40                  45

Trp Ile Val Phe Leu Arg Arg Lys Asn Gly Arg Glu Asn Phe Tyr Gln
50                  55                  60

Asn Trp Lys Ala Tyr Ala Ala Gly Phe Gly Asp Arg Arg Glu Glu Phe
65                  70                  75                  80

Leu His Trp Leu Gly Leu Asp Asn Leu Asn Lys Ile Thr Ala Gln Gly
                85                  90                  95

```
Gln Tyr Glu Leu Arg Val Asp Leu Arg Asp His Gly Glu Thr Ala Phe
            100                 105                 110

Ala Val Tyr Asp Lys Phe Ser Val Gly Asp Ala Lys Thr Arg Tyr Lys
        115                 120                 125

Leu Lys Val Glu Gly Tyr Ser Gly Thr Ala Gly Asp Ser Met Ala Tyr
    130                 135                 140

His Asn Gly Arg Ser Phe Ser Thr Phe Asp Lys Asp Thr Asp Ser Ala
145                 150                 155                 160

Ile Thr Asn Cys Ala Leu Ser Tyr Lys Gly Ala Phe Trp Tyr Arg Asn
                165                 170                 175

Cys His Arg Val Asn Leu Met Gly Arg Tyr Gly Asp Asn Asn His Ser
            180                 185                 190

Gln Gly Val Asn Trp Phe His Trp Lys Gly His Glu His Ser Ile Gln
        195                 200                 205

Phe Ala Glu Met Lys Leu Arg Pro Ser Asn Phe Arg Asn Leu Glu Gly
    210                 215                 220

Arg Arg Arg Pro Lys Gly Arg Gly Lys Arg Arg Glu Lys Gln Arg
225                 230                 235                 240

Pro Thr Asp Cys His Leu
                245

<210> SEQ ID NO 44
<211> LENGTH: 180
<212> TYPE: PRT
<213> ORGANISM: homo sapiens

<400> SEQUENCE: 44

Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
            20                  25                  30

Arg Thr Ser Gly Lys His Ile Gln Val Leu Gly Arg Arg Ile Ser Ala
        35                  40                  45

Arg Gly Glu Asp Gly Asp Lys Tyr Ala Gln Leu Leu Val Glu Thr Asp
    50                  55                  60

Thr Phe Gly Ser Gln Val Arg Ile Lys Gly Lys Glu Thr Glu Phe Tyr
65                  70                  75                  80

Leu Cys Met Asn Arg Lys Gly Lys Leu Val Gly Lys Pro Asp Gly Thr
                85                  90                  95

Ser Lys Glu Cys Val Phe Ile Glu Lys Val Leu Glu Asn Asn Tyr Thr
            100                 105                 110

Ala Leu Met Ser Ala Lys Tyr Ser Gly Trp Tyr Val Gly Phe Thr Lys
        115                 120                 125

Lys Gly Arg Pro Arg Lys Gly Pro Lys Thr Arg Glu Asn Gln Gln Asp
    130                 135                 140

Val His Phe Met Lys Arg Tyr Pro Lys Gly Gln Pro Glu Leu Gln Lys
145                 150                 155                 160

Pro Phe Lys Tyr Thr Thr Val Thr Lys Arg Ser Arg Arg Ile Arg Pro
                165                 170                 175

Thr His Pro Ala
            180

<210> SEQ ID NO 45
<211> LENGTH: 202
<212> TYPE: PRT
<213> ORGANISM: artificial
```

<220> FEATURE:
<223> OTHER INFORMATION: fusion protein of FGF-18 and PlGF2 domain

<400> SEQUENCE: 45

Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
            20                  25                  30

Arg Thr Ser Gly Lys His Ile Gln Val Leu Gly Arg Arg Ile Ser Ala
        35                  40                  45

Arg Gly Glu Asp Gly Asp Lys Tyr Ala Gln Leu Leu Val Glu Thr Asp
    50                  55                  60

Thr Phe Gly Ser Gln Val Arg Ile Lys Gly Lys Glu Thr Glu Phe Tyr
65                  70                  75                  80

Leu Cys Met Asn Arg Lys Gly Lys Leu Val Gly Lys Pro Asp Gly Thr
                85                  90                  95

Ser Lys Glu Cys Val Phe Ile Glu Lys Val Leu Glu Asn Asn Tyr Thr
            100                 105                 110

Ala Leu Met Ser Ala Lys Tyr Ser Gly Trp Tyr Val Gly Phe Thr Lys
        115                 120                 125

Lys Gly Arg Pro Arg Lys Gly Pro Lys Thr Arg Glu Asn Gln Gln Asp
    130                 135                 140

Val His Phe Met Lys Arg Tyr Pro Lys Gly Gln Pro Glu Leu Gln Lys
145                 150                 155                 160

Pro Phe Lys Tyr Thr Thr Val Thr Lys Arg Ser Arg Arg Ile Arg Pro
                165                 170                 175

Thr His Pro Ala Arg Arg Pro Lys Gly Arg Gly Lys Arg Arg Arg
            180                 185                 190

Glu Lys Gln Arg Pro Thr Asp Cys His Leu
    195                 200

<210> SEQ ID NO 46
<211> LENGTH: 112
<212> TYPE: PRT
<213> ORGANISM: homo sapiens

<400> SEQUENCE: 46

Ala Leu Asp Thr Asn Tyr Cys Phe Arg Asn Leu Glu Glu Asn Cys Cys
1               5                   10                  15

Val Arg Pro Leu Tyr Ile Asp Phe Arg Gln Asp Leu Gly Trp Lys Trp
            20                  25                  30

Val His Glu Pro Lys Gly Tyr Tyr Ala Asn Phe Cys Ser Gly Pro Cys
        35                  40                  45

Pro Tyr Leu Arg Ser Ala Asp Thr Thr His Ser Thr Val Leu Gly Leu
    50                  55                  60

Tyr Asn Thr Leu Asn Pro Glu Ala Ser Ala Ser Pro Cys Cys Val Pro
65                  70                  75                  80

Gln Asp Leu Glu Pro Leu Thr Ile Leu Tyr Tyr Val Gly Arg Thr Pro
                85                  90                  95

Lys Val Glu Gln Leu Ser Asn Met Val Val Lys Ser Cys Lys Cys Ser
            100                 105                 110

<210> SEQ ID NO 47
<211> LENGTH: 134
<212> TYPE: PRT
<213> ORGANISM: artificial
<220> FEATURE:

-continued

<223> OTHER INFORMATION: fusion protein of TGF beta3 and PlGF2 domain

<400> SEQUENCE: 47

Arg Arg Arg Pro Lys Gly Arg Gly Lys Arg Arg Glu Lys Gln Arg
1               5                   10                  15

Pro Thr Asp Ser His Leu Ala Leu Asp Thr Asn Tyr Cys Phe Arg Asn
            20                  25                  30

Leu Glu Glu Asn Cys Cys Val Arg Pro Leu Tyr Ile Asp Phe Arg Gln
        35                  40                  45

Asp Leu Gly Trp Lys Trp Val His Glu Pro Lys Gly Tyr Tyr Ala Asn
    50                  55                  60

Phe Cys Ser Gly Pro Cys Pro Tyr Leu Arg Ser Ala Asp Thr Thr His
65                  70                  75                  80

Ser Thr Val Leu Gly Leu Tyr Asn Thr Leu Asn Pro Glu Ala Ser Ala
                85                  90                  95

Ser Pro Cys Cys Val Pro Gln Asp Leu Glu Pro Leu Thr Ile Leu Tyr
            100                 105                 110

Tyr Val Gly Arg Thr Pro Lys Val Glu Gln Leu Ser Asn Met Val Val
                115                 120                 125

Lys Ser Cys Lys Cys Ser
    130

<210> SEQ ID NO 48
<211> LENGTH: 5
<212> TYPE: PRT
<213> ORGANISM: artificial
<220> FEATURE:
<223> OTHER INFORMATION: adhesion motif

<400> SEQUENCE: 48

Ile Asp Ala Pro Ser
1               5

<210> SEQ ID NO 49
<211> LENGTH: 7
<212> TYPE: PRT
<213> ORGANISM: artificial
<220> FEATURE:
<223> OTHER INFORMATION: adhesion motif

<400> SEQUENCE: 49

Ile Asp Gly Ile His Glu Leu
1               5

<210> SEQ ID NO 50
<211> LENGTH: 8
<212> TYPE: PRT
<213> ORGANISM: artificial
<220> FEATURE:
<223> OTHER INFORMATION: residues 1 to 8 of alpha-2 plasmin inhibitor

<400> SEQUENCE: 50

Asn Gln Glu Gln Val Ser Pro Leu
1               5

<210> SEQ ID NO 51
<211> LENGTH: 6
<212> TYPE: PRT
<213> ORGANISM: artificial
<220> FEATURE:
<223> OTHER INFORMATION: adhesion motif

<400> SEQUENCE: 51

-continued

```
Lys Leu Asp Ala Pro Thr
1               5

<210> SEQ ID NO 52
<211> LENGTH: 5
<212> TYPE: PRT
<213> ORGANISM: artificial
<220> FEATURE:
<223> OTHER INFORMATION: adhesion motif

<400> SEQUENCE: 52

Arg Gly Asp Ser Pro
1               5

<210> SEQ ID NO 53
<211> LENGTH: 189
<212> TYPE: PRT
<213> ORGANISM: artificial
<220> FEATURE:
<223> OTHER INFORMATION: fusion protein of FGF-18 anjd PlGF2 domain

<400> SEQUENCE: 53

Glu Glu Asn Val Asp Phe Arg Ile His Val Glu Asn Gln Thr Arg Ala
1               5                  10                  15

Arg Asp Asp Val Ser Arg Lys Gln Leu Arg Leu Tyr Gln Leu Tyr Ser
            20                  25                  30

Arg Thr Ser Gly Lys His Ile Gln Val Leu Gly Arg Arg Ile Ser Ala
        35                  40                  45

Arg Gly Glu Asp Gly Asp Lys Tyr Ala Gln Leu Leu Val Glu Thr Asp
    50                  55                  60

Thr Phe Gly Ser Gln Val Arg Ile Lys Gly Lys Glu Thr Glu Phe Tyr
65                  70                  75                  80

Leu Cys Met Asn Arg Lys Gly Lys Leu Val Gly Lys Pro Asp Gly Thr
                85                  90                  95

Ser Lys Glu Cys Val Phe Ile Glu Lys Val Leu Glu Asn Asn Tyr Thr
            100                 105                 110

Ala Leu Met Ser Ala Lys Tyr Ser Gly Trp Tyr Val Gly Phe Thr Lys
        115                 120                 125

Lys Gly Arg Pro Arg Lys Gly Pro Lys Thr Arg Glu Asn Gln Gln Asp
    130                 135                 140

Val His Phe Met Lys Arg Tyr Pro Lys Gly Gln Pro Glu Leu Gln Lys
145                 150                 155                 160

Pro Phe Lys Tyr Thr Thr Val Thr Arg Arg Arg Pro Lys Gly Arg Gly
                165                 170                 175

Lys Arg Arg Arg Glu Lys Gln Arg Pro Thr His Pro Ala
            180                 185

<210> SEQ ID NO 54
<211> LENGTH: 172
<212> TYPE: PRT
<213> ORGANISM: artificial
<220> FEATURE:
<223> OTHER INFORMATION: fusion protein of FGF -18 and PlGF2 domain

<400> SEQUENCE: 54

Glu Glu Asn Val Asp Phe Arg Ile His Val Glu Asn Gln Thr Arg Ala
1               5                  10                  15

Arg Asp Asp Val Ser Arg Lys Gln Leu Arg Leu Tyr Gln Leu Tyr Ser
            20                  25                  30
```

```
Arg Thr Ser Gly Lys His Ile Gln Val Leu Gly Arg Ile Ser Ala
         35                  40                  45

Arg Gly Glu Asp Gly Asp Lys Tyr Ala Gln Leu Leu Val Glu Thr Asp
 50                  55                  60

Thr Phe Gly Ser Gln Val Arg Ile Lys Gly Lys Glu Thr Glu Phe Tyr
 65                  70                  75                  80

Leu Cys Met Asn Arg Lys Gly Lys Leu Val Gly Lys Pro Asp Gly Thr
                 85                  90                  95

Ser Lys Glu Cys Val Phe Ile Glu Lys Val Leu Glu Asn Asn Tyr Thr
            100                 105                 110

Ala Leu Met Ser Ala Lys Tyr Ser Gly Trp Tyr Val Gly Phe Thr Lys
        115                 120                 125

Lys Gly Arg Pro Arg Lys Gly Pro Lys Thr Arg Glu Asn Gln Gln Asp
    130                 135                 140

Val His Phe Met Lys Pro Glu Arg Arg Pro Lys Gly Arg Gly Lys
145                 150                 155                 160

Arg Arg Arg Glu Lys Gln Arg Pro Thr His Pro Ala
                165                 170

<210> SEQ ID NO 55
<211> LENGTH: 26
<212> TYPE: PRT
<213> ORGANISM: artificial
<220> FEATURE:
<223> OTHER INFORMATION: portion of PlGF2 domain

<400> SEQUENCE: 55

Met Lys Pro Glu Arg Arg Pro Lys Gly Arg Gly Lys Arg Arg
1                5                  10                  15

Glu Lys Gln Arg Pro Thr Asp Cys His Leu
            20                  25

<210> SEQ ID NO 56
<211> LENGTH: 27
<212> TYPE: PRT
<213> ORGANISM: artificial
<220> FEATURE:
<223> OTHER INFORMATION: FGF-18 heparin binding site

<400> SEQUENCE: 56

Lys Arg Tyr Pro Lys Gly Gln Pro Glu Leu Gln Lys Pro Phe Lys Tyr
1                5                  10                  15

Thr Thr Val Thr Lys Arg Ser Arg Arg Ile Arg
            20                  25

<210> SEQ ID NO 57
<211> LENGTH: 7
<212> TYPE: PRT
<213> ORGANISM: artificial
<220> FEATURE:
<223> OTHER INFORMATION: portion of FGF-18 heparin binding domain

<400> SEQUENCE: 57

Lys Arg Ser Arg Arg Ile Arg
1                5

<210> SEQ ID NO 58
<211> LENGTH: 131
<212> TYPE: PRT
<213> ORGANISM: artificial
<220> FEATURE:
<223> OTHER INFORMATION: PlGf1 domain
```

<400> SEQUENCE: 58

Leu Pro Ala Val Pro Gln Gln Trp Ala Leu Ser Ala Gly Asn Gly
1               5                   10                  15

Ser Ser Glu Val Glu Val Val Pro Phe Gln Glu Val Trp Gly Arg Ser
            20                  25                  30

Tyr Cys Arg Ala Leu Glu Arg Leu Val Asp Val Val Ser Glu Tyr Pro
        35                  40                  45

Ser Glu Val Glu His Met Phe Ser Pro Ser Cys Val Ser Leu Leu Arg
    50                  55                  60

Cys Thr Gly Cys Cys Gly Asp Glu Asn Leu His Cys Val Pro Val Glu
65                  70                  75                  80

Thr Ala Asn Val Thr Met Gln Leu Leu Lys Ile Arg Ser Gly Asp Arg
                85                  90                  95

Pro Ser Tyr Val Glu Leu Thr Phe Ser Gln His Val Arg Cys Glu Cys
            100                 105                 110

Arg Pro Leu Arg Glu Lys Met Lys Pro Glu Arg Cys Gly Asp Ala Val
        115                 120                 125

Pro Arg Arg
    130

<210> SEQ ID NO 59
<211> LENGTH: 150
<212> TYPE: PRT
<213> ORGANISM: artificial
<220> FEATURE:
<223> OTHER INFORMATION: PlGF2 domain

<400> SEQUENCE: 59

Pro Ala Val Pro Pro Gln Gln Trp Ala Leu Ser Ala Gly Asn Gly Ser
1               5                   10                  15

Ser Glu Val Glu Val Val Pro Phe Gln Glu Val Trp Gly Arg Ser Tyr
            20                  25                  30

Cys Arg Ala Leu Glu Arg Leu Val Asp Val Val Ser Glu Tyr Pro Ser
        35                  40                  45

Glu Val Glu His Met Phe Ser Pro Ser Cys Val Ser Leu Leu Arg Cys
    50                  55                  60

Thr Gly Cys Cys Gly Asp Glu Asn Leu His Cys Val Pro Val Glu Thr
65                  70                  75                  80

Ala Asn Val Thr Met Gln Leu Leu Lys Ile Arg Ser Gly Asp Arg Pro
                85                  90                  95

Ser Tyr Val Glu Leu Thr Phe Ser Gln His Val Arg Cys Glu Cys Arg
            100                 105                 110

Pro Leu Arg Glu Lys Met Lys Pro Glu Arg Arg Pro Lys Arg Gly
        115                 120                 125

Lys Arg Arg Arg Glu Lys Gln Arg Pro Thr Asp Cys His Leu Cys Gly
    130                 135                 140

Asp Ala Val Pro Arg Arg
145             150

<210> SEQ ID NO 60
<211> LENGTH: 30
<212> TYPE: PRT
<213> ORGANISM: artificial
<220> FEATURE:
<223> OTHER INFORMATION: alignement of GST-PLGF2 furion protein

<400> SEQUENCE: 60

```
Arg Arg Arg Pro Lys Gly Arg Gly Lys Arg Arg Glu Lys Gln Arg
1               5                   10                  15

Pro Thr Asp Cys His Leu Cys Gly Asp Ala Val Pro Arg Arg
            20                  25                  30

<210> SEQ ID NO 61
<211> LENGTH: 22
<212> TYPE: PRT
<213> ORGANISM: artificial
<220> FEATURE:
<223> OTHER INFORMATION: Altignment of GST-PlGF2 furion protein

<400> SEQUENCE: 61

Arg Arg Arg Pro Lys Gly Arg Gly Lys Arg Arg Glu Lys Gln Arg
1               5                   10                  15

Pro Thr Asp Cys His Leu
            20

<210> SEQ ID NO 62
<211> LENGTH: 18
<212> TYPE: PRT
<213> ORGANISM: artificial
<220> FEATURE:
<223> OTHER INFORMATION: alignment of GST-PlGF2 fusion protein

<400> SEQUENCE: 62

Arg Arg Pro Lys Gly Arg Gly Lys Arg Arg Glu Lys Gln Arg Pro
1               5                   10                  15

Thr Asp

<210> SEQ ID NO 63
<211> LENGTH: 8
<212> TYPE: PRT
<213> ORGANISM: Artificial Sequence
<220> FEATURE:
<223> OTHER INFORMATION: MHC I epitope

<400> SEQUENCE: 63

Ser Ile Ile Asn Phe Glu Lys Leu
1               5

<210> SEQ ID NO 64
<211> LENGTH: 4
<212> TYPE: PRT
<213> ORGANISM: Artificial Sequence
<220> FEATURE:
<223> OTHER INFORMATION: adhesion domain

<400> SEQUENCE: 64

Arg Gly Asp Ser
1

<210> SEQ ID NO 65
<211> LENGTH: 4
<212> TYPE: PRT
<213> ORGANISM: Artificial Sequence
<220> FEATURE:
<223> OTHER INFORMATION: adhesion domain

<400> SEQUENCE: 65

Arg Glu Asp Val
1

<210> SEQ ID NO 66
```

```
<211> LENGTH: 6
<212> TYPE: PRT
<213> ORGANISM: Artificial Sequence
<220> FEATURE:
<223> OTHER INFORMATION: tenascin domain

<400> SEQUENCE: 66

Lys Leu Asp Ala Pro Thr
1               5
```